(12) United States Patent
MacGregor

(10) Patent No.: US 9,061,061 B2
(45) Date of Patent: Jun. 23, 2015

(54) METHOD OF TREATING DYSGLYCEMIA AND GLUCOSE EXCURSIONS

(75) Inventor: Alexander MacGregor, Markham (CA)

(73) Assignee: ORX PHARMACEUTICAL CORPORATION, Toronto, Ontario (CA)

( * ) Notice: Subject to any disclaimer, the term of this patent is extended or adjusted under 35 U.S.C. 154(b) by 436 days.

(21) Appl. No.: 12/744,301

(22) PCT Filed: Aug. 24, 2009

(86) PCT No.: PCT/CA2009/001166
§ 371 (c)(1), (2), (4) Date: Mar. 14, 2011

(87) PCT Pub. No.: WO2010/022497
PCT Pub. Date: Mar. 4, 2010

(65) Prior Publication Data
US 2011/0159045 A1    Jun. 30, 2011

(30) Foreign Application Priority Data
Aug. 29, 2008 (CA) .................................... 2638240

(51) Int. Cl.
A61K 31/155 (2006.01)
A61K 45/06 (2006.01)
A61K 9/20 (2006.01)

(52) U.S. Cl.
CPC ............... *A61K 45/06* (2013.01); *A61K 9/2013* (2013.01); *A61K 9/2027* (2013.01); *A61K 9/2054* (2013.01); *A61K 9/2086* (2013.01); *A61K 31/155* (2013.01)

(58) Field of Classification Search
CPC . A61K 31/155; A61K 9/2031; A61K 9/2846; A61K 9/2027; A61K 9/2095
See application file for complete search history.

(56) References Cited

U.S. PATENT DOCUMENTS 4,765,983 A * 8/1988 Takayanagi et al. .......... 424/434
4,849,227 A    7/1989 Cho
(Continued)

FOREIGN PATENT DOCUMENTS

CA    2 341 908    3/2000
CA    2 380 642    2/2001
(Continued)

*Primary Examiner* — Lakshmi Channavajjala
(74) *Attorney, Agent, or Firm* — Neifeld IP Law, PC

(57) ABSTRACT

The present application relates to pharmaceutical compositions for reducing glucose excursions in a normal subject or a subject having an insulin-related disorder or dysglycemia. The pharmaceutical composition contains one or more active agent-containing layers, which each contain a dry blended mixture including a therapeutically effective amount of a polar ionizable insulin-sensitizing oral hypoglycemic agent or a pharmaceutically acceptable salt thereof, and an amphipathic compound in monomelic form consisting of an amphipathic ionic compound in monomelic form. Each dry blended mixture contains a sufficient amount of the amphipathic ionic compound such that upon contact with an aqueous fluid, the amphipathic ionic compound forms a reverse micelle comprising the polar ionizable insulin-sensitizing oral hypoglycemic agent. The present invention also relates to a use of a modified release pharmaceutical composition comprising a therapeutically effective amount of an insulin-sensitizing oral hypoglycemic agent for sensitizing pre-prandial (basal) insulin levels and/or reducing postprandial glucose excursions in a normal patient or a patient having an insulin-related disorder.

18 Claims, 21 Drawing Sheets

(56) References Cited

U.S. PATENT DOCUMENTS

| | | |
|---|---|---|
| 5,413,572 A | 5/1995 | Wong et al. |
| 5,770,559 A | 6/1998 | Manning et al. |
| 5,858,398 A | 1/1999 | Cho |
| 5,945,125 A | 8/1999 | Kim |
| 6,086,920 A | 7/2000 | Frisbee et al. |
| 6,099,859 A | 8/2000 | Cheng et al. |
| 6,099,862 A | 8/2000 | Chen et al. |
| 6,248,363 B1 | 6/2001 | Patel et al. |
| 6,284,275 B1 | 9/2001 | Chen et al. |
| 6,309,663 B1 | 10/2001 | Patel et al. |
| 6,383,471 B1 | 5/2002 | Chen et al. |
| 6,426,087 B1 | 7/2002 | Saslawski et al. |
| 6,475,521 B1 | 11/2002 | Timmins et al. |
| 6,495,162 B2 | 12/2002 | Cheng et al. |
| 6,514,524 B1 | 2/2003 | Saslawski et al. |
| 6,652,837 B1 | 11/2003 | Edwards et al. |
| 6,660,300 B1 | 12/2003 | Timmins et al. |
| 6,673,612 B2 | 1/2004 | Monahan et al. |
| 6,790,459 B1 * | 9/2004 | Cheng et al. .................. 424/468 |
| 7,183,321 B2 * | 2/2007 | Li et al. .......................... 514/635 |
| 7,431,943 B1 | 10/2008 | Villa et al. |
| 7,727,551 B2 | 6/2010 | Massironi |
| 2002/0064556 A1 | 5/2002 | Cheng et al. |
| 2003/0003151 A1 | 1/2003 | Chopra |
| 2003/0021841 A1 | 1/2003 | Matharu et al. |
| 2003/0064097 A1 | 4/2003 | Patel et al. |
| 2003/0113366 A1 | 6/2003 | MacGregor |
| 2003/0133982 A1 | 7/2003 | Heimlich et al. |
| 2003/0219482 A1 | 11/2003 | Chaudhari et al. |
| 2003/0220301 A1 | 11/2003 | Lal et al. |
| 2003/0235595 A1 | 12/2003 | Chen et al. |
| 2004/0005358 A1 | 1/2004 | Slugg et al. |
| 2004/0213844 A1 | 10/2004 | Massironi |
| 2005/0051922 A1 | 3/2005 | Nangia et al. |
| 2005/0255156 A1 | 11/2005 | MacGregor |
| 2006/0002998 A1 | 1/2006 | Trehan et al. |
| 2006/0177499 A1 | 8/2006 | Besse |
| 2007/0093462 A1 | 4/2007 | Rogers et al. |
| 2007/0215511 A1 | 9/2007 | Mehta et al. |
| 2007/0219250 A1 | 9/2007 | Singh et al. |
| 2007/0281007 A1 * | 12/2007 | Jacob et al. .................. 424/452 |
| 2008/0020046 A1 | 1/2008 | Dawson et al. |
| 2008/0274177 A1 | 11/2008 | Zhou et al. |
| 2009/0069437 A1 | 3/2009 | Gluskin et al. |
| 2009/0105265 A1 | 4/2009 | Kamali et al. |
| 2009/0124702 A1 | 5/2009 | Siva Satya Krishna Babu et al. |
| 2009/0142378 A1 | 6/2009 | Frisbee |
| 2009/0186819 A1 | 7/2009 | Carrier et al. |
| 2009/0214605 A1 | 8/2009 | Leroux et al. |
| 2009/0238873 A1 | 9/2009 | Chattaraj et al. |
| 2009/0274732 A1 | 11/2009 | Hoffmann et al. |
| 2010/0003332 A1 | 1/2010 | Bae et al. |
| 2010/0015224 A1 | 1/2010 | Singh et al. |
| 2010/0196471 A1 | 8/2010 | Jain et al. |

FOREIGN PATENT DOCUMENTS

| | | |
|---|---|---|
| CA | 2 454 551 | 11/2002 |
| CA | 2 466 677 | 6/2003 |
| CA | 2468788 A1 | 6/2003 |
| CA | 2 324 493 | 2/2006 |
| CA | 2 645 855 | 9/2007 |
| CA | 2 366 702 | 5/2009 |
| CA | 2 476 496 | 12/2009 |
| CA | 2 451 379 | 4/2010 |
| WO | WO 89/04858 A1 | 6/1989 |
| WO | WO 01/12155 A1 | 2/2001 |
| WO | WO-03/047493 A2 | 6/2003 |
| WO | WO 03/051333 A1 | 6/2003 |
| WO | WO 03/103594 A2 | 12/2003 |
| WO | WO 2006/105659 A1 | 10/2006 |
| WO | WO 2009/080025 A1 | 7/2009 |
| WO | WO 2010/022497 A1 | 3/2010 |

* cited by examiner

Comparative Drug Release Profiles:
In-Vitro Dissolution: Glucophage 1000mg, Glucophage XR 1000mg, GlycoBien CR 1000mg

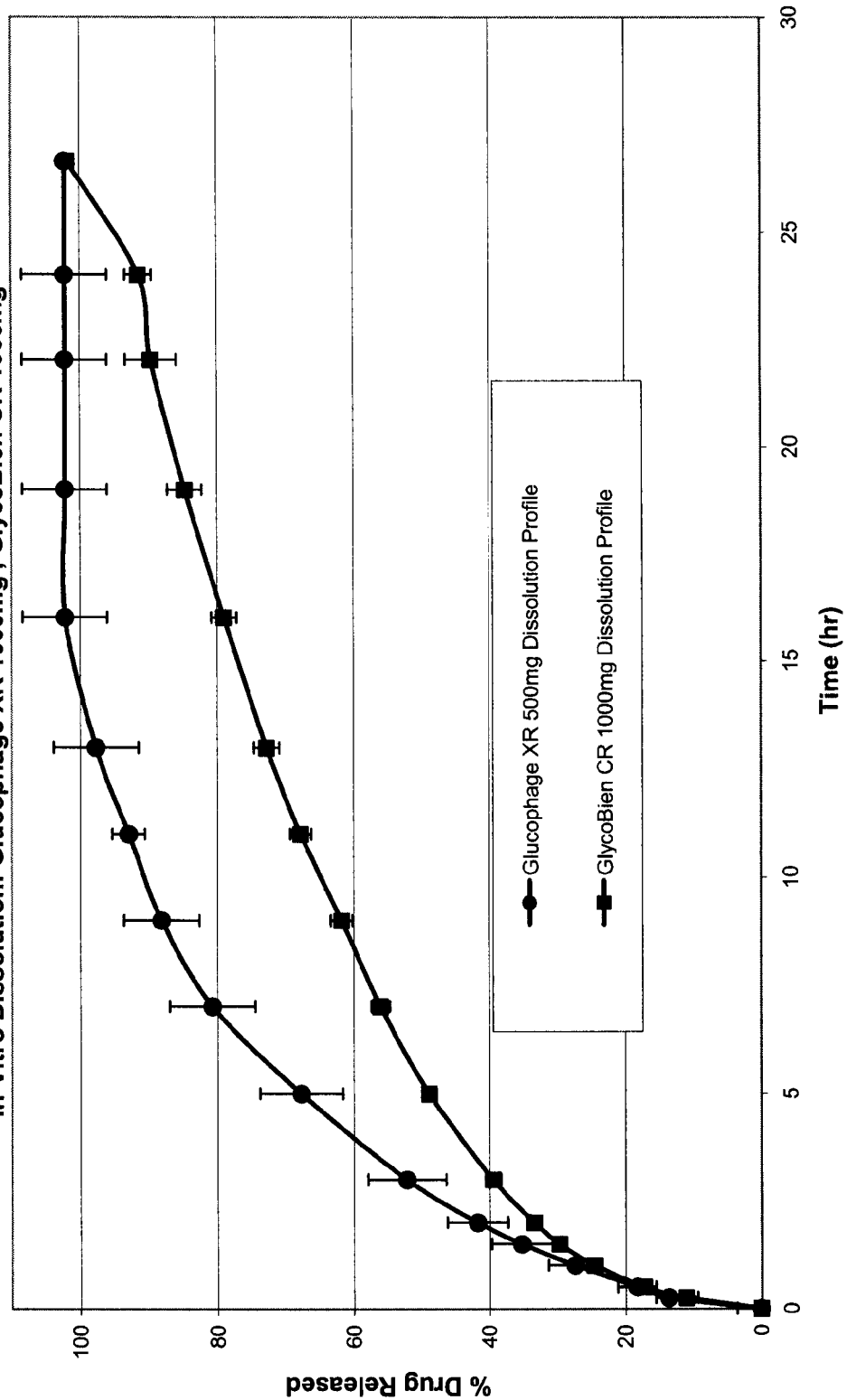

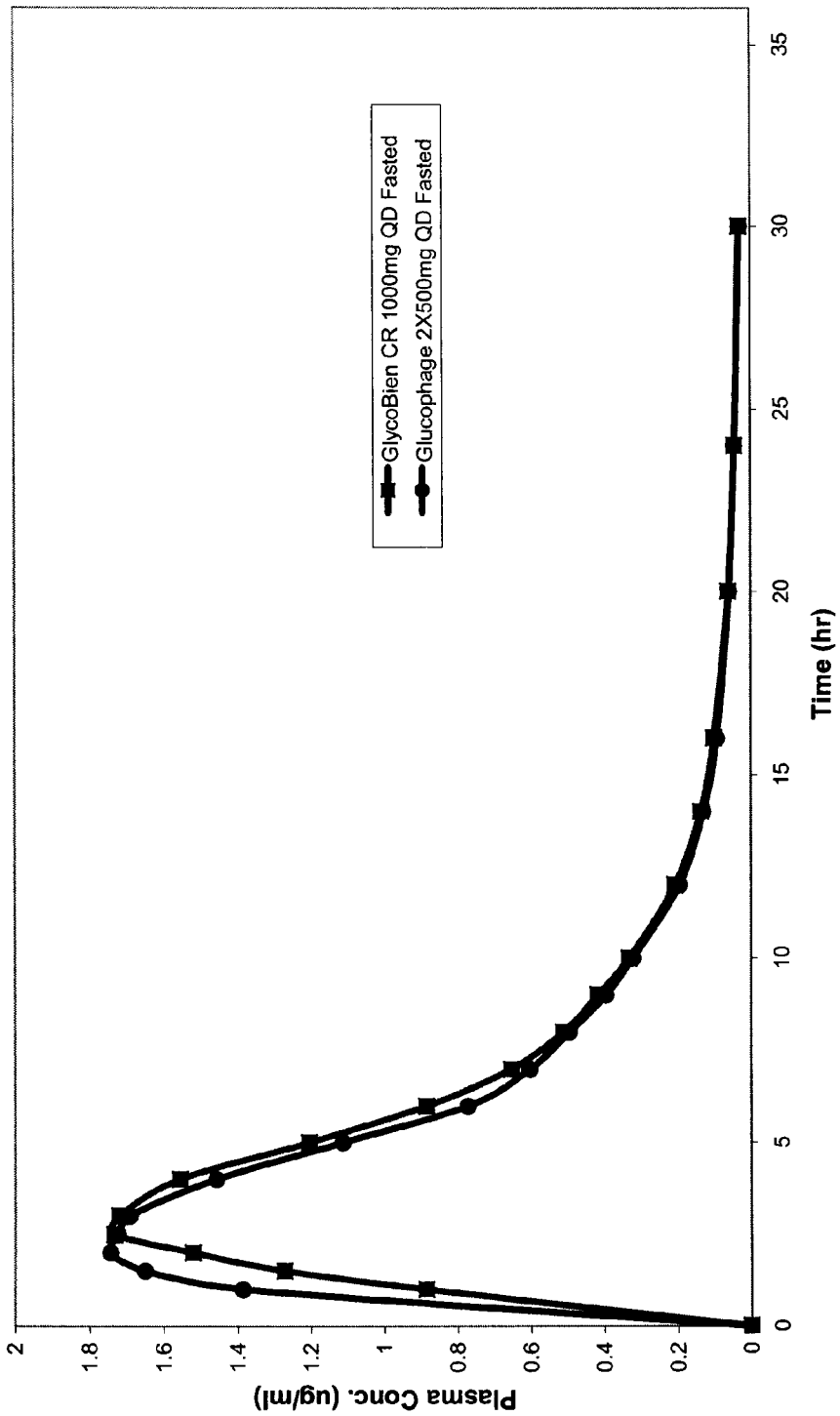

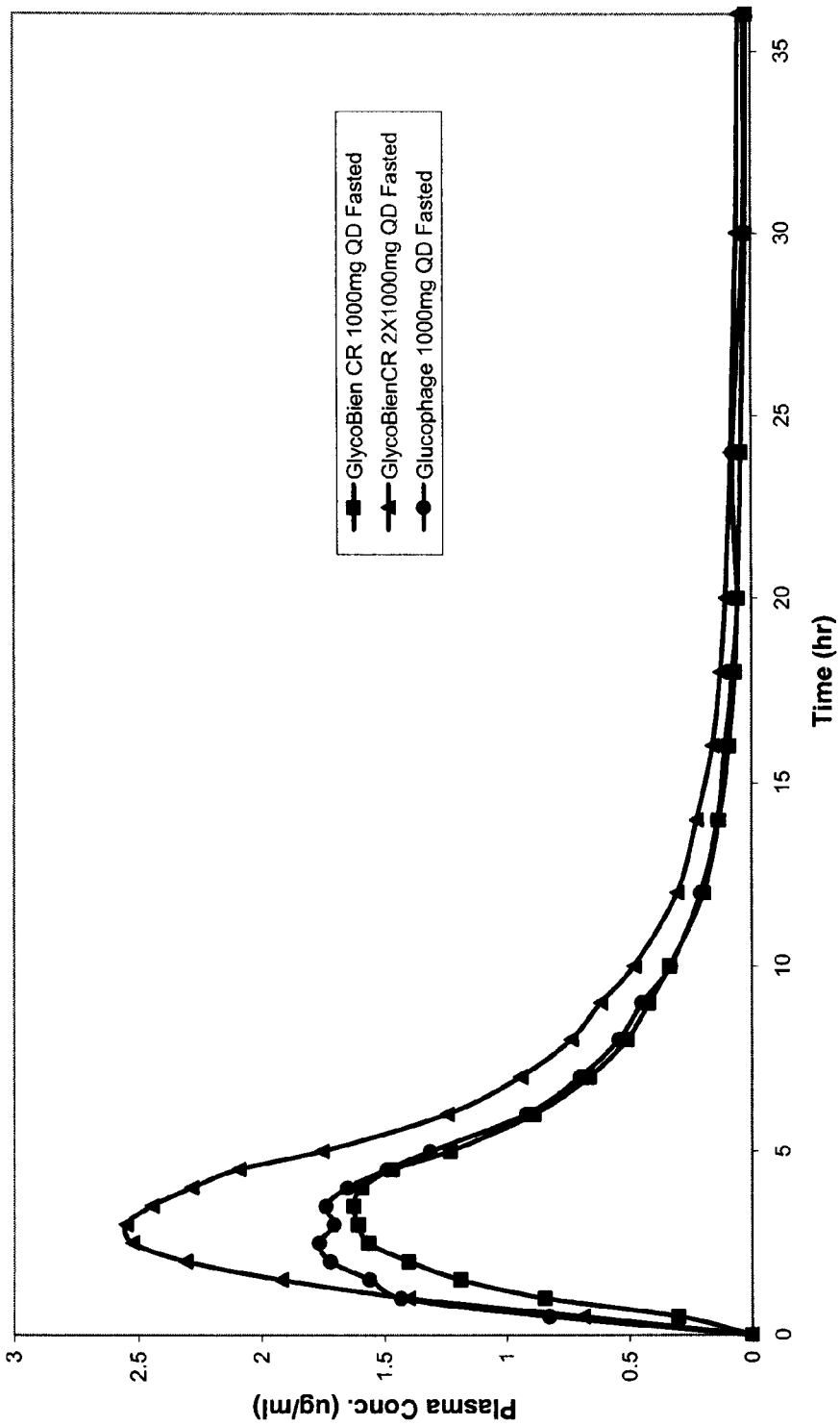

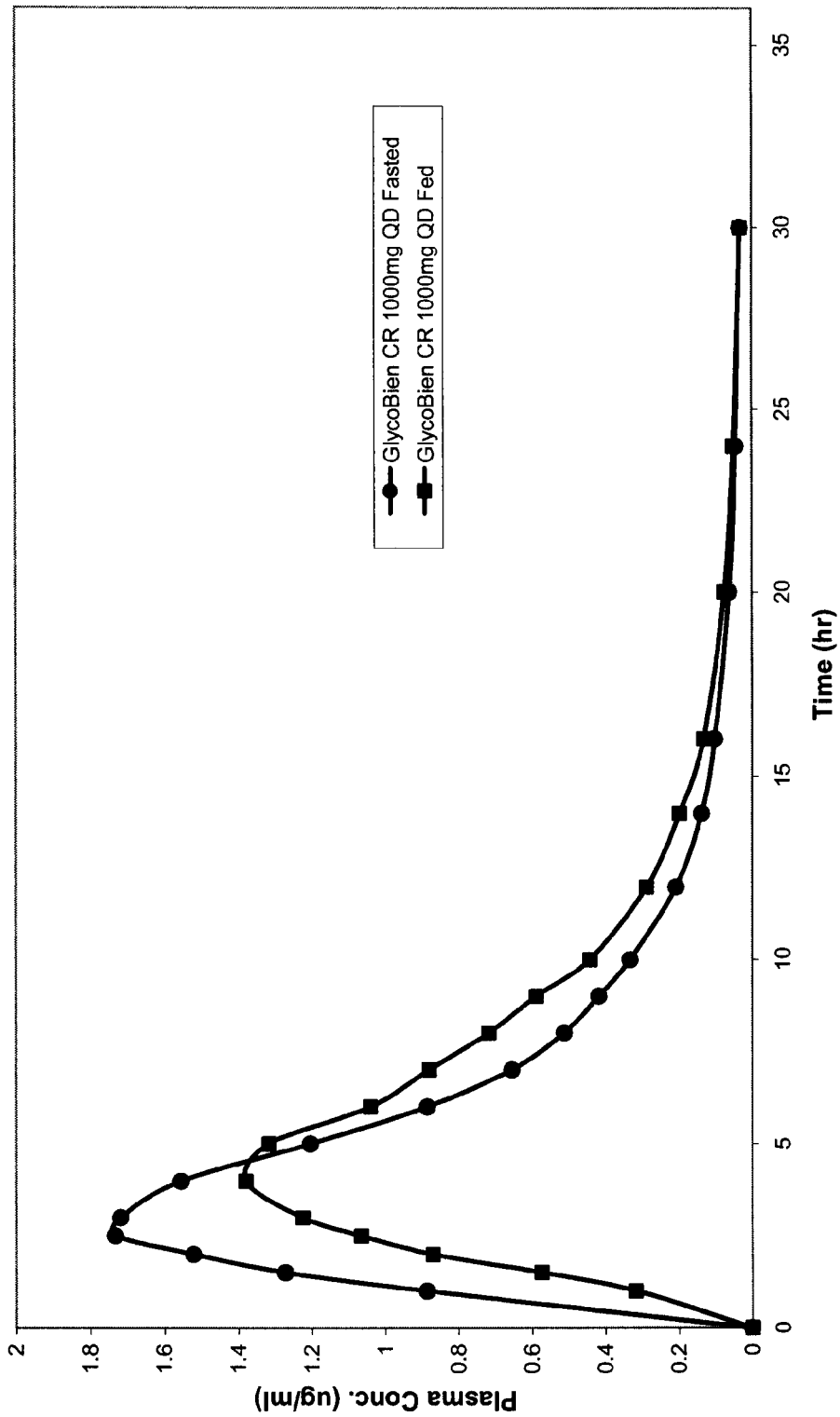

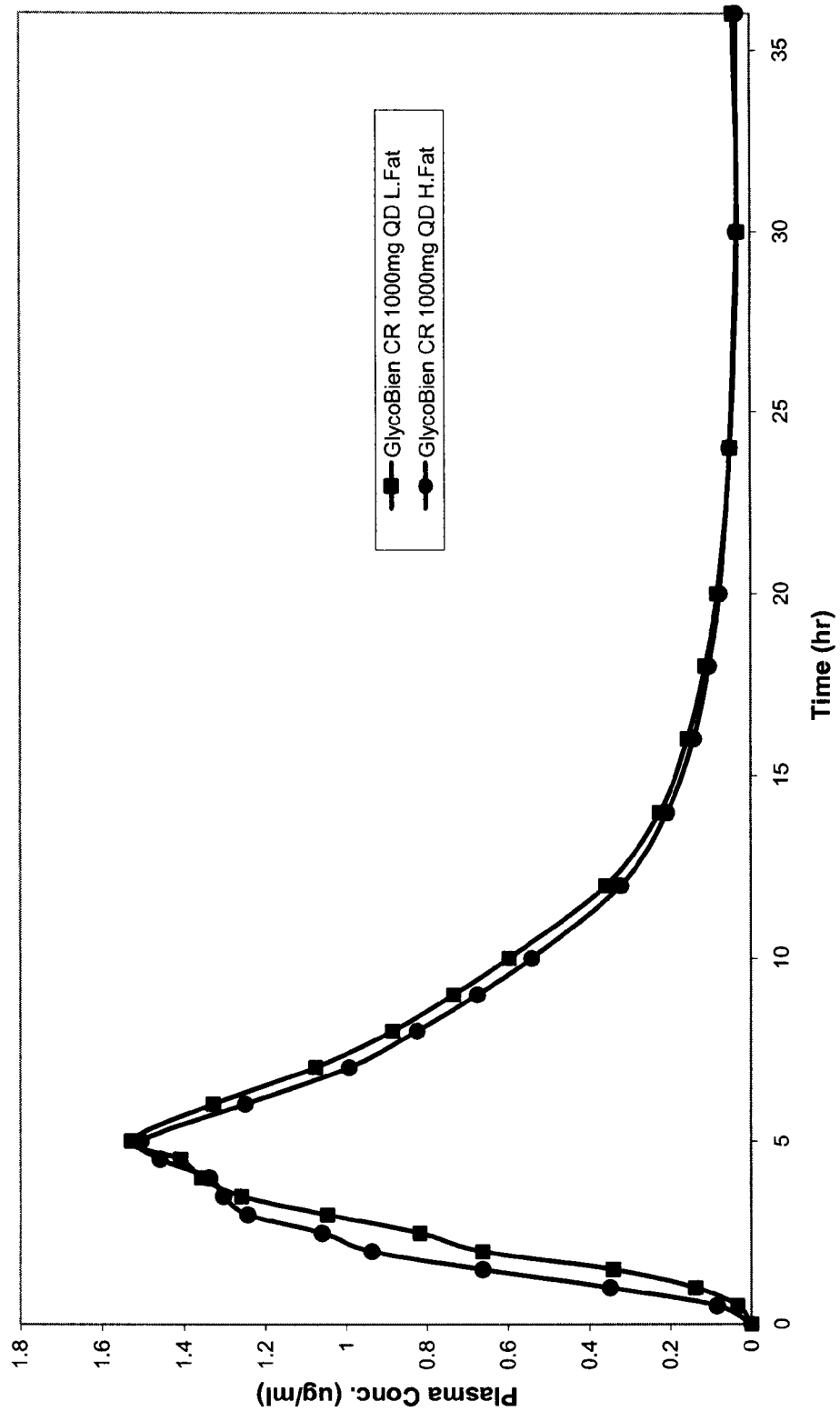

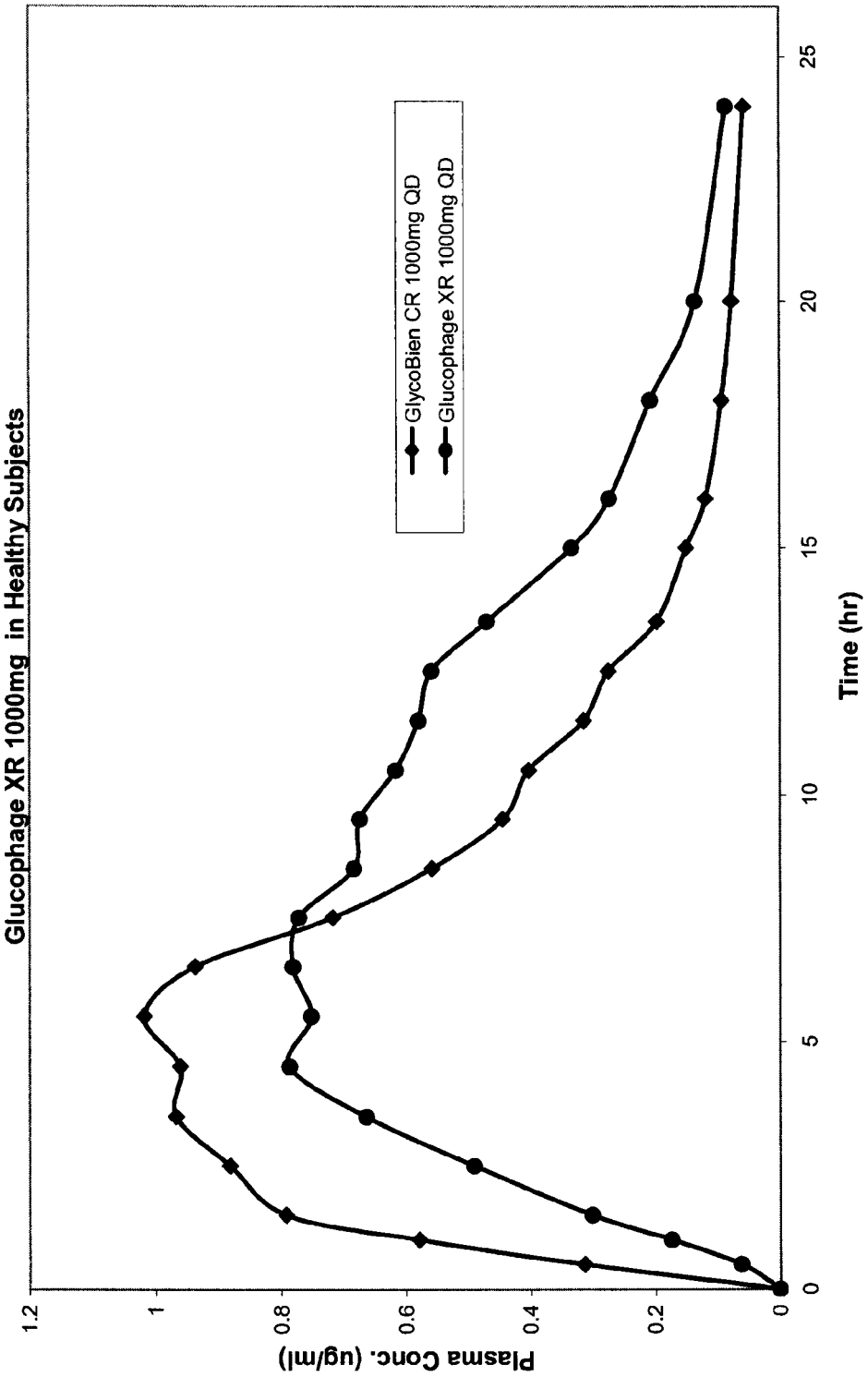

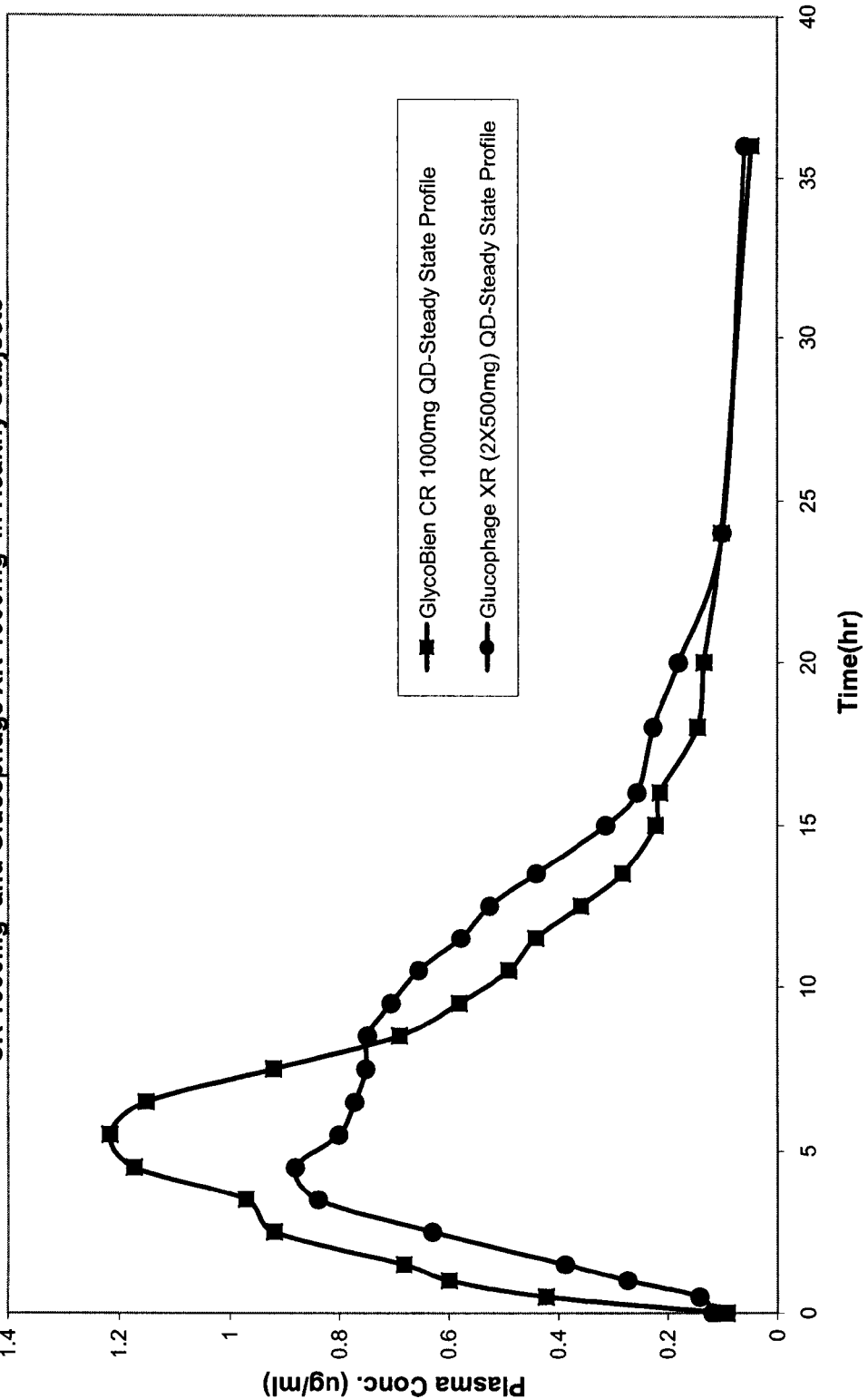

Comparative daily Postprandial Glycemic Excursions (IAUC0-24) in Healthy Subjects Fed standardized meals during Crossover treatments with Placebo, GlycoBien CR and Glucophage XR

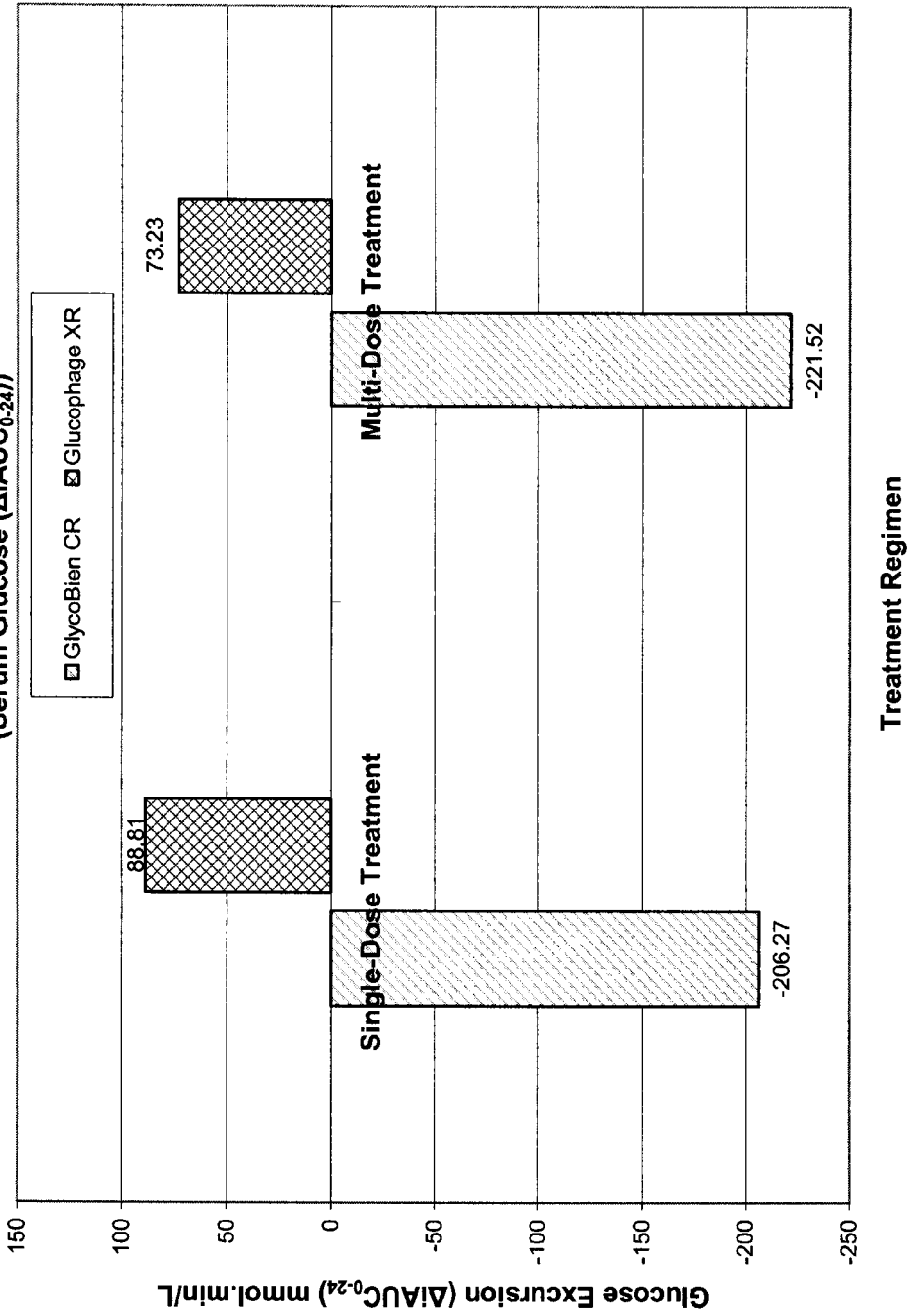

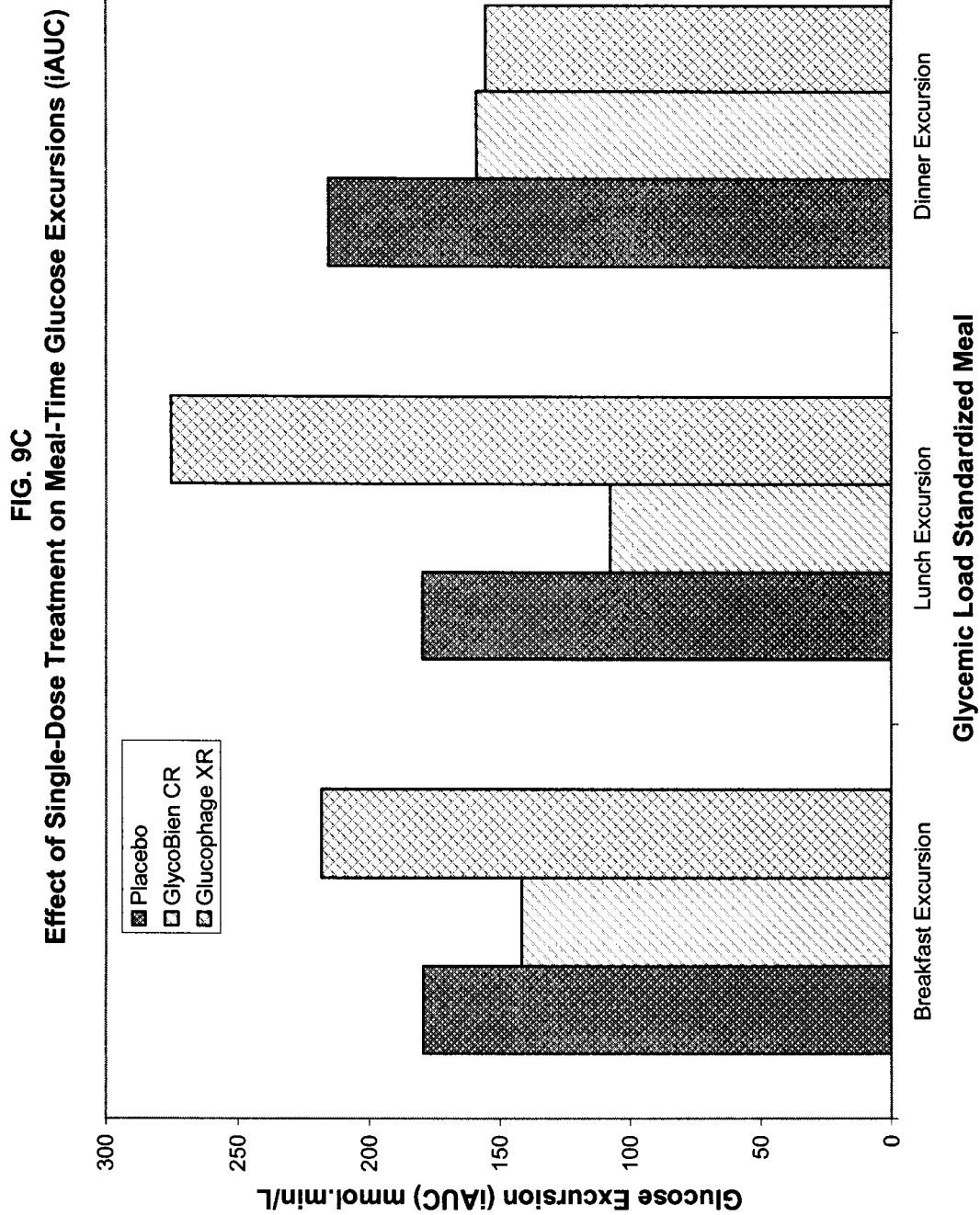

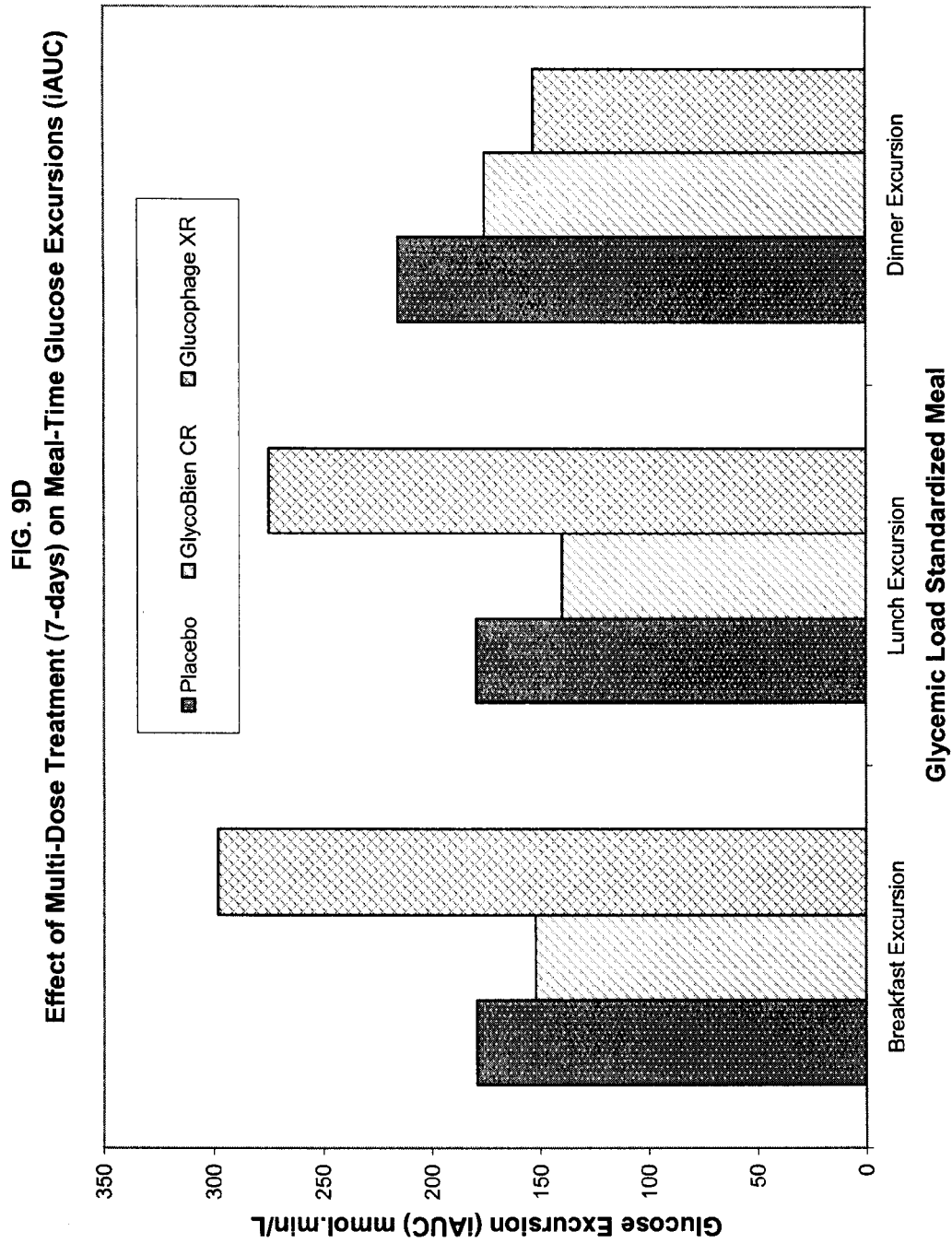

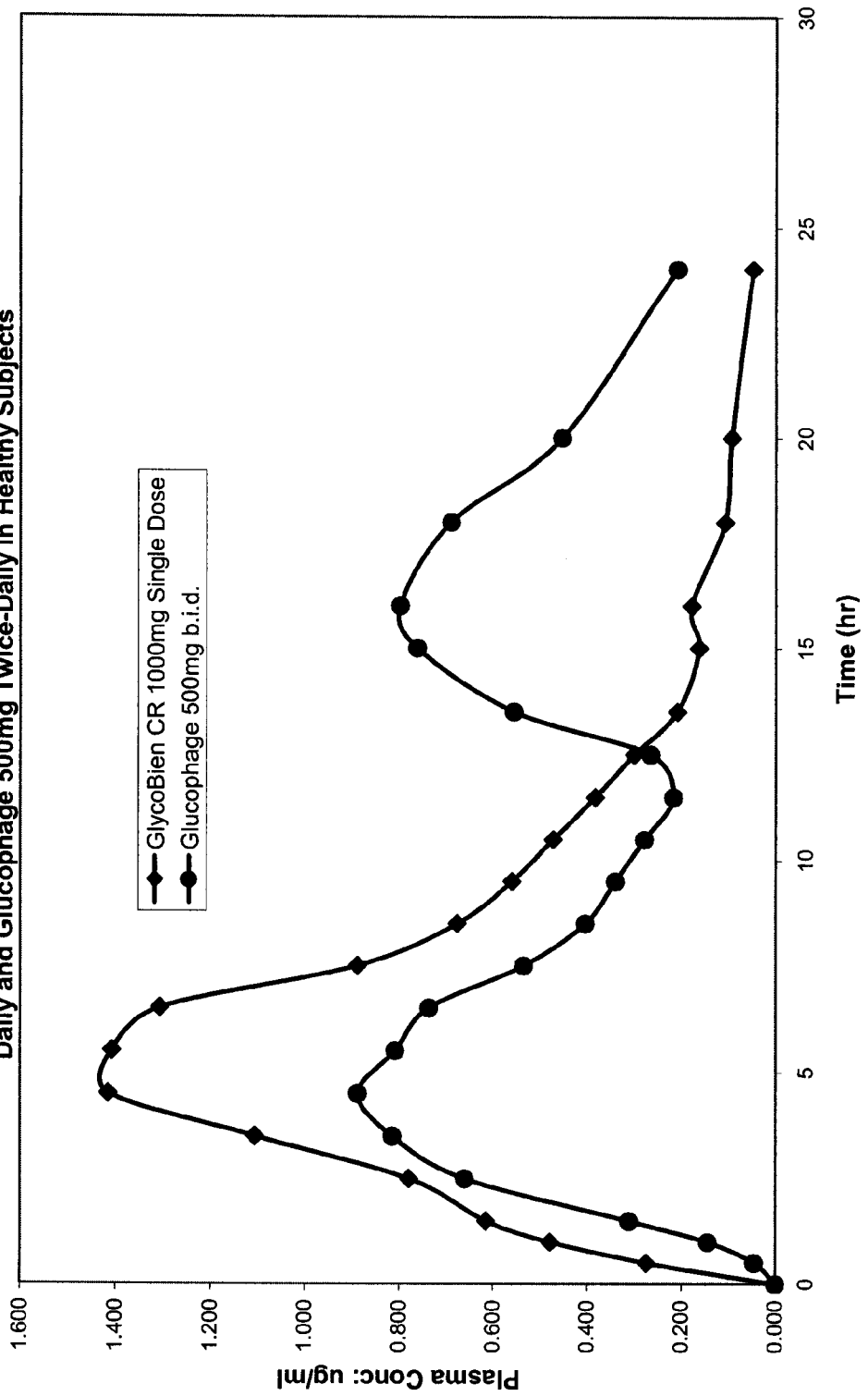

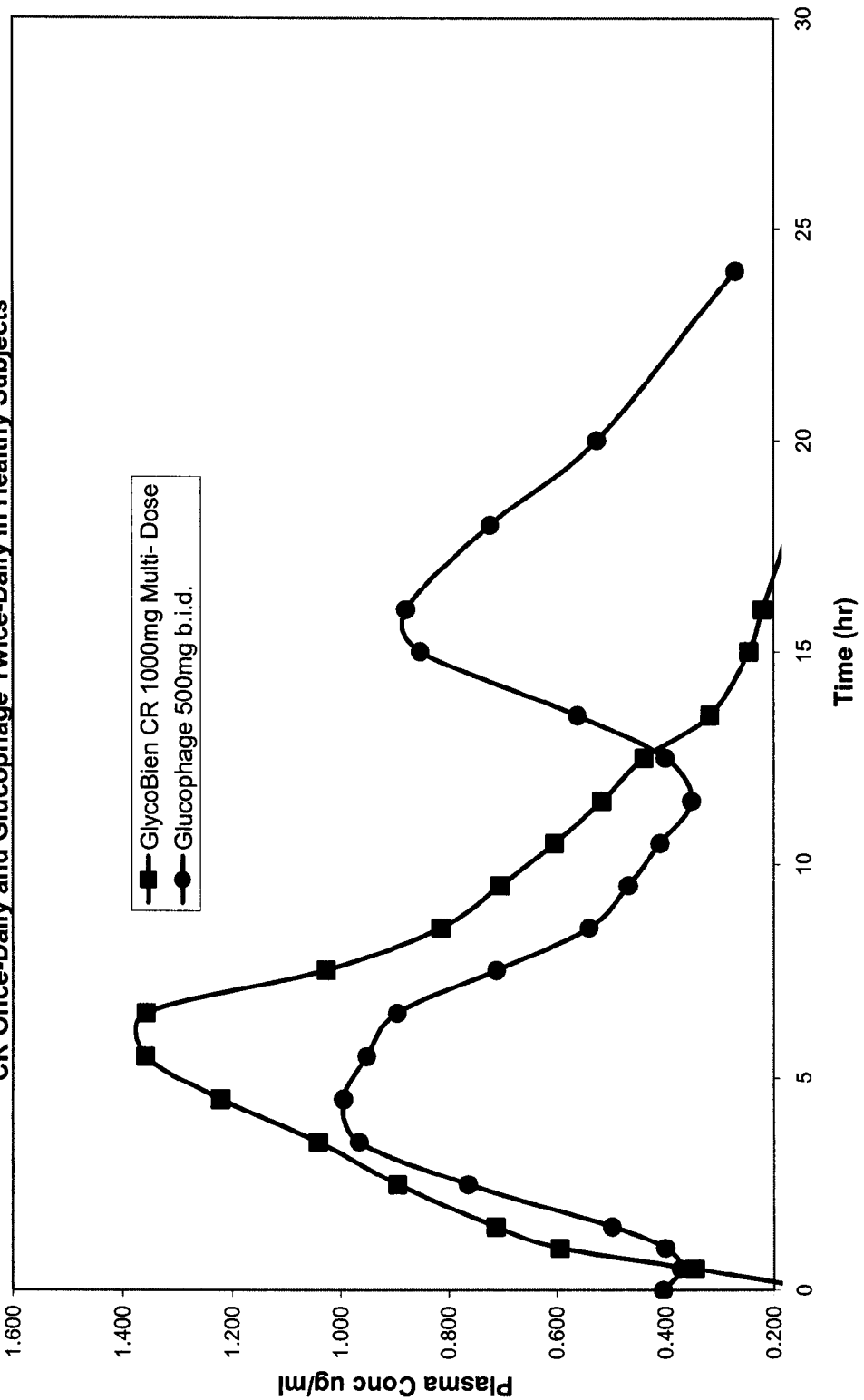

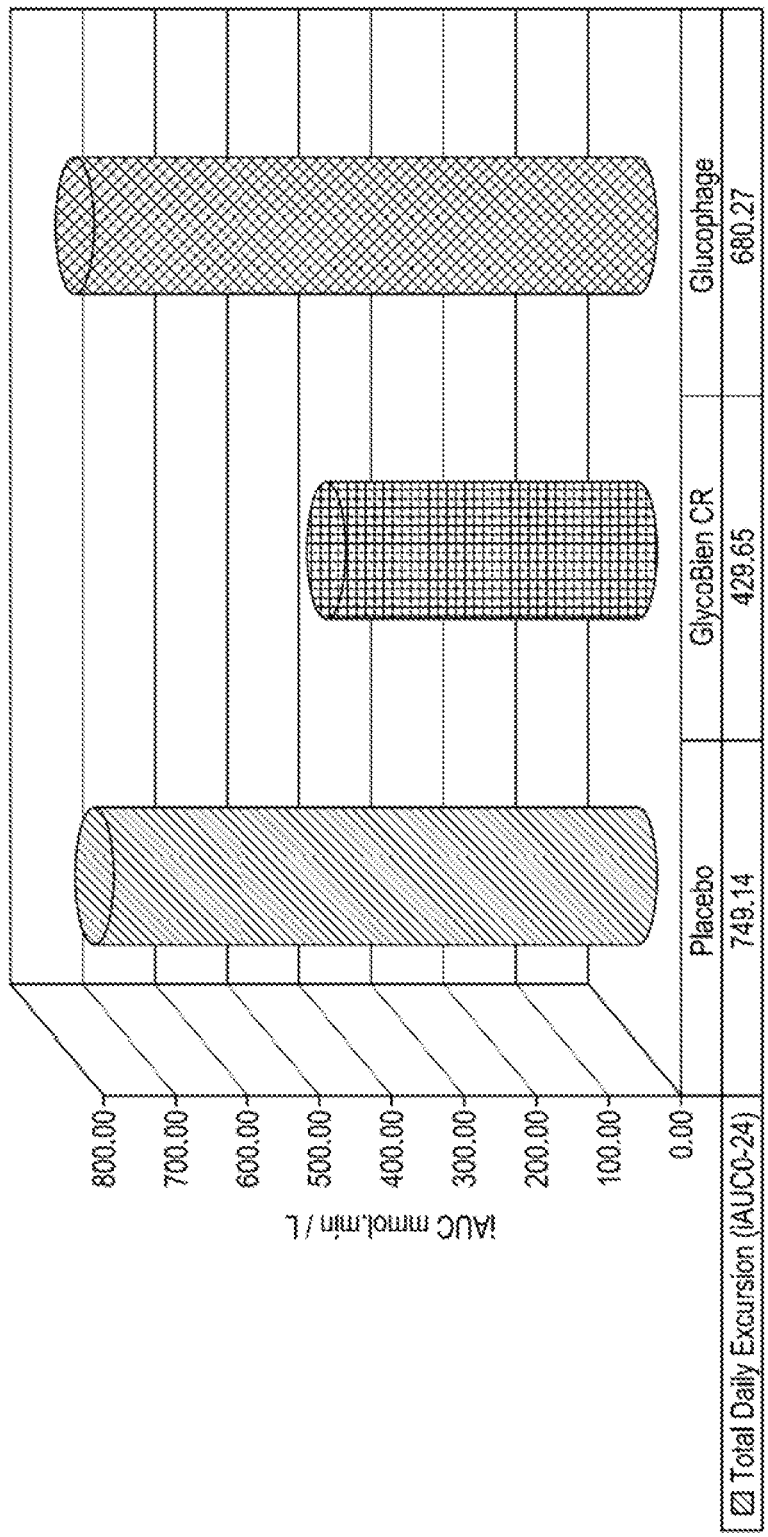

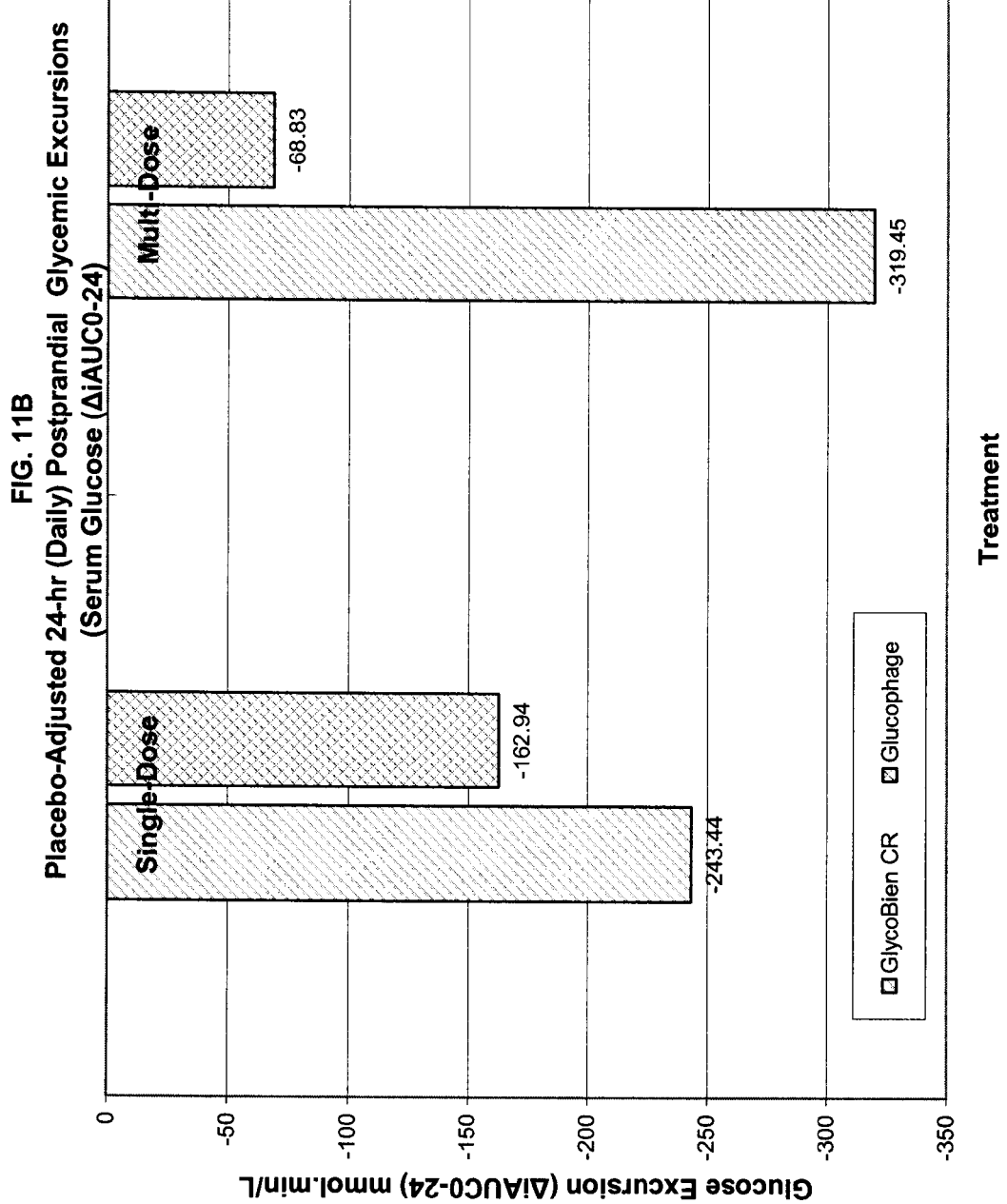

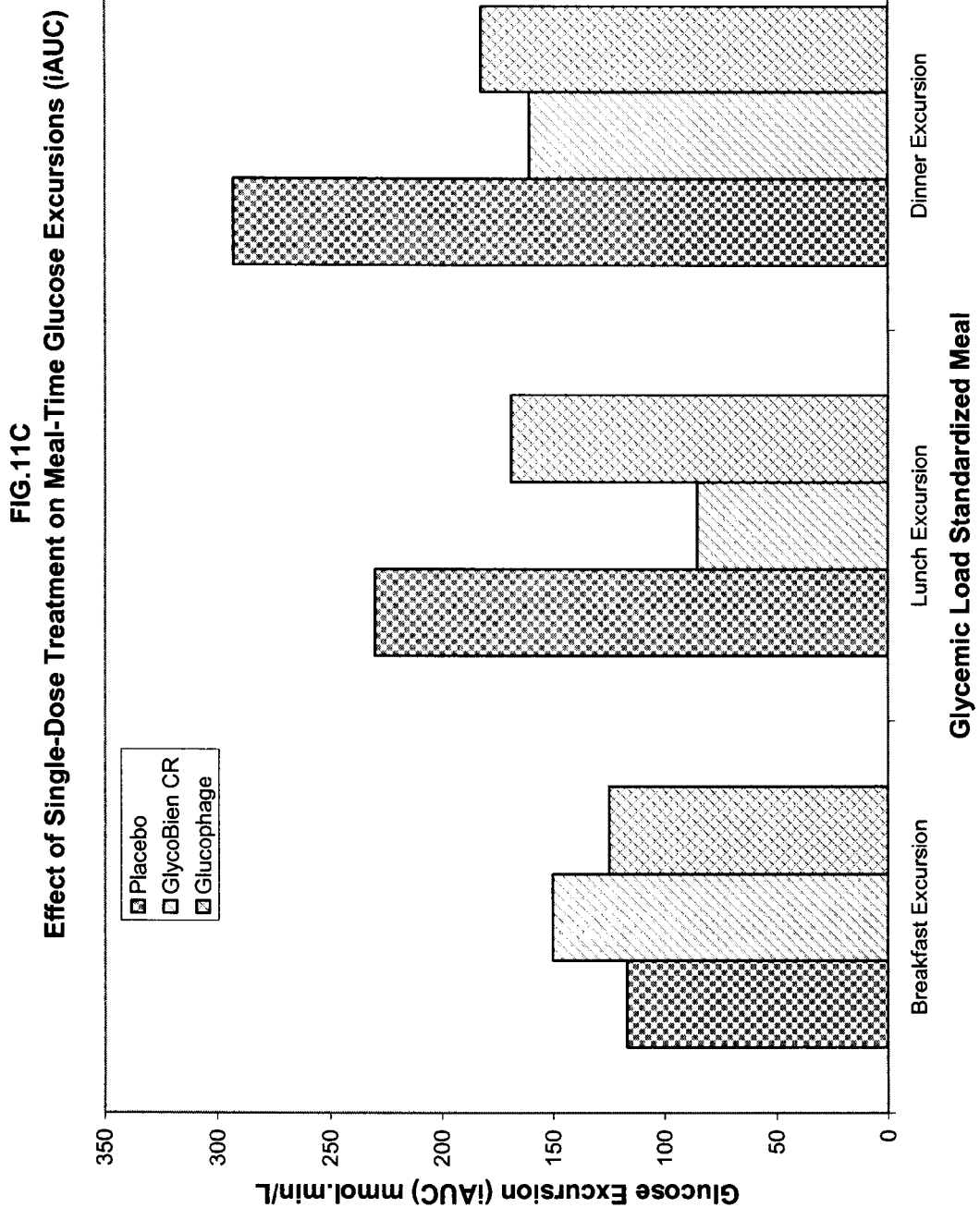

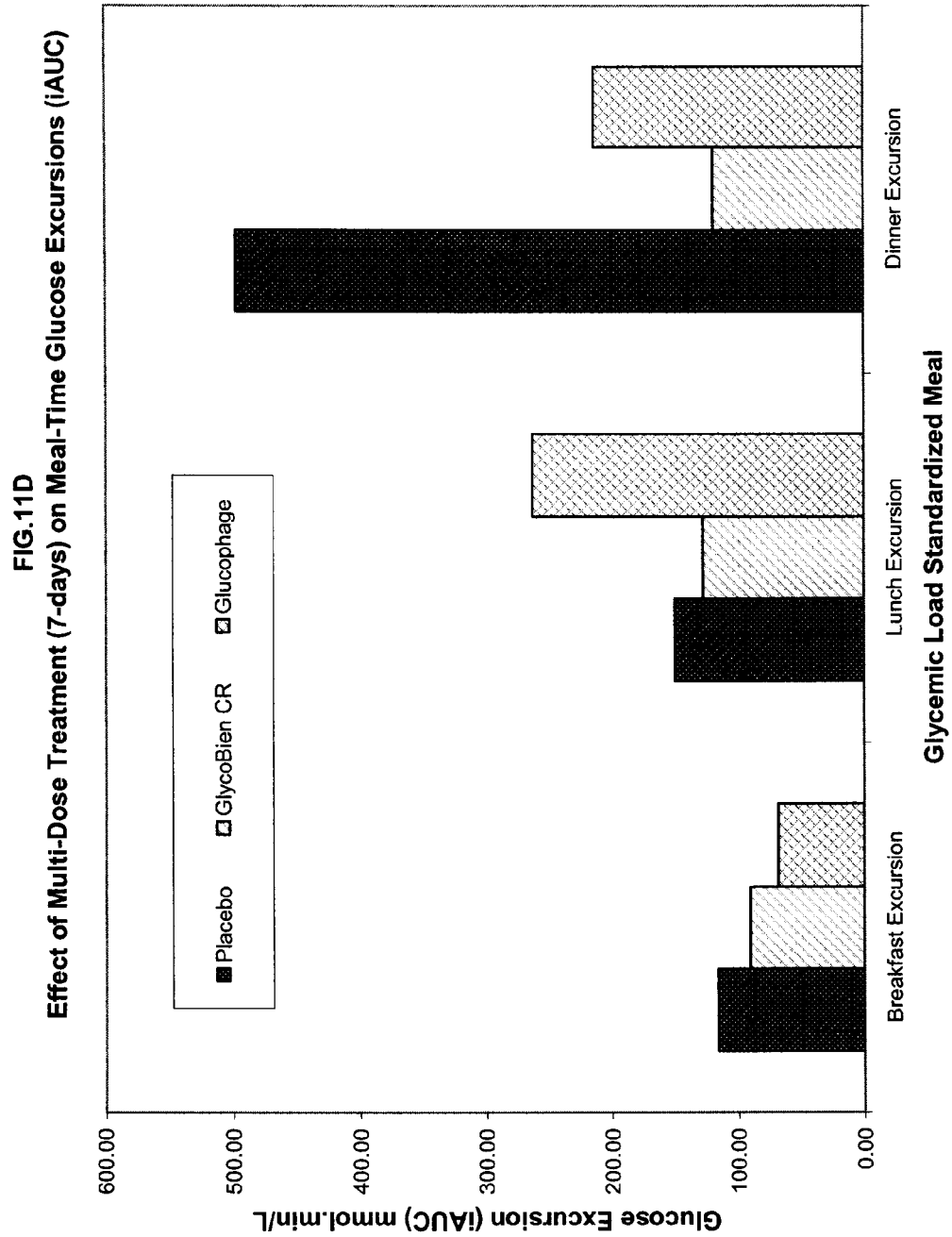

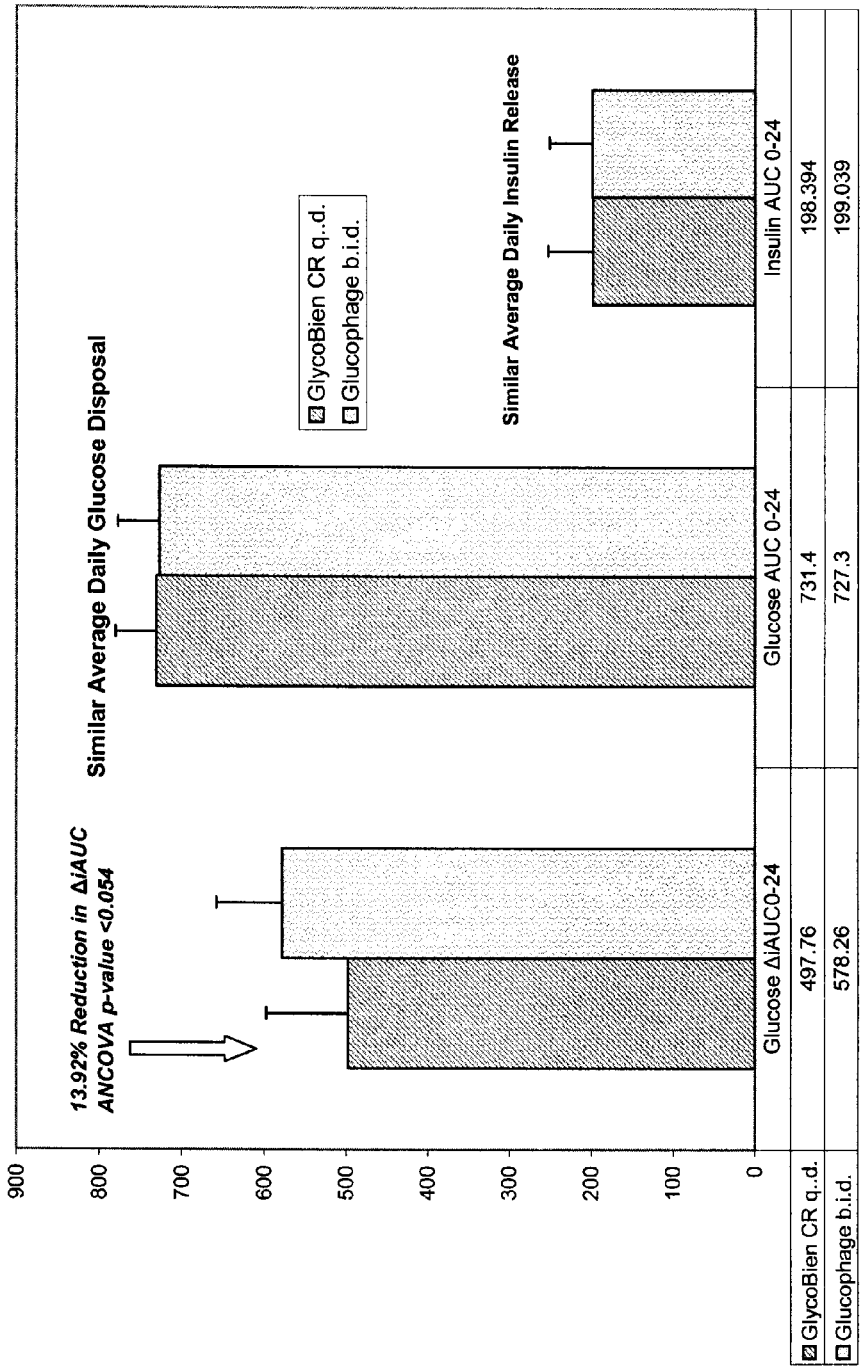

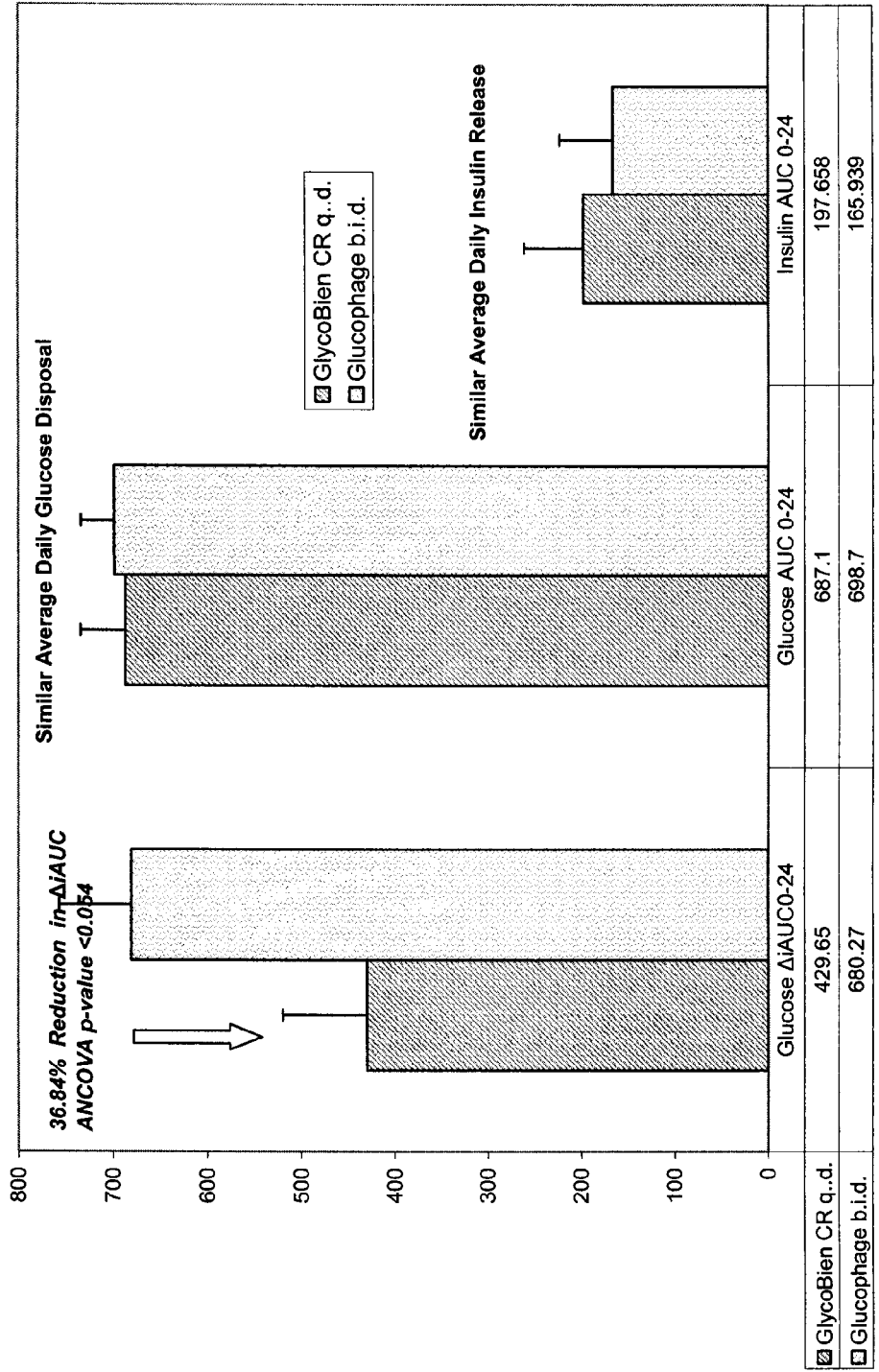

METHOD OF TREATING DYSGLYCEMIA AND GLUCOSE EXCURSIONS

CROSS-REFERENCE TO RELATED APPLICATION

This application is a National Stage entry of International Application No. PCT/CA2009/001166, filed Aug. 24, 2009, which claims priority to Canadian Application No. 2,638,240, filed Aug. 29, 2008, the entire specification, claims and drawings of which are incorporated herein by reference.

FIELD OF INVENTION

The present invention relates to treatment methods and compositions containing insulin-sensitizing oral hypoglycemic agents for reducing postprandial glucose excursions and for achieving superior blood glucose control in mammals, such as humans with insulin-related disorders or predisposed to insulin-related disorders. Specifically, the present application discloses methods that provide effective reduction of postprandial glucose excursions in non-diabetic individuals, individuals with pre-diabetes, impaired glucose tolerance, impaired fasting glucose, and patients with diabetes by improving the effectiveness and efficiency of endogenous insulin action with novel oral compositions of insulin-sensitizing oral hypoglycemic agents.

BACKGROUND OF THE INVENTION

There are two states of activity essential for normal glucose homeostasis—the absorptive or post-meal state and the basal or post-absorptive state. After a carbohydrate meal is ingested, the body's primary requirement is to maintain a normal plasma glucose level. To a large extent this glucose maintenance is accomplished by the secretion of insulin, which occurs in two main phases; an acute early phase and a secondary late phase. At the cellular level, insulin activates glucose transport and disposal pathways, with resulting storage as glycogen. Insulin secretion and glycemia suppresses hepatic glucose production (HGP), primarily by decreasing hepatic glycogenolysis. Gluconeogenesis, the other pathway by which the liver produces glucose, is also suppressed by physiologic concentrations of glucose but not by insulin.

The net effect of this homeostatic mechanism in normal individuals is that greater than 95% decrease in HGP is achieved by modest increases in plasma insulin and glucose concentrations. Insulin promotes cellular uptake of approximately 25% of the glucose load into insulin-dependent tissues-primarily muscles. The remaining 75% of the glucose load is taken up by insulin-independent tissues such as brain, splanchnic organs (liver and gut), erythrocytes, and kidneys at a rate proportional to the prevailing plasma glucose level. Adipose tissue is responsible for the disposal of less than 5% of a glucose load. Plasma glucose levels are maintained at a steady state by the liver through both glycogenolysis and gluconeogenesis. Thus, the rate of HGP is matched to glucose uptake by tissues, primarily through the action of insulin.

Diabetes mellitus, which currently afflicts at least 246 million people worldwide and expected to affect 380 million by 2025 is the fourth leading cause of global death by disease and is a group of diseases marked by high levels of blood glucose resulting from defects in insulin production, insulin action, or both.

One form of the disease is insulin-dependent diabetes mellitus (IDDM) or Type 1 diabetes and accounts for about 10% of diabetic population globally. IDDM is a result of autoimmune destruction of insulin-secreting β-cells in the pancreatic islets of Langerhans and is associated with insufficient insulin production causing metabolic changes, such as hyperglycemia, glycosuria and decreased hepatic glycogen levels. The most common form of diabetes is non-insulin dependent diabetes mellitus (NIDDM) or Type 2 diabetes, which accounts for the remaining 90% of individuals affected. Type 2 diabetes mellitus is a heterogeneous disorder characterized by two pathogenic defects, impaired insulin secretion and insulin resistance. Impaired insulin secretion leads initially to postprandial hyperglycemia, and as beta cell function declines further, fasting hyperglycemia ensues. Insulin resistance contributes further to and aggravates the fasting and postprandial hyperglycemia It is well established in recent studies (Arch Inter Med. 2003; 163:1306-1316) that elevated glucose concentrations are an independent and clinically significant risk factor for cardiovascular disease in non-diabetic and diabetic individuals.

In a healthy individual, the basal blood glucose level is relatively constant from day to day because of an intrinsic feedback loop. Any tendency for the plasma glucose concentration to increase is counterbalanced by an increase in insulin secretion and a suppression of glucagon secretion, which regulate hepatic glucose production (gluconeogenesis and release from glycogen stores) and tissue glucose uptake to keep the plasma glucose concentration constant.

If an individual is stressed, gains weight or become insulin resistant for any other reason; blood glucose levels will increase, resulting in increased insulin secretion to compensate for the insulin resistance. Therefore, the glucose and insulin levels are modulated to minimize changes in these concentrations while relatively normal production and utilization of glucose are maintained.

Impaired glucose tolerance (IGT) characterized by glycemia between normal and overtly diabetic levels is a major risk factor for the development of NIDDM and is associated with an increased risk for macrovascular disease. Over 50% of potential NIDDM cases are undiagnosed and IGT is more prevalent amongst this population (National Diabetes Data Group and WHO criteria).

Insulin secretion in response to meals is multiphasic; a main biphasic mode in response of carbohydrate meals has been classified as first-phase or acute insulin response and defined as the initial burst of insulin released in the first 5-10 min after the pancreatic β cell is exposed to a rapid increase in glucose (or other secretagogues), and a second-phase insulin secretion which rises more gradually and is directly related to the degree and duration of the stimulus. Other modes of insulin release that have been identified include: 1) basal insulin secretion characterizing release in the post-absorptive state; 2) the cephalic phase of insulin secretion evoked by the sight, smell, and taste of food (before any nutrient is absorbed by the gut) and is mediated by pancreatic innervation; and finally, a third phase of insulin secretion that has only been described in vitro. During these stages, like many other hormones, insulin is secreted in a pulsatile fashion, resulting in oscillatory concentrations in peripheral blood.

Adequate glucose control is achieved in healthy individuals when the pancreatic β-cells generate an early response to a meal-like glucose exposure that rapidly elevates serum insulin both in the portal circulation and in the periphery. Conversely, in Type 2 diabetics, defective β-cells, which have an impaired first-phase insulin response, generate a sluggish response to the meal-like glucose exposure leading to post-meal hyperglycemia.

Postprandial hyperglycemia is now known to be a prominent and early defect in the etiology of Type 2 diabetes. It is also known and established in numerous studies that post-meal glucose excursions or postprandial hyperglycemia is associated with increased cardiovascular mortality in Type 2 diabetes (*Diabetologia* 39: 1577-1583; *the DIS group* 1996 *Risk factors for myocardial infarction and death in newly detected NIDDM: the Diabetes Intervention Study,* 11-*year follow-up;* Lancet 354:617-621*DECODE Study Group, European Diabetes Epidemiology Group* 1999 *Glucose tolerance and mortality: comparison of WHO and American Diabetes Association diagnostic criteria., Diabetes study.* Diabetes Care 22:920-*A* 1999 *Impaired glucose tolerance is a risk factor for cardiovascular disease, but not impaired fasting glucose: the Fungata* 924). In addition postprandial hyperglycemia has also been identified not only as a risk factor of cardiovascular disease among apparently healthy individuals but also directly linked to endothelia dysfunction, mortality in middle-aged non-diabetic males, (*Circulation* 2002:106:1211-1218 Ceriello A et al., *Diabet Med.* 2004, 21(2*VnI-S.* Ceriello A et al, and *Diabetes Care* 1998, 21(3): 360-7. Balkau et al.), and as an independent risk factor for increased carotid intima-media thickness in non-diabetic individuals (*Arch Intern Med*. (2004) 164:2147-2155. Levitan E B, et al., *Atherosclerosis*. (1999) 144(1):229-35, Hanefeld M et al.). The role of post-prandial glucose excursions, i.e. the incremental blood glucose response to exogenous glucose intake, in the development of microvascular complications in diabetes is also well established (*JAMA* 2002; 287:2414-23; *The glycemic index-physiological mechanisms relating to obesity, diabetes and cardiovascular disease*. Ludwig D S., and *Arch Inter Med* 2003; 163:1306-16; *Clinical significance, pathogenesis, and management of postprandial hyperglycemia;* Gerich J E.)

While conventional diabetes management guidelines recommends and advises monitoring of fasting plasma glucose (FPG) and glycated hemoglobin (HbA1c) concentrations as a means of evaluating overall glycemic control, it is known that such FPG determinations does not provide information about the contribution of the postprandial rise in glucose levels to overall glycemic control. In fact HbA1c does not provide information relevant to the daily oscillations in blood glucose levels because it only represents the average glucose levels during the previous 2 to 3 months.

In addition, postprandial hyperglycemia occurs in approximately 40% of subjects who have achieved the recommended hemoglobin HbA1c targets (<7%) and in approximately 10% of diabetic subjects who have achieved normal fasting blood glucose levels (*Diabetes Care* 24:1734-1738 2001; *Post challenge hyperglycemia in a national sample of U.S. adults with Type* 2 *diabetes;* Erlinger T P, Brancati F L.). Post-meal glucose spikes are also estimated to account for 54% of glucose increments in diabetic subjects (*Diabetes Care* 25:737-741 2002 *Morning hyperglycemic excursions: a constant failure in the metabolic control of non-insulin-using patients with Type* 2 *diabetes*; Monnier L, Colette C, Rabasa-Lhoret R, Lapinski H, Caubel C, Avignon A, Boniface H) and are highly correlated with HbA1c (*Diabetes Care* 20:1822-1826 1997 *Non-fasting plasma glucose is a better marker of diabetic control then fasting plasma glucose in Type* 2 *diabetes* Avignon A, Radauceanu A, Monnier L)

In today's modern society with a breakfast, lunch, snack and dinner culture, a large part of the day is spent in the postprandial state which could lasts up to about 20 hours per day. The postprandial state has an estimated duration of 2-8 hours after each meal, depending on the nutrient content and the parameter measured (*N Engl J Med* 327:707-713 1992 *Carbohydrate metabolism in non-insulin-dependent diabetes mellitus*. Dinneen S, Gerich J E, Rizza R, *Diabetes* 37:1020-10241988 *Measurement of plasma glucose, free fatty acid, lactate, and insulin for* 24 *h in patients with NIDDM;* Reaven G M, Hollenbeck C, Jeng C Y, Wu M S, Chen Y D). Most people are more often in a postprandial state rather than in a truly fasting state. Wide fluctuations in plasma glucose levels may occur throughout the day with high values 1 to 2 hours after a meal and low values before the next meal. Postprandial hyperglycemia is predominantly due to loss of insulin secretion in the first 30 min after eating (*Diabetes Care* 7:491-502 1984 *Pathophysiology of insulin secretion in non-insulin-dependent diabetes mellitus* Ward W K, Beard J C, Halter J B, Pfeiffer M A, Porte D.) This β-cell defect results in inadequate suppression of hepatic glucose production and subsequent late hyperinsulinemia (*Diabetes* 48:99-105, 1999 *Restoration of early rise in plasma insulin levels improves the glucose tolerance of Type* 2 *diabetic patients*; Bruttomesso D, Pianta A, Mari A, Valerio A, Marescotti M, Avogaro A, Tiengo A, Del Prato S)

Thus, it is prudent and more useful to assess postprandial glucose levels in the monitoring of overall glycemic control. The postprandial glucose levels may more closely represent the metabolic processes involved in the pathogenesis of Type 2 diabetes—insulin resistance, increased hepatic glucose output, and impaired insulin secretion.

In a normal individual, the consumption of a meal induces a burst release of insulin, generating a rapid spike in serum insulin concentration that then decays relatively quickly. This early-phase insulin response is responsible for the suppression of endogenous glucose release from the liver. Homeostatic mechanisms then match subsequent insulin secretion (and serum insulin levels) to the glucose load. This is observed as a slow decay of modestly elevated serum insulin levels back to baseline in what is referred as second-phase kinetics.

Increasingly, evidence indicates that it is the early relatively rapid insulin response following glucose ingestion that plays the critical role in the maintenance of postprandial glucose homeostasis. An early surge in insulin concentration acts to limit initial glucose excursions, mainly through the inhibition of endogenous glucose production. Therefore, the induction of a rapid insulin response in a diabetic individual is expected to produce improved blood glucose homeostasis. In point of fact, Type 2 diabetics typically exhibit a delayed response to increases in blood glucose levels. While normal individuals usually begin to release insulin within 2-3 minutes following the consumption of food, Type 2 diabetics may not secrete endogenous insulin until blood glucose begins to rise significantly, with second-phase kinetics, which produces a slow rise and extended plateau in insulin concentration.

As a result of the defective first-phase "burst" insulin release, endogenous glucose production is not inhibited and continues well after meal consumption and the patient imminently experiences elevated blood glucose levels or hyperglycemia. As the disease progresses, the demands placed on the pancreas further degrades its ability to produce insulin and control of blood glucose levels gradually deteriorates. If unchecked, the disease can progress to the point that the deficit in insulin production approaches that typical of fully developed Type 1 diabetes. However, Type 1 diabetes can involve an early "honeymoon" stage, following an initial crisis, in which insulin is still produced but defects in release similar to early Type 2 diseases are exhibited.

While the relevance of insulin secretion abnormalities in the pathogenesis of Type 2 diabetes mellitus have been extensively debated, a clear consensus reached is that to fulfill its pivotal role in regulating glucose metabolism, insulin secretion must not only be quantitatively appropriate, but also possess qualitative, dynamic features that optimize insulin action on target tissues.

Furthermore, several clinical observations have confirmed that exaggerated post-breakfast hyperglycemia manifesting as high plasma glucose excursions over morning periods seems to be a permanent failure in non-insulin-using patients with Type 2 diabetes, regardless of their body weight, calorific and nutrient content of their meals, biological (HbA1c), therapeutic and pathophysiological (residual β-cell function) status. This circadian pattern of glucose response to meals is most likely due to impaired hepatic insulin sensitivity resulting in inadequate suppression of hepatic glucose output in the morning hours. In the same studies, it was demonstrated that hepatic glucose production peaks after an overnight fast and declines progressively to reach a nadir in the afternoon in Type 2 diabetes patients (*Diabetes* 45:1044-1050, 1996 *Evidence for a circadian rhythm of insulin sensitivity in patients with NIDDM caused by cyclic changes in hepatic glucose production* Boden G, Chen X, Urbain J L.). A similar mechanism is thought to cause fasting hyperglycemia due to the dawn phenomenon (*N Engl J Med* 310:746-750 1984 *The "dawn phenomenon"—a common occurrence in both non-insulin-dependent and insulin-dependent diabetes mellitus*, Bolli G B, Gerich J E).

Thus, there is a great need for a safe, effective agent for decreasing postprandial glucose excursion in apparently healthy individuals, overweight persons, obese persons or persons with impaired glucose tolerance to prevent risk of cardiovascular disease.

Also, there is a great need for a safe, effective agent for reducing postprandial glucose excursion and postprandial hyperglycemia in Type 2 diabetic subjects to reduce risk of cardiovascular disease and other complications associated with postprandial glucose excursions.

Type 1 diabetic patients are currently treated with insulin, while the majority of Type 2 diabetic patients are treated either with agents that stimulate β-cell function or with agents that enhance the tissue sensitivity of the patients towards insulin. These agents are typically taken orally and thus collectively referred to as oral hypoglycemic agents. The most common insulin sensitizing oral hypoglycemic agents are the glitazones (e.g. pioglitazone and rosiglizatone) and the biguanides (e.g. buformin and metformin).

The currently available oral hypoglycemic agents and other insulinotropic agents while effective in lowering glucose levels in blood are not completely effective in overcoming the hepatic insulin resistance that not only magnifies post-breakfast glycemic excursions but also typically contributes to post-lunch and post-supper glycemic excursions. Among the safe, effective oral hypoglycemic agents, the guanidine derivative metformin still remains the most commonly prescribed oral anti-diabetic drug indicated for use in the management of Type 2 diabetes.

Metformin is a hepato-selective insulin sensitizer, which successfully lowers fasting blood glucose and % HbA1$_C$ and does not cause hypoglycemia or hyperinsulinemia. Although it has been in clinical use for over three decades, the known therapeutic profile has been largely based on treatment from conventional immediate release formulations that require administration two or three times daily and more recently extended release formulations that allow for a once-daily administration. The effectiveness of these formulations has been based principally on lowering glycated hemoglobin (HbA1$_C$) and fasting blood glucose. Since HbA1$_C$ is a post-translational modification formed by slow non-enzymatic attachment (glycation) of glucose to adult hemoglobin (HbA$_0$), the degree of hemoglobin A1C can be used as a measure of average glycemia over the preceding 2 to 3 months and has been adopted in clinical practice as the gold standard for assessment of long-term glycemic control.

U.S. Pat. No. 3,174,901 discloses the biguanide antihypertensive agent metformin. The immediate release formulation in the form of the hydrochloride salt is currently marketed in the U.S. under the trade name Glucophage® tablets by Bristol-Myers Squibb Co. Each Glucophage® tablet contains 500, 850 or 1000 mg of metformin hydrochloride. There is no fixed dosage regimen for the management of hyperglycemia in diabetes mellitus with Glucophage®. The dosage of Glucophage® is individualized on the basis of both effectiveness and tolerance, while not exceeding the maximum recommended dose of 2550 mg per day. However, being a short acting drug, metformin requires twice-daily (b.i.d.) or three-times-a-day (t.i.d.) dosing. Adverse events associated with metformin use are often gastrointestinal in nature (e.g., anorexia, nausea, vomiting and occasionally diarrhea, etc.). These adverse events may be partially avoided by reducing the initial and/or maintenance dose or using an extended release dosage form.

U.S. Pat. No. 6,660,300 discloses compositions and techniques used to provide controlled and extended-release pharmaceutical dosage forms of metformin in order to provide a once-daily therapy and reduce the incidence of adverse events associated with the immediate release counterparts. It is reported in the 50$^{th}$ Edition of the Physicians' Desk Reference, copyright 1996, p. 753, that "food decreases the extent and slightly delays the absorption of metformin delivered by the Glucophage® dosage form. This decrease is shown by approximately a 40% lower peak concentration, a 25% lower bioavailability and a 35-minute prolongation of time to peak plasma concentration following administration of a single Glucophage® tablet containing 850 mg of metformin hydrochloride with food compared to the similar tablet administered under fasting conditions".

Methods of producing extended release metformin dosage forms, herein referenced by U.S. Pat. Nos. 6,660,300; 6,099,862; 6,340,475 and 6,488,962 have taught that it is possible to provide an extension of metformin release by prolonging the residence time in the upper gastro-intestinal tract. These prior art dosage forms have in one way or another provided for prolonged gastric residence as a plausible mechanism of extending release of metformin by essentially combining a mechanism that resists normal gastric transit times for solid materials and the physiological effect, on absorption, of prolonged gastric residence in the fed state and more preferably in the high-fat fed state.

Studies by Vidon et al (*Diabetes Res Clin Pract.* 1988 Feb. 19; 4 (3):223-9 3359923) strongly suggest that the delivery process was the rate-limiting factor for metformin absorption from the gastro-intestinal tract and that there is permeability limited absorption of metformin. The orally administered drug will transit down the small intestine following dissolution from an ingested dosage form and, if absorption rate is slow, it is possible that the drug can reach regions of poor permeability before absorption from a given dose is complete.

It is known that extending the release of metformin oral formulations invariably compromises and reduces the bioavailability of the drug. This result is probably because the dosage form carries a significant proportion of the drug content remaining to be released to regions of the gastro-intestinal tract with very poor permeability to the drug. To reduce dosing frequency, the rate of release from the dosage form must be such as to extend effective plasma levels, but the potential for effective delivery at this rate is compromised by the combined effect of significant reduction in permeability to the drug in passing from the proximal small intestine to the colon and the limited residence time of the dosage form in the regions of the gastro intestinal tract where the drug is intrinsically well absorbed.

While several prior art extended release metformin dosage forms have overcome the challenge of prolonging the release of metformin by extending the time to maximum plasma concentrations in the order of 6-8 hours, they are only achievable under high-fat fed conditions, contrary to recommended diets for patients with diabetes, and with a significant reduction of maximum plasma concentration. Furthermore these extended release formulations exhibit very significant food effect pharmacokinetics which adds to the intra subject variability during multiple dosing regimens.

In the case of one prior art extended release metformin formulation Glucophage® XR described in U.S. Pat. No. 6,660,300, when taken with a meal, the $C_{max}$ is achieved with a median time of 7.0 hours and the peak plasma concentration is 20% lower compared to the same dose of the immediate release Glucophage®, however the extent of absorption (measured by AUC) is similar to Glucophage®.

In the case of another prior art extended release metformin formulation Fortamet® described in U.S. Pat. No. 6,099,862, when taken with a meal, the $C_{max}$ is achieved with a median of 6.1 hours and the $C_{max}$ is 30% higher than that achieved in the fasting state. Furthermore, the extent of absorption (as measured by AUC) is 60% higher in the fed state in comparison to the same dose given in the fasted state.

In the case of yet another prior art extended release metformin formulation Glumetza® described in U.S. Pat. Nos. 6,340,475 and 6,488,962, when taken with a meal, the $C_{max}$ is achieved with a median of 7 hours, and the peak plasma concentration is 18% lower when compared to the same dose of the immediate release metformin, however the extent of absorption (as measured by AUC) is similar to immediate release metformin. Furthermore, there is a difference of 35% in the extent of absorption (as measured by AUC) when Glumetza® is taken with a low fat and a high fat meal. The AUC is higher with the high-fat meal.

It is clearly evident in these aforementioned prior art teachings of extended release metformin formulations that none can achieve comparable peak plasma concentration as compared to the same dose of the immediate release formulation in both fed and fasted states. The $C_{max}$ is significantly reduced most compromised in the fed state which ironically is the preferred mode of administration for both prior art immediate and extended release formulations. It is also evident that none can achieve a comparable extent of drug absorption as compared to the same dose of the immediate release formulation when taken in the fasted state or before meals. The extended release formulations, by virtue of the preferred mode of administration necessary for dosage form functionality exhibits a grossly reduced extent of drug absorption in the fasted state when compared to the same dose of the immediate release counterpart in the fasted state or of the same extended release formulation in the fed state.

While prior art teachings of extended release metformin have proffered obvious patient compliance improvements due to reduced frequency of administration, and reduced gastrointestinal adverse effects due to reduced rate of drug release from the dosage form in the gastrointestinal tract, it has not been shown that an improvement or at least a comparable clinical efficacy can be obtained when compared with the same doses of immediate release formulation taken in the fasted state or fed states. For example a 24 week, double blind, randomized study of the prior art extended release metformin formulation Glucophage® XR, taken 1000 mg once daily with evening meal and the immediate release metformin 500 mg Glucophage®, taken twice daily (with breakfast and evening meal), was conducted in patients with Type 2 diabetes. In this study, patients qualified for the study had glycosylated hemoglobin (HbA1c) of ≤8.5% and fasting plasma glucose (FPG) levels of ≤200 mg/dL. After 12 weeks of treatment, there was an increase in mean HbA1c in all groups; in the Glucophage® XR 1000 mg group the increase from baseline of 0.23% was statistically significant. The Glucophage® 1000 mg (500 mg b.i.d.) had an increase of 0.14%. Increased HbA1c levels after treatment intervention is indicative of impaired or poor efficacy.

It is evident that prior art teachings of metformin methods and compositions, immediate release and extended release are a) are not suited for administration before meals, b) not directed towards or suited for reducing postprandial glucose excursions, c) not able to overcome the undesirable food effect pharmacokinetics of drug. Furthermore, according to the drug monograph for Glucophage®, "the therapeutic goal of metformin according to the monographs is to achieve a decrease in both fasting plasma glucose and glycosylated hemoglobin levels to normal or near normal by using the lowest effective dose of Glucophage® or Glucophage® XR, either when used as monotherapy or in combination with sulfonylurea or insulin".

SUMMARY OF THE INVENTION

The present invention relates to treatment methods and compositions containing insulin-sensitizing oral hypoglycemic agents for reducing postprandial glucose excursions and for achieving superior blood glucose control in mammals, such as humans with insulin-related disorders or predisposed to insulin-related disorders. Specifically, the present application discloses methods that provide effective reduction of postprandial glucose excursions in non-diabetic individuals, individuals with pre-diabetes, impaired glucose tolerance, impaired fasting glucose, and patients with diabetes by improving the effectiveness and efficiency of endogenous insulin action with novel oral compositions of insulin-sensitizing oral hypoglycemic agents.

According to a first aspect of the present invention, there is provided a pharmaceutical composition comprising one, or more than one active agent-containing layer, each of the one, or more than one active agent-containing layer comprising a dry blended mixture comprising:

i) a therapeutically effective amount of a polar ionizable insulin-sensitizing oral hypoglycemic agent or a pharmaceutically acceptable salt thereof, and ii) an amphipathic compound in monomeric form consisting of an amphipathic ionic compound in monomeric form having a net charge opposite to that of the polar ionizable insulin-sensitizing oral hypoglycemic agent, wherein each dry blended mixture comprises a sufficient amount of the one amphipathic ionic compound such that upon contact with an aqueous fluid, the amphipathic ionic compound forms a reverse micelle comprising the polar ionizable insulin-sensitizing oral hypoglycemic agent, for reducing glucose excursions, such as postprandial glucose excursions, in a normal subject or in a subject having an insulin-related disorder or dysglycemia.

More particularly, the present invention provides a pharmaceutical composition for reducing glucose excursions, such as postprandial glucose excursions, in a normal subject or in a subject having an insulin-related disorder or dysglycemia, the pharmaceutical composition comprising one, or more than one active agent-containing layer, each of the one, or more than one active agent-containing layer comprising a dry blended mixture comprising:

i) a therapeutically effective amount of a polar ionizable insulin-sensitizing oral hypoglycemic agent or a pharmaceutically acceptable salt thereof, and ii) only one surfactant in monomeric form, wherein the one surfactant and the polar ionizable insulin-sensitizing oral hypoglycemic agent or the pharmaceutically acceptable salt thereof from each dry blended mixture are oppositely charged upon dissolution of each dry blended mixture in an aqueous fluid disposed within the gastrointestinal tract of a subject, and wherein each dry blended mixture comprises a sufficient amount of the one surfactant such that following dissolution of each dry blended mixture within the aqueous fluid, the one surfactant reaches a critical reverse micellar concentration within the aqueous fluid and forms a reverse micelle comprising the polar ionizable insulin-sensitizing oral hypoglycemic agent.

The present invention also provides the following examples of the pharmaceutical composition defined in the first aspect of the present invention.

In one example, one, or more than one of the one, or more than one active agent-containing layer further comprises an effective amount of one, or more than one release controlling agent for controlling the release of the insulin-sensitizing oral hypoglycemic agent from the pharmaceutical composition.

In another example, one, or more than one of the one, or more than one active agent-containing layer is coated or layered with a composition comprising an effective amount of one, or more than one release controlling agent for controlling the release of the insulin-sensitizing oral hypoglycemic agent from the pharmaceutical composition, and a pharmaceutically acceptable diluent or carrier.

In a further example, one, or more than one of the one, or more than one active-agent containing layer comprises, or is coated or layered with one, or more than one pH-dependent barrier polymer or enteric polymer.

In another example, one, or more than one of the one, or more than one active agent-containing layer further comprises or is layered or coated with one, or more than one adhesive composition comprising an effective amount of one, or more than one mucoadhesive agent for prolonging the residence time of the pharmaceutical composition in the mid- to lower gastro-intestinal tract of a subject, and a pharmaceutically acceptable diluent or carrier.

In a second aspect of the present invention, there is provided a pharmaceutical composition comprising one, or more than one active-agent containing layer, each of the one, or more than one active-agent containing layer comprising a dry blended mixture comprising:

i) a therapeutically effective amount of a polar ionizable insulin-sensitizing oral hypoglycemic agent or a pharmaceutically acceptable salt thereof, and ii) an amphipathic compound in monomeric form consisting of an amphipathic ionic compound in monomeric form having a net charge opposite to that of the polar ionizable insulin-sensitizing oral hypoglycemic agent, wherein one, or more than one of the one, or more than one active agent-containing layer further comprises or is layered or coated with one, or more than one adhesive composition comprising an effective amount of one, or more than one mucoadhesive agent for prolonging the residence time of the pharmaceutical composition in the mid- to lower gastro-intestinal tract of a subject, and a pharmaceutically acceptable diluent or carrier, wherein one, or more than one of the one, or more than one active agent-containing layer further comprises an effective amount of one, or more than one release controlling agent for controlling the release of the insulin-sensitizing oral hypoglycemic agent from the pharmaceutical composition, or wherein one, or more than one of the one, or more than one active agent-containing layer is coated or layered with a composition comprising an effective amount of one, or more than one release controlling agent for controlling the release of the insulin-sensitizing oral hypoglycemic agent from the pharmaceutical composition, and a pharmaceutically acceptable diluent or carrier, and wherein each dry blended mixture comprises a sufficient amount of the amphipathic ionic compound such that upon contact with an aqueous fluid, the one amphipathic ionic compound forms a reverse micelle comprising the polar ionizable insulin-sensitizing oral hypoglycemic agent.

More particularly, the present invention provides a pharmaceutical composition comprising one, or more than one active-agent containing layer, each of the one, or more than one active-agent containing layer comprising a dry blended mixture comprising:

i) a therapeutically effective amount of a polar ionizable insulin-sensitizing oral hypoglycemic agent or a pharmaceutically acceptable salt thereof, and ii) only one surfactant in monomeric form;

wherein one, or more than one of the one, or more than one active agent-containing layer further comprises or is layered or coated with one, or more than one adhesive composition comprising an effective amount of one, or more than one mucoadhesive agent for prolonging the residence time of the pharmaceutical composition in the mid- to lower gastro-intestinal tract of a subject, and a pharmaceutically acceptable diluent or carrier, wherein one, or more than one of the one, or more than one active agent-containing layer further comprises an effective amount of one, or more than one release controlling agent for controlling the release of the insulin-sensitizing oral hypoglycemic agent from the pharmaceutical composition, or wherein one, or more than one of the one, or more than one active agent-containing layer is coated or layered with a composition comprising an effective amount of one, or more than one release controlling agent for controlling the release of the insulin-sensitizing oral hypoglycemic agent from the pharmaceutical composition, and a pharmaceutically acceptable diluent or carrier, wherein the one surfactant and the polar ionizable insulin-sensitizing oral hypoglycemic agent or the pharmaceutically acceptable salt thereof from each dry blended mixture are oppositely charged upon dissolution of each dry blended mixture in an aqueous fluid disposed within the gastrointestinal tract of a subject, and wherein each dry blended mixture comprises a sufficient amount of the one surfactant such that following dissolution of each dry blended mixture within the aqueous fluid, the one surfactant reaches a critical reverse micellar concentration within the aqueous fluid and forms a reverse micelle comprising the polar ionizable insulin-sensitizing oral hypoglycemic agent.

The present invention also provides the following examples of the pharmaceutical composition defined in the first and second aspects of the present invention.

In one example, the release controlling agent comprises a compound non-swelling in aqueous media, such as a compound selected from the group consisting of cetyl alcohol, ethyl cellulose, polyvinyl alcohol, carbomer and a mixture thereof.

In another example, the one, or more than one pH-dependent barrier polymer may be selected from the group consisting of hydroxypropyl methyl cellulose phthalate (HPMCP), cellulose acetate phthalate (CAP), methacrylic acid-methyl methacrylate copolymer (1:1), and methacrylic acid-methyl methacrylate copolymer (1:2).

In a further example, the one, or more than one mucoadhesive agent can comprise one, or more than one mucoadhesive polymer capable of binding to the gastro-intestinal mucosa.

In a particular example, the one, or more than one mucoadhesive polymer is selected from the group consisting of hydrophilic polymers, anionic polymers and cationic polymers. In another particular example, the one, or more than one mucoadhesive polymer is selected from the group consisting of polyvinyl pyrrolidone (PVP), polymethlymethacrylate (Eudragit® NE30D), poly(ethylene oxide) polymers, methyl cellulose (MC), sodium carboxymethylcellulose (SCMC), hydroxypropyl cellulose (HPC), a carbopol, a polyacrylate, a mixed sodium and calcium salt of poly(methylvinyl ether/maleic anhydride), a mixed sodium and calcium salt of poly (methylvinyl ether/maleic anhydride copolymer, chitosan, a derivative of chitosan and a mixture thereof.

In a further example, one, or more than one of the one, or more than one adhesive composition comprises, or is coated or layered with one, or more than one pH-dependent barrier polymer or enteric polymer. In a particular example, the one, or more than one pH-dependent barrier polymer is selected from the group consisting of hydroxypropyl methyl cellulose phthalate (HPMCP), cellulose acetate phthalate (CAP), methacrylic acid-methyl methacrylate copolymer (1:1), and methacrylic acid-methyl methacrylate copolymer (1:2).

In another example, the amphipathic compound in monomeric form consisting of an amphipathic ionic compound in monomeric form is only one amphipathic compound in monomeric form consisting of only one amphipathic ionic compound in monomeric form.

In a further example, the polar ionizable insulin-sensitizing hypoglycemic agent in one, or more than one of the one, or more than one active agent-containing layer has a partition coefficient between octanol and water at pH 7.4 (dissociation constant between octanol and water) of less than about 10.

In an even further example, the polar ionizable insulin-sensitizing hypoglycemic agent in one, or more than one of the one, or more than one active agent-containing layer has a partition coefficient between octanol and water at pH 7.4 (dissociation constant between octanol and water) of greater than about 10.

In another example, the one, or more than one active agent-containing layer is two, or more than two active agent-containing layers, wherein the polar ionizable insulin-sensitizing hypoglycemic agent in one, or more than one layer of the two, or more than two active agent-containing layers has a partition coefficient between octanol and water at pH 7.4 (dissociation constant between octanol and water) of less than about 10, and wherein the polar ionizable insulin-sensitizing hypoglycemic agent in one, or more than one other layer of the two, or more than two active agent-containing layers has a partition coefficient between octanol and water at pH 7.4 (dissociation constant between octanol and water) of greater than about 10.

The present invention also relates to the pharmaceutical composition defined in the first and second aspects of the present invention, wherein:

i) the polar ionizable insulin-sensitizing hypoglycemic agent in one, or more than one of the one, or more than one active agent-containing layer belongs to Class I of the Biopharmaceutics Classification System;

ii) the polar ionizable insulin-sensitizing hypoglycemic agent in one, or more than one of the one, or more than one active agent-containing layer belongs to Class II of the Biopharmaceutics Classification System;

iii) the polar ionizable insulin-sensitizing hypoglycemic agent in one, or more than one of the one, or more than one active agent-containing layer belongs to Class III of the Biopharmaceutics Classification System;

iv) the polar ionizable insulin-sensitizing hypoglycemic agent in one, or more than one of the one, or more than one active agent-containing layer belongs to Class IV of the Biopharmaceutics Classification System;

v) the one, or more than one active agent-containing layer is two, or more than two active agent-containing layers, wherein the polar ionizable insulin-sensitizing hypoglycemic agent in one, or more than one layer of the two, or more than two active agent-containing layers belongs to Class I of the Biopharmaceutics Classification System, and wherein the polar ionizable insulin-sensitizing hypoglycemic agent in one, or more than one other layer of the two, or more than two active agent-containing layers belongs to Class II, III or IV of the Biopharmaceutics Classification System;

vi) the one, or more than one active agent-containing layer is two, or more than two active agent-containing layers, wherein the polar ionizable insulin-sensitizing hypoglycemic agent in one, or more than one layer of the two, or more than two active agent-containing layers belongs to Class II of the Biopharmaceutics Classification System, and wherein the polar ionizable insulin-sensitizing hypoglycemic agent in one, or more than one other layer of the two, or more than two active agent-containing layers belongs to Class I, III or IV of the Biopharmaceutics Classification System;

vii) the one, or more than one active agent-containing layer is two, or more than two active agent-containing layers, wherein the polar ionizable insulin-sensitizing hypoglycemic agent in one, or more than one layer of the two, or more than two active agent-containing layers belongs to Class III of the Biopharmaceutics Classification System, and wherein the polar ionizable insulin-sensitizing hypoglycemic agent in one, or more than one other layer of the two, or more than two active agent-containing layers belongs to Class I, II or IV of the Biopharmaceutics Classification System; or viii) the one, or more than one active agent-containing layer is two, or more than two active agent-containing layers, wherein the polar ionizable insulin-sensitizing hypoglycemic agent in one, or more than one layer of the two, or more than two active agent-containing layers belongs to Class IV of the Biopharmaceutics Classification System, and wherein the polar ionizable insulin-sensitizing hypoglycemic agent in one, or more than one other layer of the two, or more than two active agent-containing layers belongs to Class I, II or III of the Biopharmaceutics Classification System.

In a further example, the one, or more than one active agent-containing layer is two, or more than two active agent-containing layers, wherein the polar ionizable insulin-sensitizing hypoglycemic agent in one, or more than one layer of the two, or more than two active agent-containing layers is the same as or different from the polar ionizable insulin-sensitizing hypoglycemic agent in one, or more than one other layer of the two, or more than two active agent-containing layers.

In another example, the amphipathic ionic compound is present in one, or more than one of the one, or more than one active agent-containing layer in an amount of about 0.5 weight % to about 500 weight %.

The present invention further relates to the pharmaceutical composition defined in the first and second aspects of the present invention, wherein:
i) the amphipathic ionic compound in one, or more than one layer of the one, or more than one active agent-containing layer is an anionic surfactant, and the polar ionizable insulin-sensitizing hypoglycemic agent in the one, or more than one layer of the one, or more than one active agent-containing layer is positively charged;
ii) the amphipathic ionic compound in each of the one, or more than one active agent-containing layer is an anionic surfactant, and the polar ionizable insulin-sensitizing hypoglycemic agent in each of the one, or more than one active agent-containing layer is positively charged;
iii) the amphipathic ionic compound in one, or more than one layer of the one, or more than one active agent-containing layer is a cationic surfactant, and the polar ionizable insulin-sensitizing hypoglycemic agent in the one, or more than one layer of the one, or more than one active agent-containing layer is negatively charged;
iv) the amphipathic ionic compound in each of the one, or more than one active agent-containing layer is a cationic surfactant, and the polar ionizable insulin-sensitizing hypoglycemic agent in each of the one, or more than one active agent-containing layer is negatively charged; or
v) the one, or more than one active agent-containing layer is two, or more than two active agent-containing layers, wherein the amphipathic ionic compound in one, or more than one layer of the two, or more than two active agent-containing layers is an anionic surfactant, and the polar ionizable insulin-sensitizing hypoglycemic agent in the one, or more than one layer of the two, or more than two active agent-containing layers is positively charged, and wherein the amphipathic ionic compound in one, or more than one other layer of the two, or more than two active agent-containing layers is a cationic surfactant, and the polar ionizable insulin-sensitizing hypoglycemic agent in the one, or more than one other layer of the two, or more than two active agent-containing layers is negatively charged.

The anionic surfactant may be selected from the group consisting of sodium or potassium dodecyl sulfate, sodium octadecylsulfate, sodium bis(2-ethylhexyl)sulfosuccinate (AOT), and a combination thereof. In addition, the cationic surfactant may be selected from the group consisting of didodecyl dimethyl ammonium bromide (DDAB), cetyl-triammonium bromide (CTAB), cetylpyridinium bromide (CPB), dodecyl trimethyl ammonium chloride (DOTAC), sodium perfluorononanoate (SPFN), hexadecyl trimethyl ammonium bromide (HDTMA), and a combination thereof.

The dry blended mixture of one, or more than one layer of the one, or more than one active agent-containing layer may further comprise a pharmaceutically acceptable excipient selected from the group consisting of a viscosity enhancer, a diluent, an anti-adherent, a glidant, a binder, a solubilizer, a channeling agent, a buffering agent, a flavourant, an adsorbent, a sweetening agent, a colorant, a lubricant, and a combination thereof.

The pharmaceutical composition defined in the first and second aspects of the present invention may be in the form of a matrix solid compact, made by a compression or pelletization method, or a matrix extrusion spheroid, made by a wet or dry extrusion method.

The present invention also relates to the above-defined pharmaceutical compositions, wherein the pharmaceutical composition is for administration before a morning meal, is for administration on a once-daily basis before a morning meal, is for administration from approximately 60 minutes prior to the beginning of a morning meal to approximately 60 minutes after the beginning of a morning meal, or is for administration within 30 minutes prior to the beginning of the morning meal.

The pharmaceutical compositions of the present invention may be for reducing glucose excursions in a normal subject or a subject having an insulin-related disorder or dysglycemia. The insulin related disorder may be diabetes mellitus, Type 2 diabetes mellitus, early stage Type 1 diabetes mellitus, pre-diabetes, or impaired fasting glucose.

The insulin-sensitizing oral hypoglycemic agent in one, or more than one layer of the one, or more than one active-agent-containing layer of the pharmaceutical compositions of the present invention may be a biguanide, such as metformin, or a pharmaceutically acceptable salt thereof.

The present invention also includes pharmaceutical compositions containing metformin in one, or more than one layer of the one, or more than one active agent-containing layer, wherein the metformin is for administration in an amount of one gram once daily, or for administration in an amount of 0.25 to 3.0 grams daily.

In another example, the pharmaceutical compositions of the present invention comprise metformin as the insulin-sensitizing hypoglycemic agent and exhibit the following dissolution profile when tested in a USP Type 2 apparatus at 50 rpm in 1000 ml of simulated intestinal fluid (pH 6.8 phosphate buffer at 37° C.):
i) 0-20% of the metformin or a pharmaceutically acceptable salt thereof is released after 0.5 hour;
ii) 20-30% of the metformin or a pharmaceutically acceptable salt thereof is released after 1 hour;
iii) 30-40% of the metformin or a pharmaceutically acceptable salt thereof is released after 2 hours;
iv) 35-45% of the metformin or a pharmaceutically acceptable salt thereof is released after 3 hours;
v) 45-55% of the metformin or a pharmaceutically acceptable salt thereof is released after 5 hours;
vi) 55-65% of the metformin or a pharmaceutically acceptable salt thereof is released after 7 hours;
vii) 65-75% of the metformin or a pharmaceutically acceptable salt thereof is released after 11 hours;
viii) 75-85% of the metformin or a pharmaceutically acceptable salt thereof is released after 16 hours;
ix) not less than 80% of the metformin or a pharmaceutically acceptable salt thereof is released after 19 hours; and
x) not less than 85% of the metformin or a pharmaceutically acceptable salt thereof is released after 24 hours.

Pharmaceutical compositions of the present invention comprising metformin as the polar ionizable insulin-sensitizing oral hypoglycemic agent in one, or more than one layer of the one, or more than one active-agent-containing layer may have one, or more than one of the following characteristics following administration before a morning meal or breakfast:
i) a mean time to maximum plasma concentration ($T_{max}$) of metformin of from 2.5 to about 6.5 hours following administration;
ii) a width at 50% of the height of a mean plasma concentration/time curve of the metformin from about 1.0 to about 10 hours and a width 25% of the height of mean plasma concentration/time curve of the metformin from about 0.25 to about 14 hours;

iii) a mean maximum plasma concentration ($C_{max}$) of metformin which is more than about 10 times the mean plasma level of the metformin at about 24 hours after the administration;

iv) a mean maximum plasma concentration ($C_{max}$) of metformin which is from about 10 times to about 20 times the plasma level of the metformin at about 24 hours after administration;

v) a mean maximum plasma concentration ($C_{max}$) of metformin from about 1.18 µg/ml to about 1.60 µg/ml, based on administration of a 1000 mg once-a-day dose of metformin;

vi) a mean $AUC_{0-24hr}$ from about 10.0 µg·hr/ml to about 13.0 µg·hr/ml, based on administration of a 1000 mg once-a-day dose of metformin;

vii) a mean drug exposure and $AUC_{0-24hr}$ from about 18.00 µg·hr/ml to about 22.00 µg·hr/ml, based on administration of a 2000 mg once-a-day dose of metformin;

viii) provides, at single dose, a mean drug exposure and mean $AUC_{0-\infty}$ of 10.10±1.9 ug·hr/ml and a mean peak plasma concentration and $C_{max}$ of 1.19±0.25 ug/ml, for administration of a 1000 mg once-a-day dose of metformin;

ix) a mean $AUC_{0-24hr}$ of 11.75±3.90 µg·hr/ml and a mean $C_{max}$ of 1.51±0.43 µg/ml on the first day of administration and a mean $AUC_{0-24hr}$ of 12.95±3.6 µg·hr/ml and a mean $C_{max}$ of 1.48±0.45 µg/ml on the $7^{th}$ day of administration, for administration of a 1000 mg once-a-day dose of metformin; or x) a mean $t_{1/2}$ from 4.0 to 6.0

The present invention also relates to the use of the above-defined pharmaceutical compositions for reducing the risk of developing diabetes or a disease associated with glucose excursions.

The pharmaceutical compositions of the present invention are capable of delivering the insulin-sensitizing oral hypoglycemic agent through the upper-, mid- and lower-GI tract of a subject following administration.

In a third aspect of the present invention, there is provided a method of sensitizing pre-prandial (basal) insulin levels and/or reducing postprandial glucose excursions in a normal patient or a patient having an insulin-related disorder, comprising administering to the patient a single dose of a modified release pharmaceutical composition comprising one, or more than one active agent-containing layer, each of the one, or more than one active agent-containing layer comprising a therapeutically effective amount of an insulin-sensitizing oral hypoglycemic agent and an effective amount of a release controlling agent for controlling the release of the insulin sensitizing oral hypoglycemic agent from the pharmaceutical composition before the patient has consumed a morning meal, wherein following administration of the pharmaceutical composition a plasma concentration of the insulin-sensitizing oral hypoglycemic agent is achieved in the patient over time such that fifty percent of the maximum plasma concentration ($C_{max}$) of the insulin-sensitizing oral hypoglycemic agent is sustained in the patient for a period of about 1 to about 12 hours, from about 1.0 to 10.0 hours, or any subrange of value therebetween or from about 2.0 to 8.0 hours, or an subrange of value therebetween, about 0.5 hour following administration of the dose.

The method of the present invention can produce one, or more than one of the following advantageous results:

reduces the incidence of clinically relevant late insulin-mediated glucose disposal;

improves hepatic and peripheral tissue distribution;

improves sensitization of both basal and secreted insulin in hepatic and peripheral tissues;

provides therapeutic levels of the anti-hypoglycemic drug for twelve to twenty-four hour periods;

does not exhibit a decrease in bioavailability if taken with food;

provides therapeutic levels of the drug throughout the day with peak plasma levels being obtained between 2.5 to 6.5 hours after administration;

provides a mean maximum plasma concentration ($C_{max}$) of the oral hypoglycemic agent of from about 8 times to about 20 times the plasma level of the agent at about 24 hours after administration;

provides extended absorption without gastric retention and with substantial post-gastric absorption.

When the insulin-sensitizing oral hypoglycemic agent used in one, or more than one layer of the one, or more than one active agent-containing layer of the modified release pharmaceutical composition of the present invention is metformin, the method of the present invention may produce one, or more than one of the following additional advantageous results:

reduces postprandial glucose excursions by at least 25% more than an equivalent dose of a once-daily extended release metformin composition reference standard, while providing substantially similar plasma metformin exposure as the reference standard;

reduces postprandial glucose excursions by at least 25% more than an equivalent dose of a twice-daily immediate release metformin composition reference standard, while providing substantially similar plasma metformin exposure as the reference standard;

provides a delayed $T_{max}$, relative to the $T_{max}$ provided by an equivalent dose of Glucophage® administered twice-daily with meals. The delayed $T_{max}$ may occur from about 2.5 to about 7 hours or from about 3.5 to about 7.0 hours after administration;

provides a higher mean maximum plasma concentration ($C_{max}$), as compared to the $C_{max}$ provided by an equivalent dose of Glucophage® administered twice-daily with meals or Glucophage® XR administered once-daily with meals. The higher $C_{max}$ may be about 1.2 to 1.52 micrograms per milliliter;

provides a total metformin exposure ($AUC_{0-24}$ hours) that is at least 80% of that produced by an equivalent dose of Glucophage® administered twice-daily.

In an example of the method of the third aspect of the present invention, following administration of the pharmaceutical composition a plasma concentration of the insulin-sensitizing oral hypoglycemic agent is achieved in the patient over time such that twenty five percent of the maximum plasma concentration ($C_{max}$) of the insulin-sensitizing oral hypoglycemic agent is sustained in the patient for a period of about 1 to about 14 hours, or from about 1.0 to 12.0 hours following administration of the dose.

In another example of the above method, the modified release pharmaceutical composition is the pharmaceutical composition of the first or second aspect of the present invention described above. In other examples, the modified release pharmaceutical composition is the modified release compositions disclosed in U.S. Pat. No. 6,309,663, or in U.S. Pat. Appl. Publication No. 2006/0025346.

The modified release pharmaceutical composition of the third aspect of the present invention can deliver the insulin-sensitizing oral hypoglycemic agent through the upper-, mid- and lower-GI tract of the subject following administration In a further example of the above method, the modified release metformin composition is administered approximately 10 minutes to 30 minutes, or more than 30 minutes prior to the time the subject has begun the morning meal to approximately 5 minutes after the subject has begun the meal.

In an even further example, the glucose excursions are determined by a 24-hour positive incremental area under the glucose concentration vs. time curve ($iAUC_{0-24}$) and a change in glucose excursion ($\Delta\ iAUC_{0-24}$) is determined by comparison of values of $iAUC_{0-24}$ determined before and after treatment with the pharmaceutical composition comprising the oral hypoglycemic agent under similar dietary conditions of substantially similar glycemic loads.

In a fourth aspect, the present invention provides a reverse micelle comprising a polar ionizable insulin-sensitizing oral hypoglycemic agent or a pharmaceutically acceptable salt thereof, and an amphipathic compound in monomeric form consisting of an amphipathic ionic compound in monomeric form having a net charge opposite to that of the polar ionizable insulin-sensitizing oral hypoglycemic agent, which may be produced from the pharmaceutical composition defined above in the first and second aspects of the present invention, for reducing glucose excursions in a normal subject or a subject having an insulin-related disorder or dysglycemia.

In a fifth aspect of the present invention, there is provided a method for reducing glucose excursions, such as postprandial glucose excursions, in a normal subject or a subject having an insulin-related disorder or dysglycemia, comprising:

i) orally administering the pharmaceutical composition defined above to the subject, and ii) allowing the reverse micelle comprising the polar ionizable insulin-sensitizing oral hypoglycemic agent or the pharmaceutically acceptable salt thereof to be formed within and absorbed across the gastrointestinal tract of the subject, thereby delivering the polar ionizable insulin-sensitizing oral hypoglycemic agent or the pharmaceutically acceptable salt thereof to the subject.

More particularly, the present invention provides a method for reducing glucose excursions, such as postprandial glucose excursions, in a normal subject or a subject having an insulin-related disorder or dysglycemia, comprising:

i) orally administering to the subject a pharmaceutical composition comprising one, or more than one active agent-containing layer, each of the one, or more than one active agent-containing layer comprising a dry blended mixture comprising:

a therapeutically effective amount of a polar ionizable insulin-sensitizing oral hypoglycemic agent or a pharmaceutically acceptable salt thereof, and only one surfactant in monomeric form, wherein the one surfactant and the polar ionizable insulin-sensitizing oral hypoglycemic agent or the pharmaceutically acceptable salt thereof from each dry blended mixture are oppositely charged upon dissolution of each dry blended mixture in an aqueous fluid disposed within the gastrointestinal tract of a subject, and wherein each dry blended mixture comprises a sufficient amount of the one surfactant such that following dissolution of each dry blended mixture within the aqueous fluid, the one surfactant reaches a critical reverse micellar concentration within the aqueous fluid and forms a reverse micelle comprising the polar ionizable insulin-sensitizing oral hypoglycemic agent, and ii) allowing the reverse micelle comprising the polar ionizable insulin-sensitizing oral hypoglycemic agent or the pharmaceutically acceptable salt thereof from each dry blended mixture to be formed within and absorbed across the gastrointestinal tract of the subject, thereby delivering the polar ionizable insulin-sensitizing oral hypoglycemic agent or the pharmaceutically acceptable salt thereof from each dry blended mixture to the subject.

It is known that a combination of metformin and insulin therapy in Type 2 diabetics provides superior blood glucose and % $HbA1_C$ lowering compared to metformin or insulin therapy alone. In addition, insulin levels decline with metformin use in patients with Type 2 diabetes. Whether the drug actually sensitizes peripheral tissues, such as muscle and fat, to insulin remains controversial. However, it is quite plausible to hypothesize that an oral hypoglycemic agent formulation that possess the in-vivo quantitative and kinetic properties such that therapeutically effective amount of the drug is systemically available at a rate that approximates the first phase insulin release of normal subjects and that is adequately and preferably distributed into hepatocytes and peripheral tissues may in fact sensitize these tissues to insulin.

The timing and distribution of metformin in a manner that mimics physiological demands for insulin-mediated glucose elimination in the target tissues will proffer a superior therapy that will be effective in potentiating endogenous insulin action. These in turn may improve the effectiveness of the drug in lowering glucose excursions and in consequence provide tight short-term glycemic control.

It is reasonable to assume that by taking advantage of the potentiating effects of a rapid spike in metformin concentration, endogenous insulin from both basal and impaired burst secretions in Type 2 diabetics or patients with insulin-related disorders will be preferably sensitized to mimic the effect of normal first-phase insulin kinetics. The oral hypoglycemic agent compositions of the present invention may be administered a few minutes before commencing a meal; unlike the more slowly absorbed extended release and or late absorption onset prior art immediate release metformin formulations, which are usually taken after meals. The dosing interval and mode of administration in the fed state of prior art metformin formulations in both their immediate or extended release dosage forms are generally based on patient tolerability, conditions favorable for maximum absorption, and on the time needed to achieve maximal metformin concentration.

It has been generally assumed that the rate of glucose elimination at any point in time is a function of insulin concentration at that point in time. In point of fact, the glucose elimination rate achieved by any particular insulin concentration is influenced by the prior "sensitized" or "primed" state of hepatocytes and peripheral tissues to the available insulin. Thus, glucose disposal rates are invariably potentiated by previous levels of insulin at the target tissues that are functionally capable of facilitating glucose elimination. Therefore, for any particular insulin concentration, the glucose elimination rate is greater when the subject has recently experienced either a high surge in insulin concentration and/or when insulin receptors at the target tissues have been primed or sensitized to the available insulin in a preceding time interval.

The inadequate glucose lowering therapy from prior art immediate release treatments, taken twice daily after meals, was based on the tacit assumption that glucose elimination rate is a function of insulin concentration. In addition, the inadequate glucose lowering therapy from prior art extended release metformin, taken once daily after evening meal, was based on the assumption that glucose elimination is most needed during peak period of gluconeogenesis (~2 am or early hours of the morning).

In the present application, investigations have been conducted into the pharmacokinetics and pharmacodynamics of a rapid-absorption modified release oral hypoglycemic agent composition for the treatment and amelioration of postprandial glucose excursions, which surprisingly demonstrated that a favorable potentiation of insulin action can be achieved in healthy and diabetic individuals through properly delivered insulin-sensitizing oral hypoglycemic agents, such as metformin. It is hypothesized that this potentiation, derived from a rapid absorption of the oral hypoglycemic agent, drives glucose elimination rate to maximum much more quickly, and that the continued and sustained absorption of therapeutically effective levels of the oral hypoglycemic agent, furthers the potentiation over an extended period of time in response to multiple post-meal glucose challenges in the course of a the day.

Due to the potentiating effect of a rapid-absorption modified release oral hypoglycemic agent preparation causing a rapid rise and prolonged serum metformin concentrations, it can be more readily coordinated with a meal. The quick acquisition of maximal glucose elimination rate and the slow release of the oral hypoglycemic agent from the modified release dosage form reduce gastrointestinal adverse effects while advancing superior therapy for lowering blood glucose. The oral dosage form of the rapid-absorption modified release oral hypoglycemic agent composition is well suited to pre-mealtime administration, or even up to an hour after commencing a meal. Further advantages are realized in diabetics who retain some ability to produce insulin in that their endogenous second-phase and basal insulin will also be potentiated by the oral hypoglycemic agent, increasing the effectiveness of that limited insulin and reducing pancreatic stress.

BRIEF DESCRIPTION OF THE DRAWINGS

These and other features of the invention will become more apparent from the following description in which reference is made to the appended drawings wherein:

FIG. 3 illustrates comparative plots of dissolution profiles of GlycoBien® CR 1000 mg and Glucophage® XR (extended release metformin) tested at 50 rpm with a USP type II dissolution apparatus in phosphate buffer pH 6.8 at a temperature of 37° C. % drug released are mean values of metformin released over a period of time (hr).

FIG. 4 illustrates comparative plots of plasma metformin concentration-time profiles of GlycoBien® CR 1000 mg and Glucophage® 1000 mg (2×500 mg) during a single-dose fasted state crossover bioavailability study involving twenty-five (25) healthy male and female subjects.

FIG. 5 illustrates comparative plots of plasma metformin concentration-time profiles of GlycoBien® CR 1000 mg, GlycoBien® CR 2000 mg (2×1000 mg), and Glucophage® 1000 mg (2×500 mg) during a single-dose fasted state crossover dose-proportionality bioavailability study involving twenty-six (26) healthy male and female subjects.

FIG. 6 illustrates comparative plots of plasma metformin concentration-time profiles of GlycoBien® CR 1000 mg taken in the fasted state and taken after a high-fat meal during a single-dose food-effect crossover bioavailability study involving twenty-five (25) healthy male and female subjects.

FIG. 7 illustrates comparative plots of plasma metformin concentration-time profiles of GlycoBien® CR 1000 mg taken after a low-fat meal and taken after a high-fat meal in a single-dose food-effect crossover bioavailability study involving eighteen (18) healthy male and female subjects.

FIG. 8A illustrates comparative plots of plasma metformin concentration-time profiles of GlycoBien® CR 1000 mg taken before morning breakfast and Glucophage® XR 1000 mg (2×500 mg) taken after evening dinner in a single-dose crossover pharmacokinetics study involving fourteen (14) healthy male and female subjects.

FIG. 8B illustrates comparative plots of plasma metformin concentration-time profiles of GlycoBien® CR 1000 mg taken before morning breakfast and Glucophage® XR 1000 mg (2×500 mg) taken after evening dinner after Day-7 in a multi-dose steady-state crossover pharmacokinetics study involving thirteen (13) healthy male and female subjects.

FIG. 9B illustrates comparative plots of both single-dose and multi-dose daily postprandial plasma glycemic excursions (serum glucose iAUC$_{0-24}$) in healthy male and female subjects fed glycemic-load standardized meals in a steady-state crossover pharmacodynamics studies of treatments with Placebo, GlycoBien® CR 1000 mg taken before breakfast, and Glucophage® XR 1000 mg (2×500 mg) taken after evening dinner.

FIG. 9C illustrates comparative plots of breakfast, lunch and dinner postprandial glycemic excursions (serum glucose iAUC$_{0-x}$) in healthy male and female subjects fed glycemic-load standardized meals for breakfast, lunch and dinner in a crossover pharmacodynamics studies of single-dose treatments with Placebo, GlycoBien® CR 1000 mg taken before breakfast, and Glucophage® XR 1000 mg (2×500 mg) taken after evening dinner.

FIG. 9D illustrates comparative plots of breakfast, lunch and dinner postprandial glycemic excursions (serum glucose iAUC$_{0-x}$) in healthy male and female subjects fed glycemic-load standardized meals for breakfast, lunch and dinner in a crossover pharmacodynamics studies at Day-7 of multi-dose treatments with Placebo, GlycoBien® CR 1000 mg taken before breakfast, and Glucophage® XR 1000 mg (2×500 mg) taken after evening dinner.

FIG. 10A illustrates comparative plots of plasma metformin concentration-time profiles of GlycoBien® CR 1000 mg taken before morning breakfast and Glucophage® 500 mg (500 mg b.i.d.) taken twice-daily after breakfast and evening dinner in a single-dose crossover pharmacokinetics study involving ten (10) healthy male and female subjects.

FIG. 10B illustrates comparative plots of plasma metformin concentration-time profiles of GlycoBien® CR 1000 mg taken before morning breakfast and Glucophage® 500 mg (500 mg b.i.d.) taken twice-daily after breakfast and evening dinner at Day-7 in a multi-dose steady-state crossover pharmacokinetics study involving thirteen (10) healthy male and female subjects.

Figure 1:
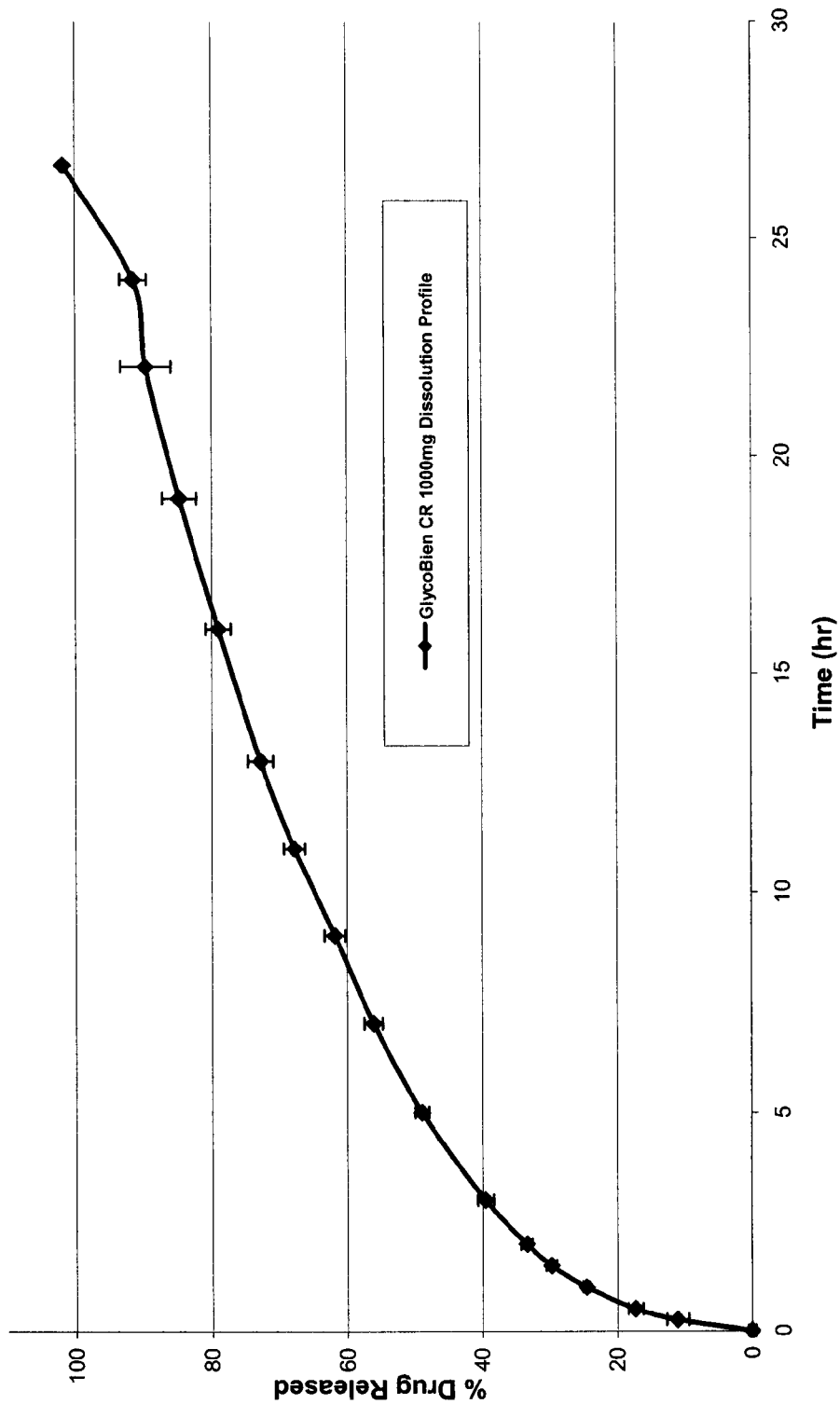
FIG. 1 illustrates a dissolution profile of GlycoBien® CR 1000 mg, an example of the pharmaceutical compositions of the present invention, tested at 50 rpm with a USP type II dissolution apparatus, in phosphate buffer, pH 6.8, at a temperature of 37° C. % drug released are mean values of metformin released over a period of time (hr).

FIG. 11A illustrates comparative plots of daily postprandial plasma glycemic excursions (serum glucose $iAUC_{0-24}$) in ten (10) healthy male and female subjects fed glycemic-load standardized meals at Day-7 in a multi-dose crossover pharmacodynamics studies of treatments with Placebo, GlycoBien® CR 1000 mg taken before breakfast, and Glucophage® 500 mg (500 mg b.i.d.) taken twice-daily after breakfast and evening dinner.

FIG. 11B illustrates comparative plots of both single-dose and multi-dose daily postprandial plasma glycemic excursions (serum glucose $iAUC_{0-24}$) in healthy male and female subjects fed glycemic-load standardized meals in a steady-state crossover pharmacodynamics studies of treatments with Placebo, GlycoBien® CR 1000 mg taken before breakfast, and Glucophage® 500 mg (500 mg b.i.d.) taken twice-daily after breakfast and evening dinner.

FIG. 11C illustrates comparative plots of breakfast, lunch and dinner postprandial glycemic excursions (serum glucose $iAUC_{0-x}$) in healthy male and female subjects fed glycemic-load standardized meals for breakfast, lunch and dinner in a crossover pharmacodynamics studies of single-dose treatments with Placebo, GlycoBien® CR 1000 mg taken before breakfast, and Glucophage® 500 mg (500 mg b.i.d.) taken twice-daily after breakfast and evening dinner.

FIG. 11D illustrates comparative plots of breakfast, lunch and dinner postprandial glycemic excursions (serum glucose $iAUC_{O-x}$) in healthy male and female subjects fed glycemic-load standardized meals for breakfast, lunch and dinner in a crossover pharmacodynamics studies at Day-7 of multi-dose treatments with Placebo, GlycoBien® CR 1000 mg taken before breakfast, and Glucophage® 500 mg (500 mg b.i.d.) taken twice-daily after breakfast and evening dinner.

FIG. 12A illustrates comparative plots of Insulin response, overall glycemic response (serum glucose AUC) and postprandial glycemic excursions (serum glucose $iAUC_{0-x}$) in the Single-Dose Pharmacodynamic Study in healthy male and female subjects fed glycemic-load standardized meals for breakfast, lunch, dinner and snack in a crossover pharmacodynamics studies of GlycoBien® CR 1000 mg taken before breakfast, and Glucophage® 500 mg (500 mg b.i.d.) taken twice-daily after breakfast and evening dinner.

FIG. 12B illustrates comparative plots of Insulin response, overall glycemic response (serum glucose AUC) and postprandial glycemic excursions (serum glucose $iAUC_{0-x}$) in the Multi-Dose Pharmacodynamic Study at Day-7 of Treatment in healthy male and female subjects fed glycemic-load standardized meals for breakfast, lunch, dinner and snack in a crossover pharmacodynamics studies of GlycoBien® CR 1000 mg taken before breakfast, and Glucophage® 500 mg (500 mg b.i.d.) taken twice-daily after breakfast and evening dinner.

DETAILED DESCRIPTION

The present invention relates to treatment methods and compositions containing insulin-sensitizing oral hypoglycemic agents for reducing postprandial glucose excursions and for achieving superior blood glucose control in mammals, such as humans, with insulin-related disorders or predisposed to insulin-related disorders. Specifically, the present application discloses methods that provide effective reduction of postprandial glucose excursions in non-diabetic individuals, individuals with pre-diabetes, impaired glucose tolerance, impaired fasting glucose, and patients with diabetes by improving the effectiveness and efficiency of endogenous insulin action with novel oral compositions of insulin-sensitizing oral hypoglycemic agents.

DEFINITION OF TERMS

As used herein the term "diabetes" refers to Type 2 (or Type II) diabetes or non-insulin dependent diabetes mellitus.

As used herein, "insulin-related disorders" refers to disorders involving production, regulation, metabolism, and action of insulin in a mammal such as a human. Insulin related disorders include, but are not limited to; Type 1 diabetes mellitus, Type 2 diabetes mellitus, impaired glucose tolerance, hypoglycemia, hyperglycemia, insulin resistance, loss of pancreatic beta cell function and loss of pancreatic beta cells.

As used herein, "first-phase" insulin refers to a burst release of insulin from the pancreas induced as a result of a meal. The first-phase release generates a spike in blood insulin concentration that manifests as a rapid peak that decays relatively quickly.

As used herein, "second-phase" insulin refers to a modest rise in insulin that decays slowly back to baseline after the first phase has passed. The second-phase can also refer to the non-spike release of insulin in response to elevated blood glucose levels.

As used herein, the term "metformin" means metformin base or any pharmaceutically acceptable salt thereof such as the hydrochloride salt, the metformin (2:1) fumarate salt and the metformin (2:1) succinate salt as disclosed U.S. Pat. No. 6,031,004, the hydrobromide salt, the p-chloro phenoxyacetate or the embonate, and other known metformin salts of mono and dibasic carboxylic acids.

As used herein, the term "glucose excursion" refers to Incremental blood glucose response measured as positive changes in blood glucose, above a baseline level, over a period time. The baseline blood glucose level is assumed as the basal glucose attained in the homeostatic state such as fasting or pre-meal blood glucose. Quantitatively, glucose excursion in this context is expressed as the positive incremental area under the blood or plasma glucose concentration time curve over a period of time (iAUC) determined according to equation 1 and using fasting or pre-meal blood glucose level as baseline.

As used herein the term "positive incremental AUC" or "iAUC" is the calculation of the area under the blood glucose concentration-time curve (AUC) using the fasting blood glucose or other pre-meal time point as the baseline and disregarding any values below zero or the chosen pre-meal baseline. The iAUC is determined over a time period such as from 0-3 hr., 0-4 hr., or 0-24 hr. Positive iAUC calculations are determined according to equation 1.

As used herein the term "change in glucose excursion" is Δ $iAUC_{0-t}$ or change in positive incremental AUC is the calculation of the difference between the iAUC attained, without treatment intervention or placebo treatment, under a specified condition of carbohydrate meal challenge and the iAUC attained with treatment intervention or drug treatment, under similar conditions of carbohydrate meal challenge and over the same time period.

As used herein, the term "fasting" or "fasted state" refers to a condition wherein the subject has not eaten any meal (except for consumption of water) over a period of at least ten (10) hours prior to dosage administration and followed by continued fasting for a minimum additional four (4) hours post dose. Typically, administration of drug in the fasting or fasted state is established after ten (10) hours of fasting and a further four hours post-dose of fasting before consumption of the first meal.

As used herein, the term "pre-prandial glucose" refers to a blood glucose level just before eating begins. "Post-prandial glucose" refers to a blood glucose level after eating.

As used herein, "postprandial" refers to a period of time after ingestion of a meal or snack. Postprandial glucose can be measured at various time points following the start of meal consumption and can vary from 0 to 240 min from the start of ingestion of a meal. Late postprandial refers to a period of time of approximately 3-4 hours or more after ingestion of a meal or snack.

As used herein "postprandial glucose excursion" refers to the area under the plasma or serum glucose concentration versus time curve (AUC) over specified time frames above the fasting or pre-meal baseline and based on a desired index for measuring changes in glucose concentrations such as $AUC_{0-t}$, or positive incremental $AUC_{0-t}$.

As used herein, "glucose elimination rate" is the rate at which glucose disappears from the blood.

As used herein, "hyperglycemia" is a higher than normal fasting or postprandial blood glucose concentrations usually 126 mg/dL or higher. In some studies hyperglycemic episodes were defined as blood glucose concentrations exceeding 280 mg/dL (15.6 mM).

The term "morning" as it is used herein with respect to the dosage administration of the invention means that the dosage form is orally administered early in the day after the patient has awakened from overnight sleep, generally between about 6 a.m. and 11 a.m. (regardless of whether breakfast is eaten at that time, unless so specified herein).

As used herein, the term "breakfast" or "at breakfast" is used with respect to a time when breakfast is normally eaten (regardless of whether a meal is actually eaten at that time, unless so specified herein), generally between about 6 a.m. and 10 a.m.

As used herein, the term "lunchtime" or "at lunch" is used with respect to a time when lunch is normally eaten (regardless of whether a meal is actually eaten at that time, unless so specified herein), generally between about 11 a.m. and 2 p.m.

As used herein, the term "dinnertime" or "at dinner" is used with respect to a time when dinner is normally eaten (regardless of whether a meal is actually eaten at that time, unless so specified herein), generally between about 4 p.m. and 8 p.m.

As used herein, the term "$C_{max}$" is the highest plasma concentration of the drug attained within the dosing interval.

The term "$C_{min}$" is the minimum plasma concentration of the drug attained within the dosing interval.

The term "$C_{avg}$" as used herein, means the average plasma concentration of the drug within the dosing interval.

As used herein, the term "% Fluctuation Index" is expressed as $[\{C_{max} - C_{min}\}/C_{avg}]*100$.

As used herein, the term "$T_{max}$" is the time period which elapses after administration of the dosage form at which the plasma concentration of the drug attains the highest plasma concentration within the dosing interval.

As used herein, the term "modified release", "extended release", "sustained release" and "controlled release" are used to define the characteristic of a dosage form such that the release of the active ingredient component is slow and occurs over a period of time substantially longer than a corresponding rapid or immediate release counterpart.

As used herein, the term "rapid-absorption modified release" is used in relation to the dosage form of the present invention wherein although the release of the active ingredient is slow and occurs over a prolonged period of time, the compositions of the invention enable an enhanced absorption of the released active ingredient thus providing a faster rate of absorption than what is intrinsically expected. This therapeutic modality will effectively potentiate insulin action in patients with insulin-related disorders such as diabetes, pre-diabetes, impaired glucose tolerance or in healthy individuals predisposed to developing insulin-related disorders in a manner that mimics the insulin action of a non-diabetic individual. More specifically, the present invention relates to a rapid-absorption modified release oral dosage composition comprising an insulin-sensitizing oral hypoglycemic agent, for example, a biguanide such as metformin, phenformin or buformin or a pharmaceutically acceptable salt thereof such as metformin hydrochloride or the metformin salts described in U.S. Pat. Nos. 3,957,853 and 4,080,472.

By the term "amphipathic ionic compound" or "amphiphilic ionic compound" it is meant any compound, synthetic or otherwise, whose molecules or ions have a certain affinity for both polar and non-polar solvents. As used herein, the term "amphipathic compounds" is meant to be synonymous with the term "amphiphilic compounds".

The "critical micelle concentration" (CMC) defines the minimum amount of amphipathic compound (e.g. surfactant) required to form a micelle-phase in a particular solvent, and may be considered to represent the solubility of the surfactant monomer in that solvent.

The "critical reverse micelle concentration" (CrMC) as used herein defines the minimum amount of amphipathic compound (e.g. surfactant) required to form the reverse micelle phase in a particular solvent containing specific ions.

By the term "ionic monomer" it is meant cationic and anionic monomers, i.e. monomers wherein the part of the monomer molecule containing an ethylenically unsaturated group has a positive or negative charge, respectively.

Evaluation of Glucose Excursions

Glycemic excursions can be defined as an incremental rise in blood glucose values above fasting or basal pre-meal levels. The net values of glucose excursions are a consequence of endogenous contributions from processes such as gluconeogenesis and glycogenolysis as well as exogenous contribution from carbohydrate metabolism. Although the major contribution to most glucose excursions are from meal-related carbohydrate challenge, significant contributions due to one or more metabolic defects can also exaggerate the contributions from endogenous processes especially in diabetic individuals.

Investigations of hyperglycemia as a result of insulin-related disorders must address overall glucose disposal as a function of both kinetics (rate) and thermodynamics (extent) of the disposal. A useful and established index correlated to the extent of glucose disposal is fasting blood glucose and glycated hemoglobin (HbA1c). These indices are useful measures of overall glucose control—a thermodynamic function. Assessment of postprandial glucose excursions throughout the day and over a series of meal challenges is a dynamic process and a kinetic function that requires multiple sampling and evaluation of elevated blood glucose levels above a fasting or pre-meal baseline.

There is no universally 'right' or 'wrong' way to measure blood glucose responses. Different methods are required for different purposes. For example, to determine whether a new treatment for diabetes reduces blood glucose concentrations, total blood glucose AUC, a measure of average concentrations over time, may be indicative of that therapeutic outcome. However to determine if a new treatment reduces blood glucose excursions, total positive incremental AUC (iAUC) is preferred since glucose excursions is a measure of change, above a baseline, over time. Some investigators have used the concept of incremental AUC (iAUC) to evaluate hyperglycemia in diabetic states and gleaned valuable insights. For instance, Monnier et al (*Diabetes Care* 2003; 26:881-5: *Contributions of fasting and postprandial plasma glucose increments to the overall diurnal hyperglycemia of Type 2 and diabetic patients*.) investigated the contributions of postprandial and fasting glucose increments to overall hyperglycemia in patients with Type 2 used iAUC to delineate the discrete and discernible contributions made by these two disparate, but important sources of blood glucose increases to the overall diurnal hyperglycemia. In another study, Rassam et al (*Diabetes Care* 1999; 22:133-6: *Optimal administration of Lispro® Insulin in hyperglycemic Type I diabetes*.) applied the concept of iAUC to investigate the effect of dosing schedule of the drug Lispro® (insulin analog) on the development of hyperglycemia in patients with Type I diabetes. They were able to demonstrate that the application of iAUC provided a powerful tool in discerning significant differences in the observed hyperglycemic excursions leading to their recommendation of a more appropriate dosing schedule of the drug in hyperglycemic patients.

The positive iAUC, ignoring any areas below the baseline, for the blood glucose values over a period of time after meal challenge has been described and calculated according to the method of Wolever et al. (*British Journal of Nutrition* (2004), 91, 295-300: *Effect of blood sampling schedule and method of calculating the area under the curve on validity and precision of glycemic index values*) and is an appropriate measure of postprandial glucose excursions. Equation 1 provides the formula for determination of iAUC. This method allows for a more sensitive evaluation of true glycemic excursions at multiple time points while discounting non-excursion related blood glucose values, i.e. values below fasting baseline.

Equation 1: Assuming that at times $t_0, t_1, \ldots t_n$ the blood analyte concentrations for glucose (designated as G) are $G_0, G_1, \ldots G_n$, respectively,

X=1

AUC=$EA_x$ where $A_x$=the AUC for the $x^{th}$ time interval and the $x^{th}$ time interval is the interval between times $t_{(x-1)}$ and $t_x$.

For the first time interval (i.e. x=1):

If $G_1 > G_0$, $A_1 = (G_1 - G_0) \times (t_1 - t_0)/2$ otherwise, $A_1 = 0$

For other time intervals (ie. x>1):

If $G_x > G_0$ and $G_{(x-1)} > G_0$, $A_x = \{[(G_x - G_0)/2] + (G_{(x-1)} - G_0)/2\} \times (t_x - t_{(x-1)})$ If $G_x > G_0$ and $G_{(x-1)} < G_0$, $A_x = [(G_x - G_0)2/(G_x - G_{(x-1)})] \times (t_x - t_{(x-1)})/2$ If $G_x < G_0$ and $G_{(x-1)} > G_0$, $A_x = [G_{(x-1)} - G_0)2/(G_{(x-1)} - G_x)] \times (t_x - t_{(x-1)})/2$ If $G_x < G_0$ and $G_{(x-1)} < G_0$, $A_x = 0$ There are several therapeutic remedies aimed at the treatment of insulin-related disorders, such as diabetes mellitus. The mainstays of drug treatment are the oral anti-diabetic agents. Insulin is usually reserved for patients who do not achieve fasting plasma glucose or $HbA1_C$ goals with or cannot tolerate the oral anti-diabetic agents.

Although insulin therapy has been deemed the most effective for reducing postprandial glucose excursions and hyperglycemia, a common problem with insulin therapy is that insulin doses sufficient to control prandial glucose loads can produce elevated glucose elimination rates for extended intervals that can persist after the meal, leading to postprandial hypoglycemia. In addition, insulin therapy does require several daily injections that are inconvenient for the patients. The alternative therapy is the oral hypoglycemic agents (OHA's).

There are 5 classes of oral hypoglycemic agents available; sulfonylureas, biguanides, alpha-glucosidase inhibitors, thiazolidinediones, and nonsulfonylurea secretagogues. They have differences and similarities with respect to their pharmacology and role in diabetes. The biguanide metformin is the more widely prescribed of the OHA's and generally deemed to be safer for the treatment and management of Type 2 diabetes mellitus since there is no risk of hypoglycemia associated with its use.

Current metformin therapy modalities can reduce blood glucose levels by primarily sensitizing second-phase insulin release in response in meal challenge but do not possess the pharmacokinetic attributes necessary to effectively sensitize basal and first-phase insulin. Thus it is reasonable to hypothesize that adequate sensitization of basal insulin and/or impaired first-phase insulin in Type 2 diabetic patients is essential for eliciting early response to the impending hyperglycemia and glucose excursions from a meal challenge. As a result, further advantages will be realized in diabetics who retain some ability to produce insulin in that their endogenous second-phase and basal insulin will also be potentiated by metformin, increasing the effectiveness of that limited insulin and reducing pancreatic stress.

It has been generally assumed that the rate of glucose elimination at a point in time is simply a function of insulin concentration at that point in time. In point of fact, the glucose elimination rate achieved by any particular glucose load is influenced by prior insulin concentrations, kinetics of insulin, tissue distribution and overall sensitized state of available insulin. Thus, glucose elimination rate is potentiated not only by previous high insulin levels but also when the available insulin is adequately distributed and sensitized in the hepatocytes and peripheral tissues. For any given glucose load and physiologically available insulin concentration either produced or released in response to the glucose load, the glucose elimination rate is greater when the subject has experienced, in a preceding time interval, either a high insulin concentration in the hepatocytes and peripheral tissues capable of facilitating glucose disposal, or one that has been adequately sensitized in the same tissues. Without wishing to be bound by theory, the method of the present invention provides adequate and timely sensitization of insulin by insulin-sensitizing oral hypoglycemic agents, which can sensitize and potentiate the effect of both basal and secreted insulin in the tissues and that this potentiation drives the glucose elimination rate to maximum much more quickly and continues over a prolonged period of time normally prone to glucose excursions due to new glucose loads. An initial early sensitization of both basal and secreted insulin to peripheral tissues and hepatocytes by oral hypoglycemic agents may prepare such tissues for rapid glucose elimination in response to glucose loads.

A common problem with current metformin therapy is that metformin doses sufficient to control and reduce hyperglycemia under conditions of current use in clinical practice do not produce the desired glucose elimination rates that can efficiently treat post meal hyperglycemia and efficiently reduce postprandial glucose excursions over extended postprandial intervals. Due to unbearable gastro-intestinal related side effects and discomforts such as nausea, vomiting and flatulence associated with its use, metformin is prescribed to be taken with meals. According to the prescription product monograph of Glucophage® and Glucophage® XR by Bristol Myers Squibb, June 2006 "GLUCOPHAGE should be given in divided doses with meals while GLUCOPHAGE XR should generally be given once daily with the evening meal. GLUCOPHAGE or GLUCOPHAGE XR should be started at a low dose, with gradual dose escalation, both to reduce gastrointestinal side effects and to permit identification of the minimum dose." It further states that "the therapeutic goal should be to decrease both fasting plasma glucose and glycosylated hemoglobin levels to normal or near normal by using the lowest effective dose of GLUCOPHAGE or GLUCOPHAGE XR, either when used as monotherapy or in combination with sulfonylurea or insulin."

Following the safe use and administration of metformin with meals as currently prescribed in clinical practice, the increase in blood levels of metformin after oral administration, is significantly slower than what is necessary to effectively illicit physiologic response to prandial glucose elevation seen in normal and Type 2 diabetic individuals.

While the immediate release metformin (e.g. Glucophage®) produces a therapeutic profile that results in a higher peak plasma concentration of the drug than the extended or controlled release counterparts (e.g. Glucophage® XR), that rate of absorption and dosing intervals may be too slow and inefficient to effectively reduce postprandial glucose excursion episodes over the course of a normal day. Although the extended release metformin (e.g. Glucophage® XR) proffers the benefits of a once-daily administration, reduced gastrointestinal side effects and improved patient compliance, the resultant therapeutic profiles produces a lower and inefficient rate of absorption and peak plasma concentration that is both too slow and too low to be effective for the reduction of glucose excursions and postprandial hyperglycemia.

Another problem with current metformin therapy is the known food-effect propensity of both immediate release and extended release formulations. According to the drug monographs by Bristol Myers Squibb, June 2006 "Food decreases the extent of and slightly delays the absorption of metformin, as shown by approximately a 40% lower mean peak plasma concentration ($C_{max}$), a 25% lower area under the plasma concentration versus time curve (AUC), and a 35 minute prolongation of time to peak plasma concentration ($T_{max}$) following administration of a single 850 mg tablet of metformin with food, compared to the same tablet strength administered fasting." With respect to the food-effect propensity of the extended release formulation the monograph states that "Although the extent of metformin absorption (as measured by AUC) from the GLUCOPHAGE XR tablet increased by approximately 50% when given with food, there was no effect of food on $C_{max}$ and $T_{max}$ of metformin. Both high and low fat meals had the same effect on the pharmacokinetics of GLUCOPHAGE XR."

Therefore, metformin compositions and methods of treatment, which result in a more rapid rise in blood metformin levels with extended absorption of therapeutically significant concentrations over a physiologically relevant time frame, and which distribute metformin more efficiently within target tissues (e.g. hepatocytes and peripheral tissues), will result in a more physiologically synchronized means of sensitizing insulin and achieve maximal glucose elimination rates.

Such metformin compositions will improve upon the therapeutic effect of the conventional immediate release metformin without the adverse effects and with the benefits of the once-daily extended release metformin. The dual property will have the effect of early and timely sensitization of insulin in the hepatocytes and subsequently in the peripheral tissues over intervals that will translate to mimicking normal insulin response through potentiation of endogenous basal and secreted insulin thereby reducing risks of post-prandial hyperglycemia and glucose excursions. In addition, it will be advantageous both in therapeutic effectiveness and patient compliance for such compositions to be without the disadvantageous food effect of current metformin therapy. The lack of food effect will assure consistent performance of the new metformin composition and therapy.

When the oral modified release metformin composition of the present invention, once-daily GlycoBien® CR 1000 mg, is administered shortly before the beginning of a meal, blood glucose levels and glucose excursions after the meals are more significantly reduced and tightly controlled than if the same subjects were administered a prior art extended release metformin composition, Glucophage XR 1000 mg taken with meals as routinely prescribed in clinical practice. The aforementioned comparative study subjects were fed the same standardized meals and glycemic load over breakfast, lunch, dinner and snack. Glucose excursions as measured by positive incremental area under the glucose plasma time curve (iAUC) over an entire 24 hour period and over each meal period were significantly blunted by the metformin composition of the present invention compared with the prior art composition despite very similar total drug exposure.

Additionally, in a separate study, when the oral modified release metformin composition of the present invention, once-daily GlycoBien® CR 1000 mg, is administered shortly before the beginning of a meal, blood glucose levels and glucose excursions after the meal were also more reduced and tightly controlled than if the same subjects were administered a prior art immediate release metformin composition, Glucophage 500 mg taken twice-daily with meals as routinely prescribed in clinical practice. Again, the subjects were fed the same standardized meals and glycemic load over breakfast, lunch, dinner and snack. Glucose excursions as measured by positive incremental area under the glucose plasma time curve (iAUC) over an entire 24 hour period and over each meal period were significantly blunted by the metformin composition of the present invention compared with the prior art composition despite very similar total drug exposure.

Through effective leveraging of the pre-meal administration of the drug and the advantage of the potentiating effects of a rapid and pronounced increase in metformin concentration followed by a prolonged extended therapeutic concentration over several hours, together with the preferential distribution of the drug in hepatic tissues, a metformin therapy and treatment methodology with a therapeutic profile that mimics physiological response to glucose load can offer superior glucose control and several advantages over conventional therapy in the treatment and amelioration of glucose excursions.

The superior blood glucose control can be appreciated as reduced exposure to (elevated) glucose excursions (iAUC) compared to any reductions achievable by conventional metformin therapy(ies), reduced levels of HbA1c (glycosylated hemoglobin), virtually no risk or incidence of hypoglycemia, and reduced variability of response to treatment compared with conventional metformin therapy(ies).

Such metformin composition is preferably administered once-daily within a few minutes before commencing a breakfast meal, and unlike the more slowly absorbed prior art extended release metformin compositions, which are usually taken after a dinner meal, is rapidly absorbed faster than an immediate release drug taken with meals and maintained a sustained therapeutically effective concentration of the drug over an extended time frame akin to that of an extended release drug.

Another problem with current metformin treatment is the disadvantageous food effect pharmacokinetics that alter the absorption and achievable maximum plasma concentration of the drug as the dietary state of the patient changes. This food effect property can render the therapeutic performance of the drug inconsistent within each patient and invariably ineffective as an intervention for ameliorating postprandial glucose excursions. In a crossover comparative food-effect bioavailability study (FIG. 6) the pharmacokinetics of the modified release metformin composition of the present invention, once-daily GlycoBien® CR 1000 mg, administered under a fasted state and after a high and low fat meals, the critical pharmacokinetics parameters; $C_{max}$, AUC, and $T_{max}$. were not significantly different. Thus, the modified release metformin composition of the present invention does not exhibit the disadvantageous food effect pharmacokinetics that is well known and documented fro the conventional prior art metformin compositions.

Compositions and methods of preparing modified release metformin suitable for a once daily administration before meals and that can proffer the desired pharmacokinetic features of the present invention are disclosed in a Canadian Patent No. 2,468,788 and pending U.S. Patent Application Publication No. 2005/0255156 entitled "Reverse-micellar Drug Delivery System for Controlled Transportation and Enhanced Absorption of Agents".

GlycoBien® CR refers to a modified release metformin composition based on the Reverse-Micellar Drug Delivery System for Controlled Transportation and Enhanced Absorption of Agents, which is suitable for a once-daily oral administration before meals.

Treatment with GlycoBien® CR, by once-daily oral administration before breakfast, leads to serum metformin levels that rise more rapidly than the conventional immediate release metformin (e.g. Glucophage®) or extended release metformin (e.g. Glucophage® XR) taken with meals as routinely prescribed in clinical practice, such early rise and large plasma concentrations of metformin will effectively sensitize basal and first-phase secreted insulin action at the peripheral tissues, and will more closely approximate the kinetics of insulin response to meal-associated glucose rise in normal individuals. Additionally, it is believed that the composition of the present invention improves the distribution of metformin in the hepatic and peripheral tissues. As a result of these beneficial attributes, it is expected that postprandial glycemic excursions will be substantially reduced after GlycoBien® CR therapy in the post-meal periods compared with conventional immediate release metformin taken twice-daily or the extended release metformin taken once daily as prescribed in clinical practice.

In crossover comparative pharmacokinetic-pharmacodynamic studies in healthy subjects fed glycemic load-standardized meals, and administered the same total daily dose of metformin (FIG. 12A and FIG. 12B), the total daily average glucose disposal (glucose $AUC_{0-24}$) and daily average insulin secretion (insulin $AUC_{0-24}$) are similar whether the subjects have been administered metformin composition of the present invention (GlycoBien® CR), or prior art immediate release metformin (Glucophage®), however the daily post-meal excursions from normal blood glucose levels are significantly less with GlycoBien® CR than with the prior art metformin therapy.

Therefore, use of the new treatment modality and delivery features of metformin of the present invention results in an insulin action kinetics that approximates the expected response of healthy individuals, which allows patients with diabetes or impaired glucose tolerance to achieve greater control over their overall daily blood glucose and daily glucose excursion levels during post-meal periods.

The ability of the present invention to substantially reduce post-meal glucose excursions may have additional benefits to the general health of diabetics, impaired glucose tolerant individuals and otherwise healthy subjects, who are predisposed to developing impaired glucose tolerance or diabetes. Excessive post-meal glucose excursions are linked to atherosclerosis and diabetic vascular disease, a complication of diabetes that affects the eye, kidney and peripheral autonomic nervous systems. Therefore, the treatment methods and metformin compositions according to the present invention provides superior control of blood glucose levels and glucose excursions leading to immediate short-term and better long-term management of diabetic symptoms and overall health of diabetic patients and healthy individuals predisposed to developing diabetes.

The once-a-day metformin composition and therapy of the present invention may be used concomitantly with a sulfonylurea or a glitazone, when diet and monotherapy with the sulfonylurea or glitazone alone do not result in adequate glycemic control.

The mean % fluctuation index of the dosage form of the present invention may be from about 250% to about 260%, or from about 252% to about 256%. In certain examples of the present invention which exhibit a higher mean fluctuation index in the plasma than an equivalent dose of an immediate release reference standard composition administered as two equal divided doses, the ratio of the mean fluctuation index between the dosage form and the immediate release composition is about 12:1, about 11:1, or about 11.6:1.

The modified release metformin composition of the present invention, which includes an amphipathic ionic compound having a net charge that is opposite to that of the polar ionizable insulin-sensitizing oral hypoglycemic agent is similar to the pharmaceutical composition generically described in U.S. Patent Application Publication No. 2005/0255156 and Canadian Patent No. 2,468,788. In a particular example, the pharmaceutical composition of the present invention is GlycoBien® CR1000 mg; a once-daily rapid-absorption modified release metformin hydrochloride bi-layer tablet.

Anionic, cationic or zwitterionic surfactants may be employed as the amphipathic compound in the pharmaceutical compositions of the present invention.

Examples of anionic surfactants which may be employed by the present invention include, but are not limited to surfactants which exhibit favourable packing geometry of the surfactant molecule in the interfacial area, such as, but not limited to sodium dodecyl sulphate (SDS) and sodium bis(2-ethylhexyl) sulfosuccinate (AOT). Other anionic surfactants which may be employed include, but are not limited to alkali metal sulphates, such as sodium or potassium dodecyl sulphate, sodium octadecylsulphate, alkali metal sulphonates, such as alkali metal salts of benzene sulphonates, naphthalene sulphonates and, dialkysulphosuccinates. In a further example, the anionic surfactant is an alkali metal sulphonate, for example, but not limited to an alkali metal salt of benzene sulphonate, naphthalene sulphonate and dialkysulphosuccinate.

Cationic surfactants which may be employed by the present invention include, but are not limited to didodecyl dimethyl ammonium bromide (DDAB), cetyltriammonium bromide (CTAB), cetylpyridinium bromide (CPB), didodecyl dimethyl ammonium bromide, (DDAB), dodecyl trimethyl ammonium chloride (DOTAC), sodium perfluorononanoate (SPFN), and hexadecyl trimethyl ammonium bromide. However, any cationic surfactant which is capable of forming reverse micelles may be employed in pharmaceutical compositions of the present invention.

As would be evident to someone of skill in the art, it is generally preferred that the surfactant or surfactants employed in the pharmaceutical compostions of the present invention be cleared for human ingestion. Therefore, surfactants with a low toxicity are preferred. For example, but not wishing to be limiting in any manner, surfactants having an $LD_{50}$ exceeding about 10 g/kg to about 15 g/kg are preferred. The absence of other side effects is also desirable. Although surfactants which have already been approved for human ingestion are preferred, other surfactants may be employed in the pharmaceutical compositions of the present invention.

At surfactant concentrations well above the CMC any small amounts of monomeric surfactant (and perhaps small pre-micellar surfactant aggregates) exists in equilibrium with the bulk of the surfactant in micellar aggregates. The solubility of surfactant monomer in a particular solvent is dependent on specific solvent-solute forces. Without wishing to be bound by theory, the dominant intermolecular interactions between polar surfactant, and alkane solvent, molecules are thought to be dipole-induced dipole, and the induced dipole-induced dipole, forces.

The capacity of ionic monomers to form inverted micelles can be determined by standard tests known in the art for determining critical micelle concentration (CMC). As is known to one skilled in the art, some of the properties of a surfactant solution, such as refractive index, light scattering, interfacial tension, viscosity, dye solubilization and absorption of fluorescent substance usually vary linearly with increasing concentration up to the CMC, at which point there is a break or change in one or more of these properties (Encyclopaedia of Chemical Technology, Kirk-Othmer—3rd. ed. Vol. 22, A Wiley Interscience Publication—New York (1983) Page 354).

Formation of Reverse Micelles

Reverse micelles have a polar core, with solvent properties dependent upon the [water]/[surfactant] ratio (W), which can solvate highly polar water soluble compounds (e.g. hydrophilic substances, such as proteins, enzymes, ionised drugs, chemical catalysts and initiators) and sometimes even normally insoluble amphiphilic compounds. At low W values, the water in the micelle is highly structured due to its association with the ionic groups on the surfactant molecule and the counter ion core. The environment in the micelle core resembles that of an ionic fluid due to the large counter ion concentration. At larger W values, the swollen micelles (or microemulsions) are thought to have a free water core which provides a distinct third solvent environment and which approaches the properties of bulk water. Certain enzymes and polar compounds are only solubilized by reverse micelles swollen by large amounts of water, (W greater than about 10).

As described in more detail below, and without wishing to be bound by theory, when ionic anphiphiles are introduced into a hydrophilic fluid, and provided the concentration of the amphiphile is at or above their intrinsic CMC values, aggregation occurs with the formation of micelles. The aggregate composition in the micelles are oriented such that the hydrocarbon chains face inward into the micelle to form their own lipophilic environment, while the polar regions surrounding the hydrocarbon core are associated with the polar molecules in the hydrophilic fluid continuous phase. The orientation of micellar aggregates in non-polar fluid environment is essentially reversed. The polar regions face inwards into the micelles while the hydrocarbon chains surrounding the core of the micelles interact with the non-polar molecules in the fluid environment.

When present in a liquid medium at low concentrations, the amphiphiles exist separately and are of such a size as to be sub-colloidal. As the concentration is increased, aggregation occurs over a narrow concentration range. These aggregates which are composed of several monomers are called micelles. The concentration of monomers at which micelles are formed is termed the Critical Micelle Concentration, or CMC.

It is well known in the art that ionic amphiphiles, such as anionic or cationic surfactants, produce micelles in hydrophilic solvents by forming a lipophilic core through aggregation of the hydrocarbon chain. Polar heads of these compounds surrounding the core of the micelles interact and associate with the polar molecules in the fluid environment. As described herein, it has been unexpectedly observed that reverse micelles with polar cores can exist in hydrophilic fluids, and that such reverse micelles and microemulsions have unique, useful properties that can provide for transportation and delivery of polar ionizable compounds across biological membranes.

Without wishing to be bound by theory, when ionic amphiphiles are introduced into a hydrophilic fluid media composed of polar molecules whose ionization characteristics results in molecular or ionic charges opposite to that of the amphiphilic polar heads, an association colloid may be formed with a reverse orientation to that which is ordinarily expected. The charged polar region of the amphiphile associates with the oppositely charged polar molecules or ions of the fluid environment. At a certain concentration of the amphiphile, association colloids may be formed. These colloids comprise reverse-micelles with a polar core comprising the oppositely charged ions or molecules in fluid media in association with the polar heads of the amphiphile. Such reverse-micelles are surrounded by the lipophilic regions of amphiphile in a colloidal internal phase and separated from the hydrophilic fluid continuous phase.

Hydrophilic drugs that are highly ionizable in a prevailing physiological environment such as the gastro-intestinal lumen are thought to be poorly absorbed in part due to their polarity and charges. While these groups of compounds are soluble in the aqueous physiological media of the GIT, they exhibit poor partition coefficients and low permeabilities across the membranes of the GIT. Several therapeutic agents belonging to these categories of compounds, sometimes referred in the art as Class III (high solubility, low permeability) biopharmaceutical compounds often show saturable absorption kinetics together with low bioavailabilities. The reverse-micelle delivery system of the present invention enhances GIT transmembrane transport and delivery of these compounds.

Once dissolved in the physiological fluid environment, polar agents exist primarily as charged ions or molecules. Reverse-micelles formed in these conditions are composed of bound agents in the core of the micelles, surrounded by lipophilic hydrocarbons. The bound ionised agents are thought to be encapsulated in spherical colloidal reverse-micelles. These reverse micelle colloids partition across the lipophilic mucosal membranes of the GIT—thus acting as transport carriers for the therapeutic agents. Once partitioned across the lipophilic membranes, the reverse micelles disassociate as the concentration within the membrane falls below the CMC or CrMC and the interfacial tension drops in the lipophilic environment.

When the pharmaceutical compositions of the present invention come into contact with an external fluid of the environment, such as water or other biological fluid, a burst or gradual release of the ionic amphiphiles may occur. A concurrent release of the additional ionic amphiphiles and the oral hypoglycemic agent of interest follows. The ionic amphiphiles released dissolve in the aqueous fluid media forming ionic monomers. Upon release of the oral hypoglycemic agent(s) of interest, depending on the prevailing pH of the fluid environment and the pKa of the chemical compound, ionised molecules are formed. These ions carry permanent net charges opposite to that of the polar region of the ionic amphiphiles. The oppositely charged polar groups of the ionised agents of interest and amphiphiles attract each other. Without wishing to be bound by theory, at some point when sufficient ionic monomers of the amphiphile are attracted to the charged species in the aqueous fluid, aggregation and reverse micelle formation occurs. This point is believed to be the critical reverse micelle concentration (CrMC). These reverse micelles, in the aqueous fluid environment, eventually form colloidal microemulsions. In the human GIT, such reverse micelles are in direct contact with the lipophilic membranes of the absorbing mucosal cells. Due to the inherent lipophilicity of the outer surface of the reverse-micelles, they can partition rapidly into these membranes, thereby facilitating absorption.

Without wishing to be bound by theory, once the reverse micelles partition into the lipophilic membrane, the concentration of the amphiphilic molecule component of the reverse micelles diminish beneath the CMC or CrMC. The reverse micelles undergo disaggregation and release the oral hypoglycemic agent within their core. The kinetics of transport and transmembrane release of these agents may be essentially zero order or near about zero order.

The oral hypoglycemic agent used in the present invention may be a drug in a masked form such as a prodrug.

The pharmaceutical compositions of the present invention may be a pharmaceutical dosage form, which includes, but is not limited to, compressed tablets, granules, pellets, suspensions, extrusion spheroids or compacts obtained by direct compression, wet granulation, dry granulation, hot melt granulation, microencapsulation, spray drying, and extrusion methods as would be evident to one of skill in the art. Other solid dosage forms, such as hard gelatine capsules, can also be derived from dry blends, granulations, suspensions, spheroids, pellets, tablets and combinations therefrom, as are commonly known in the art.

In particular, the pharmaceutical compositions of the present invention may be one of the following types of dosage forms:
  i) a solid compact, a matrix-type solid compact, or a matrix-type extrusion spheroid comprising one, or more than one layer of a dry blended mixture or particulates containing an oral hypoglycemic agent, or microencapsulated oral hypoglycemic agent;
  ii) a capsule filled with a dry blended mixture or particulates containing an oral hypoglycemic agent, or microencapsulated oral hypoglycemic agent, or
  iii) a suspension of an oral hypoglycemic agent particulates containing an oral hypoglycemic agent, or microencapsulated oral hypoglycemic agent.

The delivery system may also be dispersed prior to administration to a subject so that the reverse micelles are formed in the dispersed mixture. For example, which is not to be considered limiting in any manner, the delivery system of the present invention may be dispersed within a liquid, and the liquid administered in an oral, or injectable form as required.

The delivery system of the present invention permits the release of one or more oral hypoglycemic agents of interest in a controlled manner, with a first-order, zero-order or near zero-order release kinetics, over a therapeutically practical time period.

The pharmaceutical dosage form may also include excipients as required, for example, but not limited to one or more viscosity enhancers, enteric polymers, pH-specific barrier polymers, diluents, anti-adherents, glidants, binders, plasticizers, solubilizers, channelling agents, stabilizers, compaction enhancers, wetting agents, fillers, buffering agents, flavourants, adsorbents, sweetening agents, colorants, lubricants, or a combination thereof.

Formulations incorporating solid dosage forms may further include one or more additional adjuvants, which can be chosen from those known in the art including flavours, colours, diluents, binders, plasticizers, fillers, surfactant, solubilizers, stabilizers, compaction enhancers, channelling agents, glidants, lubricants, coating polymers and anti-adherents.

The subject in need thereof may comprise any mammalian subject, for example, but not limited to a human subject.

The above description is not intended to limit the claimed invention in any manner, Furthermore, the discussed combination of features might not be absolutely necessary for the inventive solution.

The present invention will be further illustrated in the following examples. However, it is to be understood that these examples are for illustrative purposed only, and should not be used to limit the scope of the present invention in any manner.

EXAMPLES

Composition of Rapid-Absorption Modified Release Metformin Oral Dosage Form

A rapid-absorption modified release metformin composition of the present invention was prepared according to the formulation:

Composition of Rapid-Absorption Modified Release Metformin: GlycoBien® CR

Example-1

GlycoBien® CR 1000 mg

| INGREDIENT | GRADE | AMOUNT PER UNIT DOSE (MG/TAB) |
| --- | --- | --- |
| Metformin Hydrochloride | USP | 1000.00 |
| Cetyl Alcohol | NF | 149.99 |
| Gantrez ® MS955 | House | 6.81 |
| Sodium Lauryl Sulphate | USP | 175.96 |
| Hypromellose Phthalate | NF | 40.06 |
| FD & C Yellow #5 | House | 1.47 |

Example-2

GlycoBien® CR 500 mg

| INGREDIENT | GRADE | AMOUNT PER UNIT DOSE (MG/TAB) |
| --- | --- | --- |
| Metformin Hydrochloride | USP | 500.00 |
| Cetyl Alcohol | NF | 74.99 |
| Gantrez ® MS955 | House | 6.81 |
| Sodium Lauryl Sulphate | USP | 87.98 |
| Hypromellose Phthalate | NF | 20.03 |
| FD & C Yellow #5 | House | 0.74 |

Example-3

GlycoBien® CR PLACEBO

| INGREDIENT | GRADE | AMOUNT PER UNIT DOSE (MG/TAB) |
|---|---|---|
| Microcrystalline Cellulose PH101 | NF | 1000.00 |
| Cetyl Alcohol | NF | 149.99 |
| Gantrez® MS955 | House | 6.81 |
| Sodium Lauryl Sulphate | USP | 175.96 |
| Hypromellose Phthalate | NF | 40.06 |
| FD & C Yellow #5 | House | 1.47 |

Rapid-Absorption Modified Release metformin tablets—GlycoBien® CR and the corresponding Placebo tablets were prepared according to a three step manufacturing process as outlined below:

Step 1: Preparation of controlled release metformin or placebo granules: Metformin hydrochloride or microcrystalline cellulose was dispensed, milled (metformin granules only) and sieved (metformin and placebo granules). The milled powder was blended with sodium lauryl sulphate in a high shear mixer granulator using a Glatt TMG 6 L mixer-granulator. The homogeneous blend was granulated with cetyl alcohol @ ~40° C. in a heated jacketed high shear mixer granulator and cooled rapidly to ~30° C. or less. Denatured ethanol was used as necessary to reach granulation end-point. The granules were screened through mesh US#16, #20, or #40. Granules were allowed to air dry at room temperature or in a forced air oven at 19° C.-23° C.

Step 2: Preparation of delayed release mucoadhesive granules: Gantrez powder was granulated in a UniGlatt fluid-bed granulator with hydro-alcoholic solution of Hypromellose phthalate containing FD&C yellow #5. The granules were sieved through mesh #18 or #20. Sieved granules fractions were retained for further processing.

Step 3: Preparation of bi-layer Tablets: Homogeneous modified release granules were dispensed and adjusted for potency to contain 100% of the label claim. Using a bi-layer tablet press and a 19 mm×9 mm caplet or other suitable sized tooling, bi-layer tablets were compressed from the controlled release metformin granules on one layer (main primary layer) and the delayed release mucoadhesive granules on the second layer (minor secondary layer).

Dissolution Profile of GlycoBien® CR Bi-Layer Tablets

The dissolution profile (FIG. 1) and acceptance criteria of the bi-layer tablets tested with a USP apparatus 2 (paddle) @ 50 rpm, 37° C. and pH of 6.8 in phosphate buffer is as follows:

| Time (hr) | % drug released |
|---|---|
| 1.0 | Between 10-25% |
| 2.0 | Between 20-40% |
| 5.0 | Between 45-65% |
| 11.0 | Between 65-95% |
| 24.0 | Not less than 80% |

Clinical Trial Protocols

A series of clinical trials were conducted in healthy, non-diabetic male and female volunteers to determine and establish the bioavailability, comparative bioavailability, comparative pharmacokinetics-pharmacodynamics, and food effect pharmacokinetics of the new treatment regimens and metformin compositions of the present invention in comparison with prior art treatment regimens and compositions. The primary purpose was to establish the pharmacokinetic profile as well as provide clinical evidence of the superior pharmacodynamics and postprandial glucose excursion lowering attributes of the pharmaceutical composition of the present invention relative to prior art metformin compositions.

Conduct of the Study

Metformin has previously been established an effective drug for lowering blood glucose and $HbA1_C$ in the management and treatment of Type 2 diabetes. Although metformin has been observed to lower the 2-hr postprandial glucose excursion its effectiveness as a therapy for reducing meal-related postprandial glucose excursions over a period of time has not been established. Thus, its use in ameliorating medical risks associated with postprandial hyperglycemia and glucose excursion is not evident in the various existing metformin formulations and treatment regimens from the prior art. The salient aspect of this invention is the use of a new treatment regimen and novel composition of metformin for the effective control and reduction of postprandial glucose excursions over periods encompassing multiple meals daily.

Postprandial glucose excursions are prevalent in all humans in response to meals. These excursions are, however, adequately controlled to ensure that incidences of hyperglycemic excursions are not experienced. In diabetic patients, these excursions invariably become hyperglycemic. Due to several possible underlying factors responsible for hyperglycemia in diabetic patients and the primary need to reduce confounding from endogenous glucose metabolic dysglycemia; healthy subjects with normal insulin function are ideal for the study.

Thus, healthy subjects were selected as the appropriate models in these clinical trials in order to reduce variability due to disease conditions that may confound the comparative evaluation of the new treatment regimen and metformin compositions of the present invention against those of the prior art formulations.

Due to the fact that metformin as monotherapy has been proven to be effective in long term management of Type 2 diabetes through lowering $HbA1_C$ and fasting blood glucose, these indices are less relevant in the current clinical trials, which are focused on the effectiveness of reducing postprandial glucose excursions. Since glucose excursions are prevalent in both diabetic and non-diabetic individuals regardless of their $HbA1_C$ and fasting blood glucose levels, its is scientifically justified and more prudent to evaluate the pharmacokinetics and glucose excursion lowering pharmacodynamics of the metformin formulations in healthy subjects. While the inherent glucose excursion lowering propensity of healthy subjects is expected in the clinical studies, the use of placebo control baseline as a covariate in the analysis of significance, together with the use of a crossover study design and compulsory glycemic load-standardized meals throughout the study, will elicit the comparative treatment differences sought.

Subjects

The study was conducted with healthy male and female volunteers aged 18 to 55 years with normal body mass index (BMI: 18.5-26.0 $kg/m^2$) and body weight not more than ±15% of the ideal weight for the subject's height and frame as determined by the Table of Desirable Weights for Men and Women, recorded in pounds and inches.

Study protocols and subject Informed Consents were designed in accordance with the provision of International Convention on Harmonization (ICH) and Good Clinical Practices (GCP) and were approved by an Ethics Board prior to initiation of the study.

Figure 2:
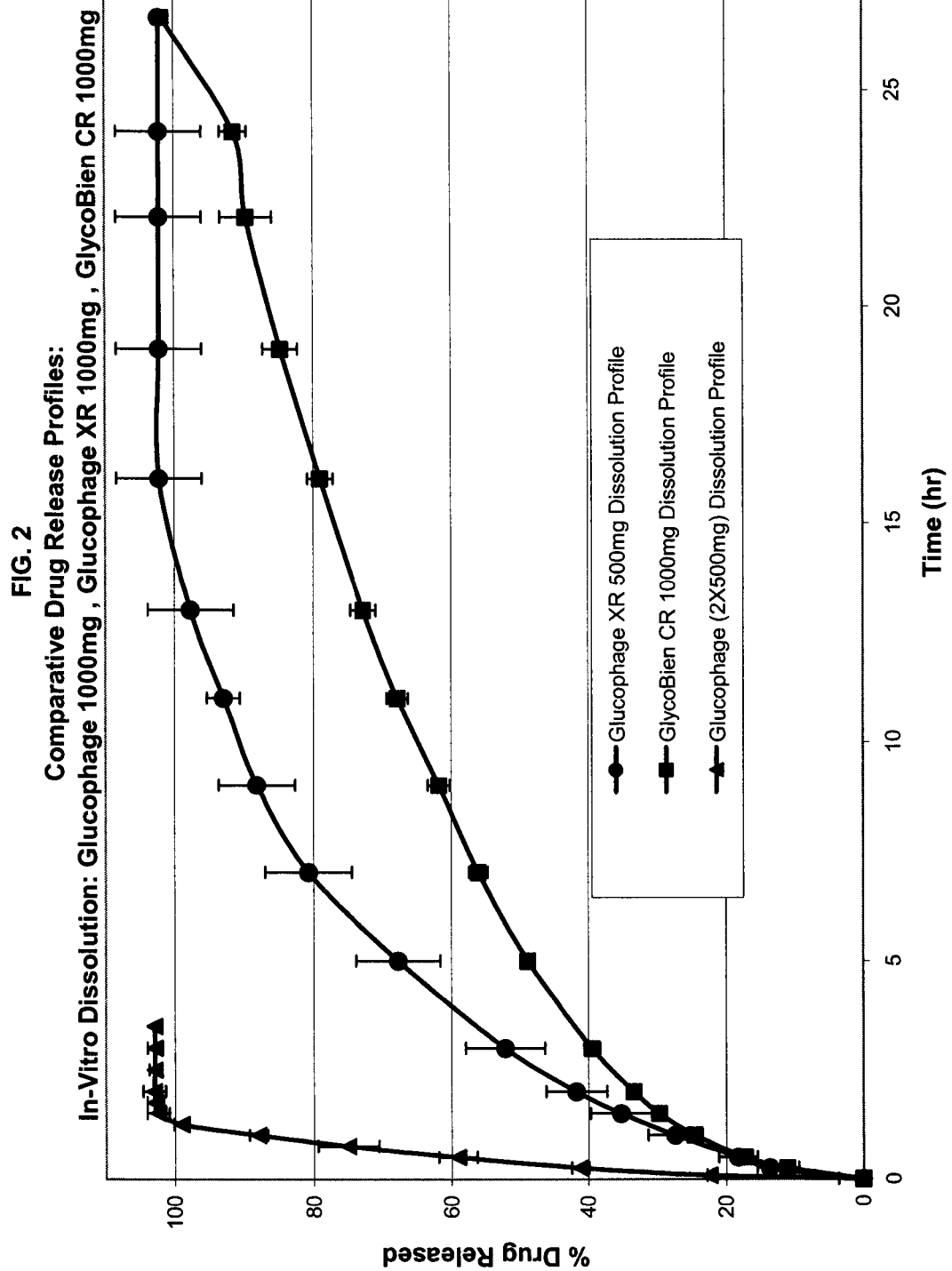
FIG. 2 illustrates comparative plots of dissolution profiles of GlycoBien® CR 1000 mg, Glucophage® XR (extended release metformin), Glucophage® (immediate release metformin) tested at a 50 rpm with a USP type II dissolution apparatus, in phosphate buffer, pH 6.8, at a temperature of 37° C. % drug released are mean values of metformin released over a period of time (hr).
Figure 9A:
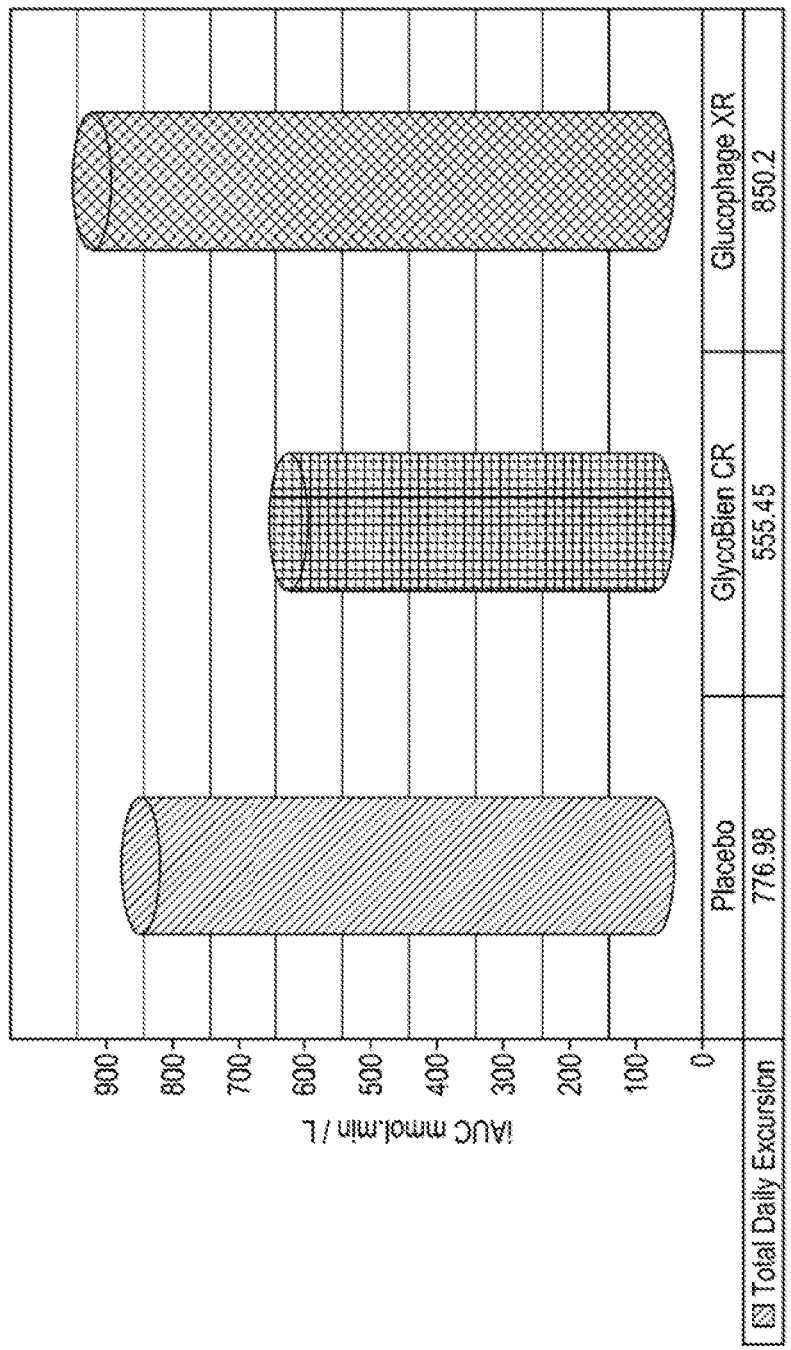
FIG. 9A illustrates comparative plots of daily postprandial plasma glycemic excursions (serum glucose iAUC$_{0-24}$) in thirteen (13) healthy male and female subjects fed glycemic-load standardized meals at Day-7 in a multi-dose crossover pharmacodynamics studies of treatments with Placebo, GlycoBien® CR 1000 mg taken before breakfast, and Glucophage® XR 1000 mg (2×500 mg) taken after evening dinner.

Inclusion criteria were good health, as judged by physical examination, vital signs (blood pressure between 100-140/60-90 mm Hg and heart rate between 55-99 beats/min) and 12-lead ECG. In addition, all subjects were determined to be non-diabetic with normal range of blood and urine biochemistry for liver function, kidney function, ketoacidosis and glycated hemoglobin. All subjects who received study medication or completed the study received a post-study medical examination and clinical biochemistry profile follow-up for liver function.

mg (2×500 mg). The geometric mean ratio of the extent of drug absorbed ($AUC_{0-\infty}$) and the maximum plasma concentration ($C_{max}$) are 0.99 and 0.96 respectively. The time to maximum concentration $T_{max}$ of the modified release test drug is prolonged by at least 30 minutes in comparison to the immediate release reference. This result show that although the in-vitro drug release from the rapid-absorption modified release metformin composition is extended in comparison to the immediate release drug (FIG. 2), the in-vivo absorption profile of the modified release composition ensures comparable extent of drug absorption.

TABLE 1

Mean (±SD, N = 25) values of Pharmacokinetic Parameters of metformin in a Crossover Bioavailability and Food Effect Study of GlycoBien ® CR and Glucophage in Healthy Subjects

| Treatment | $AUC_{0-\infty}$ (µg · hr/ml) | $C_{max}$ (µg/ml) | $T_{max}$ (hr) | Geometric Mean Ratio | |
|---|---|---|---|---|---|
| (A) Glucophage ® 1000 mg (taken 2 × 500 mg q.d. fasted) | 11.59 ± 3.16 | 1.94 ± 0.55 | 2.28 (1.0-4.0) | | |
| (B) GlycoBien ® CR 1000 mg (taken q.d. fasted) | 11.42 ± 2.90 | 1.86 ± 0.47 | 2.78 (1.5-4.0) | 0.99* | 0.96* |
| (C) GlycoBien ® CR 1000 mg (taken q.d. after high-fat breakfast) | 10.92 ± 2.32 | 1.48 ± 0.43 | 3.94 (1.5-6.0) | 0.96** | 0.80** |

*Ratio = B/A
**Ratio = C/B

Summary of Clinical Trials

Study 1: Fasted State Comparative Bioavailability of GlycoBien® CR 1000 mg and Glucophage® 1000 mg (Immediate Release Metformin)

The fasted state bioavailability of GlycoBien CR 1000 mg was compared with a marketed immediate release metformin—Glucophage (2×500 mg) as reference drug in a study titled: "Group 2: Comparative Bioavailability (fasted and fed) study involving Glucophage 1000 mg tablets (administered as 2×500 mg once daily) and Metformin 1000 mg extended release (new formulation) tablet given once daily". In this study twenty-six (26) male and female subjects enrolled for the study, one subject dropped-out for personal reasons and twenty-five (25) male and female subjects participated and completed the single-dose crossover fasted state bioavailability study design. The dose was administered after an overnight fast of approximately ten (10) hours and the subjects continued fasting for a further four (4) hours after dosing. Each treatment arm was separated by a seven (7) day washout period.

Venous blood samples for metformin analysis were obtained from subjects at 0.0 (pre-dose), and 1.0 hr., 1.5 hr., 2.0 hr., 2.5 hr., 3.0 hr., 4.0 hr., 5.0 hr., 6.0 hr., 7.0 hr., 8.0 hr., 9.0 hr., 10.0 hr., 12.0 hr., 14.0 hr., 16.0 hr., 20.0 hr., 24.0 hr., and 30.0 hr post-dose. Plasma concentrations of metformin were determined using a validated HPLC-UV method. The lower quantitation limit of this method is 25 ng/ml. Comparative mean plasma concentration versus time profiles for the test and reference drugs are shown in FIG. 4 and the mean values of the pharmacokinetic parameters of metformin obtained from the study are presented in Table 1.

Results

As shown in FIG. 4 and Table 1, the bioavailability, under fasting conditions, of a single oral dose of the modified release metformin of the present invention-GlycoBien® CR 1000 mg is comparable to the bioavailability of a single oral dose of immediate release metformin—Glucophage® 1000

Study: 2: Fasted State Comparative Single-Dose Bioavailability of GlycoBien CR 1000 mg, Glucophage 1000 mg (Immediate Release Metformin), and GlycoBien CR 2000 mg in Healthy Subjects In this three-treatment period study the fasted state bioavailability of GlycoBien® CR 1000 mg was compared with a marketed immediate release metformin, Glucophage® (2×500 mg) as reference drug and as well the dose proportionality of GlycoBien® CR 1000 mg was investigated by comparing the pharmacokinetics of a 1000 mg dose to a 2000 mg dose. The study titled: "Single Dose, Randomized, Open Label, Crossover, Comparative Bioavailability, and Dose Proportionality study involving GlycoBien® CR 1000 mg, and Glucophage® 1000 mg, and GlycoBien® CR 2000 mg in Healthy Male and Female Volunteers" involved a total of twenty-eight (28) healthy male and female subjects randomized to receive a single oral dose of GlycoBien® CR 1000 mg, Glucophage® 1000 mg (2×500 mg) or GlycoBien® CR 2000 mg (2×1000 mg) under fasting conditions in a crossover comparative bioavailability study design.

The dose was administered after an overnight fast of approximately ten (10) hours and the subjects continued fasting for a further four (4) hours after dosing. Each treatment arm was separated by a seven (7) day washout period. In this study, a total of two (2) subjects withdrew from the study; one subject withdrew for personal reasons and the other due to side effects of the immediate release Glucophage® (2×500 mg). Thus twenty-six subjects (14 males and 12 females) completed the study.

Venous blood samples for metformin analysis were obtained from subjects at 0.0 (pre-dose), and 0.5 hr., 1.0 hr., 1.5 hr., 2.0 hr., 2.5 hr., 3.0 hr., 3.5 hr., 4.0 hr., 4.5 hr., 5.0 hr., 6.0 hr., 7.0 hr., 8.0 hr., 9.0 hr., 10.0 hr., 12.0 hr., 14.0 hr., 16.0 hr., 18.0 hr., 20.0 hr., 24.0 hr., 30.0 hr., and 36.0 hr post-dose. Plasma concentrations of metformin were determined using a validated LC-MS-MS method. The lower quantitation limit of this method is 4 ng/ml. Mean plasma concentration versus time profiles are shown in FIG. 5 and the mean values of the pharmacokinetic parameters of metformin obtained from the study are presented in Table 2.

Results

As shown in FIG. 5 and Table 2, the bioavailability, under fasting conditions, of a single oral dose of the modified release metformin of the present invention-GlycoBien® CR 1000 mg is comparative to the bioavailability of a single oral dose of immediate release metformin e.g. Glucophage® 1000 mg (2×500 mg). The mean extent of metformin absorbed ($AUC_{0-\infty}$) and the peak plasma concentrations $C_{max}$ are similar as evidenced by the geometric mean ratios of 0.88 and 0.92 respectively. There was a 1.54 fold increase in $C_{max}$ and a 1.62 fold increase in $AUC_{O-\infty}$ as the dose of GlycoBien® CR was increased from 1000 mg to 2000 mg.

TABLE 2

Mean (±SD, N = 26) values of Pharmacokinetic Parameters of metformin in Comparative Bioavailability and Dose Proportionality Crossover Study of Healthy Subjects

| Treatment | $AUC_{0-\infty}$ (µg · hr/ml) | $C_{max}$ (µg/ml) | $T_{max}$ (hr) | Geometric Mean Ratio | |
|---|---|---|---|---|---|
| GlycoBien ® CR 1000 mg | 11.44 ± 2.34 | 1.85 ± 0.40 | 3.12 (1.0-4.5) | 0.88 | 0.92* |
| GLUCOPHAGE ® (2 × 500 mg) | 13.03 ± 3.25 | 2.01 ± 0.47 | 2.83 (1.0-5.0) | | |
| GlycoBien ® CR (2 × 1000 mg) | 18.51 ± 4.39 | 2.85 ± 0.62 | 2.83 (1.0-4.5) | 1.62 | 1.54** |

*Ratio = GlycoBien CR/GLUCOPHAGE
**Ratio = GlycoBien CR 2000 mg/GlycoBien CR 1000 mg Study 3: Food-Effect Bioavailability of GlycoBien® CR 1000 mg This study investigated the food-effect bioavailability of GlycoBien® CR 1000 mg taken in the fed-state compared with GlycoBien® CR 1000 mg taken in the fasted state. In a study titled: "Group 2: Comparative Bioavailability (fasted and fed) study involving Glucophage® 1000 mg tablets (administered as 2×500 mg once daily) and Metformin 1000 mg extended release (new formulation) tablet given once daily", twenty-six (26) healthy male and female subjects participated in a single-dose crossover food-effect bioavailability study design. For the fasted arm of the study, a single dose of GlycoBien® CR 1000 mg was administered after an overnight fast of approximately ten (10) hours and the subjects continued fasting for a further four (4) hours after dosing. The fed arms were dosed after consumption of a high calorie (55% high-fat) breakfast. This crossover fed bioavailability study was designed to determine effect of high fat meal on the bioavailability of the modified release metformin composition of the invention, GlycoBien® CR 1000 mg compared its bioavailability in the extended fasted state. In this study one subject withdrew due to personal reasons, thus twenty-five (25) subjects completed the study.

Venous blood samples for metformin analysis were obtained from subjects at 0.0 (pre-dose), and 1.0 hr., 1.5 hr., 2.0 hr., 2.5 hr., 3.0 hr., 4.0 hr., 5.0 hr., 6.0 hr., 7.0 hr., 8.0 hr., 9.0 hr., 10.0 hr., 12.0 hr., 14.0 hr., 16.0 hr., 20.0 hr., 24.0 hr., and 30.0 hr post-dose. Plasma concentrations of metformin were determined using a validated HPLC-UV method. The lower quantitation limit of this method is 25 ng/ml. Comparative mean plasma concentration versus time profiles for the test and reference drugs are shown in FIG. 6 and the mean values of the pharmacokinetic parameters of metformin obtained from the study are presented in Table 1.

Results

As presented in Table 1, the bioavailability of a single oral dose of GlycoBien® CR 1000 mg is not significantly different in the high-fat fed compared to its bioavailability in the extended fasted state. The geometric mean ratios of the total drug exposure $AUC_{0-\infty}$ and the peak plasma concentration $C_{max}$ are 0.96 and 0.80, respectively. The extent of drug absorbed is more comparable than the peak concentration attained. The high fat-fed condition slightly reduces the peak plasma concentration.

Study 4: Food-Effect Bioavailability of Glycobien® CR 1000 Mg after Low-Fat and High-Fat Meals This study investigates the food-effect bioavailability of GlycoBien® CR 1000 mg taken in the low fat and high fat-fed states. In a study titled: "Single Dose, Three-Treatment, Randomized, Open Label, Crossover, and "Food-Effect" Bioavailability of GlycoBien® CR 1000 mg (metformin hydrochloride) in Healthy Male and Female Volunteers", a total of twenty-eight (28) healthy male and female subjects were randomized to receive a single oral dose of GlycoBien® CR 1000 mg in the fasted state and after a high fat (55% fat) and low fat (25% fat) according to the American Heart Association (AHA) criteria for low fat. This comparative crossover fed bioavailability study was designed to determine the effect of high and low fat on the bioavailability of the modified release metformin composition of the present invention, GlycoBien® CR 1000 mg.

Subjects enrolled in the study were fasted overnight for approximately ten (10) hours and the dose was administered after a high-fat or low-fat breakfast. The drug was administered within 5 minutes after complete consumption of the respective high-fat or low-fat breakfast meals. Each treatment period was separated by a seven (7) day washout period. In this study, six (6) subjects withdrew from the study due to personal reasons. Thus, twenty-two (22) subjects (13 males and 9 females) completed the study.

Venous blood samples for metformin analysis were obtained from subjects at 0.0 (pre-dose), and 0.5 hr., 1.0 hr., 1.5 hr., 2.0 hr., 2.5 hr., 3.0 hr., 3.5 hr., 4.0 hr., 4.5 hr., 5.0 hr., 6.0 hr., 7.0 hr., 8.0 hr., 9.0 hr., 10.0 hr., 12.0 hr., 14.0 hr., 16.0 hr., 18.0 hr., 20.0 hr., 24.0 hr., 30.0 hr., and 36.0 hr. Post-dose. Plasma concentrations of metformin were determined using a validated LC-MS-MS method. The lower quantitation limit of this method was 4 ng/ml. Mean plasma concentration profiles are shown in FIG. 7 and the mean values of the pharmacokinetic parameters of metformin obtained from the study are presented in Table 3.

Results

The bioavailability of a single oral dose of GlycoBien® CR 1000 mg is not significantly different in the low-fat (25% fat) fed compared to the high-fat (55% fat) fed states. As shown in FIG. 7 and Table 3, the extents of drug absorbed ($AUC_{0-\infty}$), peak plasma concentration ($C_{max}$) and time to attain peak plasma concentration ($T_{max}$) are similar. The geometric ratios of the mean values for the total drug exposure $AUC_{0-\infty}$ and the peak plasma concentration $C_{max}$ are 1.02 and 0.99 respectively. Thus, the bioavailability of a single oral dose of modified release metformin of the present invention is not significantly affected by fat or calorific content of the meals. This finding is significant given the fact that prior art metformin formulations are known to exhibit food effect pharmacokinetics, which most likely compromises the bioavailability and thus may affect the consistency of the therapeutic effect.

tained for a total of seven (7) days separated by a seven (7) day washout The seven (7) day treatment period comprised two confinement days (day 1 and day 7) and five (5) ambulatory days. During the ambulatory days, subjects were fed standardized meals after the breakfast dosing and before the dinner dosing according to their respective dosing regimens. In this study, two (2) subjects withdrew from the study due to personal reasons. Thus, fourteen (14) subjects (6 males and 8 females) completed the study.

During the one day placebo lead-in and day 1 single-dose treatment period, venous blood samples for metformin plasma and serum glucose analysis were obtained from subjects at 0.0 (pre-dose), and 0.5 hr., 1.5 hr., 2.5 hr., 3.5 hr., 4.5 hr., 5.5 hr., 6.5 hr., 7.5 hr., 8.5 hr., 9.5 hr., 10.5 hr., 11.5 hr., 12.5 hr., 13.5 hr., 15.0 hr., 16.0 hr., 18.0 hr., 20.0 hr., 24.0 hr post dose. During the five day ambulatory period, blood samples for metformin plasma analysis were further taken each time before the breakfast dosing or before the dinner meals related

TABLE 3

Mean (±SD, N = 26) values of Pharmacokinetic Parameters of metformin in Food Effect Bioavailability Crossover Study of GlycoBien ® CR in Healthy Subjects

| Treatment | $AUC_{0-\infty}$ (μg · hr/ml) | $C_{max}$ (μg/ml) | $T_{max}$ (hr) | Geometric Mean Ratio | |
|---|---|---|---|---|---|
| (A) GlycoBien ® CR 1000 mg (taken q.d. fasted) | 9.38 ± 2.39 | 1.29 ± 0.44 | 2.72 (0.5-5.0) | | |
| (B) GlycoBien ® CR 1000 mg (taken q.d. after low-fat breakfast) | 12.21 ± 2.54 | 1.66 ± 0.38 | 4.56 (2.5-6.0) | 1.30* | 1.29* |
| (C) GlycoBien ® CR 1000 mg (taken q.d. after high-fat breakfast) | 12.48 ± 2.57 | 1.64 ± 0.35 | 4.22 (2.0-6.0) | 1.02** | 0.99** |

*Ratio = B/A
**Ratio = C/B

Study 5A: Single-Dose and Multi-Dose Steady-State Comparative Pharmacokinetics and Pharmacodynamics of GlycoBien® CR, Glucophage® XR and Glucophage®

This study determined the steady-state pharmacokinetics of GlycoBien® CR after multiple dosing and investigated the propensity of GlycoBien®CR and the present new dosing regimen to reduce postprandial blood glucose excursions in comparison to Glucophage® XR as used in clinical practice.

In a study titled: "Open Label, Multi-Dose, Randomized, Crossover, Comparative Pharmacokinetics and Pharmacodynamic study involving GlycoBien® CR 1000 mg and Glucophage® XR 1000 mg, in Healthy Male and Female volunteers", a total of sixteen (16) healthy male and female subjects were enrolled in a one-day placebo lead-in period wherein each subject received one placebo tablet twice daily before breakfast and dinner. The subjects also received three glycemic load standardized meals for breakfast, lunch, dinner and snack. Following the placebo lead-in period, randomized subjects were administered either a single oral dose of GlycoBien® CR 1000 mg approximately 30 minutes before the glycemic load standardized breakfast or single oral dose of Glucophage® XR 1000 mg (taken 2×500 mg) approximately 5 minutes after the glycemic load standardized dinner in a two-period crossover study. During the placebo-lead in and each treatment period, subjects were fed the same glycemic load standardized meals for breakfast, lunch, dinner and snack. The dosing regimens per treatment period was mainto the dinner dosing. At steady-state, during the seventh day confinement, venous blood samples for metformin plasma and serum glucose analysis were obtained from subjects at 0.0 (pre-dose), and 0.5 hr., 1.5 hr., 2.5 hr., 3.5 hr., 4.5 hr., 5.5 hr., 6.5 hr., 7.5 hr., 8.5 hr., 9.5 hr., 10.5 hr., 11.5 hr., 12.5 hr., 13.5 hr., 15.0 hr., 16.0 hr., 18.0 hr., 20.0 hr., 24.0 hr., and 36.0 hr post dose.

Plasma concentrations of metformin were determined using a validated LC-MS-MS method. The lower quantitation limit of this method was 4.0 ng/ml. Mean plasma concentration profiles for the single and multi-dose steady-state pharmacokinetics are shown in FIG. 8A and FIG. 8B and the mean values of the pharmacokinetic parameters of metformin obtained from the study are presented in Table 6 and Table 7.

Serum concentrations of glucose were determined using a validated glucose oxidase method with a % CV of <5%. The positive incremental area under the blood glucose-concentration versus time curve (iAUC) over the meal periods breakfast, lunch and dinner were determined for each treatment period and compared with placebo baseline. The overall daily (24-hr) $iAUC_{0-24}$ were also determined for each treatment and compared with placebo baseline. Mean iAUC as an index of glucose excursions for the single-dose and multi-dose (steady-state) treatments are presented in FIG. 9A, FIG. 9B, FIG. 9C, FIG. 9D and Tables 4-5.

Results

The results of the pharmacokinetics analysis and the pharmacodynamic determinations as illustrated in FIGS. 8A and 8B and Tables 8 and 9 shows that GlycoBien® CR has a faster increase in blood metformin concentration, achieving a higher peak plasma concentration with a prolonged time to peak concentration compared to Glucophage® XR. Although the total amount of drug absorbed as determined by the plasma metformin $AUC_{0-24}$ are comparable, the effect on postprandial glucose excursion over a period of 24-hrs is more pronounced with GlycoBien® CR in comparison to Glucophage® XR. The results are summarized as follows:

Pharmacokinetics:

FIGS. 8A and 8B depict the comparative single-dose and steady-state pharmacokinetic profiles, respectively. It is evident that the profile of GlycoBien® CR 1000 mg taken once-daily before breakfast is distinctly different from that obtained for Glucophage® XR 1000 mg taken once-daily after dinner. The rate of absorption of metformin from GlycoBien® CR is faster than Glucophage® XR as evidenced by the higher mean peak plasma concentration ($C_{max}$) of 1.19 µg/L for GlycoBien® CR 1000 mg and 0.88 µg/L for Glucophage® XR 1000 mg (p-value <0.004). At steady-state, the $C_{max}$ for GlycoBien® CR 1000 mg and Glucophage® XR 1000 mg are 1.33 µg/L and 0.97 µg/L (p-value <0.001). After seven days of multi dosing, at steady state, the total amount of drug absorbed ($AUC_{ss}$) and the time to peak plasma concentration ($T_{max}$) are not significantly different.

Pharmacodynamics:

FIGS. 9A through 9D depict the comparative postprandial glucose excursion lowering over periods of breakfast, lunch and dinner and over the entire 24-hr period for the placebo, GlycoBien® CR and Glucophage® XR treatments. The postprandial blood glucose excursion lowering effect of GlycoBien® CR is substantially higher than that observed with Glucophage® XR. GlycoBien® CR produced a 28.5% lowering of 24-hr plasma glucose excursion ($iAUC_{0-24}$) compared with placebo baseline, while Glucophage® XR produced an increase of 9.42%. Thus GlycoBien® CR produced a net treatment difference of −34.67% (p-value <0.035) compared with Glucophage® XR.

TABLE 4

Mean ± SE, N = 14 values of Serum Glucose positive iAUC0-24 hr Pharmacodynamic Parameters of Daily Glucose Excursion after Single Dose Treatment in Healthy Subjects

| Treatment | $iAUC_{0-24}$ (mmol · min/L) | % Change from Placebo | Placebo Adjusted $\Delta iAUC_{0-24}$ (mmol · min/L) | **% Diff. | *p-value |
|---|---|---|---|---|---|
| Placebo (taken with meal) | 785.80 ± 108.80 | N/A | N/A | | |
| GlycoBien ® CR 1000 mg (taken q.d. before breakfast) | 579.54 ± 70.51 | −26.25 | −206.27 ± 103.38 | −33.71 | <0.05 |
| Glucophage ® XR (2 × 500 mg) (taken q.d. after dinner) | 874.61 ± 144.69 | 11.30 | 88.81 ± 116.86 | | |

*ANCOVA p-values with placebo as covariate
**Difference from Glucophage ® XR

TABLE 5

Mean ± SE, N = 13 values of Serum Glucose positive iAUC0-24 hr Pharmacodynamic Parameters of Daily Glucose Excursion after 7 Days Treatment in Healthy Subjects

| Treatment | $iAUC_{0-24}$ (mmol · min/L) | % Change from Placebo | Placebo Adjusted $\Delta iAUC_{0-24}$ (mmol · min/L) | **% Diff. | *p-value |
|---|---|---|---|---|---|
| Placebo (taken with meal) | 776.98 ± 117.13 | N/A | N/A | | |
| GlycoBien ® CR 1000 mg (taken q.d. before breakfast) | 555.45 ± 81.71 | −28.51 | −221.52 ± 107.38 | −34.67 | <0.035 |
| Glucophage ® XR (2 × 500 mg) (taken q.d.after dinner) | 850.2 ± 99.23 | 9.42 | 73.23 ± 106.64 | | |

*ANCOVA p-values with placebo as covariate
**Difference from Glucophage ® XR

TABLE 6

Single-Dose Pharmacokinetic Parameters
GlycoBien ® CR Vs. Extended Release Metformin (Glucophage ™XR)

| Parameters (N = 14) Mean ± SD | GlycoBien ® CR 1000 mg (administered q.d. before breakfast) | Glucophage ™XR (2 × 500 mg) (administered q.d. after dinner) | p-value |
|---|---|---|---|
| $C_{max}$ (µg/L) | 1.19 ± 0.25 | 0.88 ± 0.26 | <0.004 |
| $T_{max}$ (hr) | 4 (1.5-6.5) | 7 (4.5-13.5) | NS |
| $AUC_{0-24}$ (µg · hr/L) | 10.15 ± 1.87 | 10.64 ± 2.67 | NS |

TABLE 7

Multi-Dose Steady-State Pharmacokinetic Parameters at Day 7
GlycoBien ® CR Vs. Extended Release Metformin (Glucophage ™XR)

| Parameters (N = 13) Mean ± SD | GlycoBien ® CR 1000 mg (administered q.d. before breakfast) | Glucophage ™XR (2 × 500 mg) (administered q.d. after dinner) | p-value |
|---|---|---|---|
| $C_{max}$ (µg/L) | 1.33 ± 0.29 | 0.97 ± 0.22 | <0.0011 |
| $T_{max}$ (hr) | 5.64 (1.5-7.5) | 6.57 (3.5-12.5) | NS |
| $AUC_{0-24}$ (µg · hr/L) | 11.91 ± 2.57 | 10.86 ± 2.04 | NS |

Study 5B: Single-Dose and Multi-Dose Steady-State Comparative Pharmacokinetics and Pharmacodynamics of GlycoBien® CR, Glucophage® XR and Glucophage®

This study determined the steady-state pharmacokinetics of GlycoBien® CR after multiple dosing and investigated the propensity of GlycoBien® CR and new once-daily dosing regimen before breakfast to reduce postprandial blood glucose excursions in comparison to Glucophage® (immediate release metformin) taken twice daily as used in clinical practice.

In a study titled: "Open Label, Multi-Dose, Randomized, Crossover, Comparative Pharmacokinetics and Pharmacodynamic study involving GlycoBien® CR 1000 mg q.d. and Glucophage® 500 mg b.i.d.", in Healthy Male and Female Volunteers", a total of fourteen (14) healthy male and female subjects were enrolled in a one-day placebo lead-in period, wherein each subject received one placebo tablet twice daily before breakfast and dinner. The subjects also received three glycemic load standardized meals for breakfast, lunch, dinner and snack. Following the placebo lead-in period, randomized subjects were administered either a single oral dose of GlycoBien® CR 1000 mg approximately 30 minutes before the glycemic load standardized breakfast or single oral dose of Glucophage® 500 mg twice-daily approximately 5 minutes after the glycemic load standardized breakfast and dinner in a two-period crossover study. During the placebo-lead in and each treatment period subjects were fed the same glycemic load standardized meals for breakfast, lunch, dinner and snack. The dosing regimens per treatment period was maintained for a total of seven (7) days separated by a seven (7) day washout. The seven (7) day treatment period comprised two confinement days (day 1 and day 7) and five (5) ambulatory days. During the ambulatory days, subjects were fed standardized meals after the breakfast dosing and before the dinner dosing according to their respective dosing regimens. In this study, four (4) subjects withdrew from the study due to personal reasons. Thus, ten (10) subjects (4 males and 6 females) completed the study.

During the one day placebo lead-in and day 1 single-dose treatment period, venous blood samples for metformin plasma and serum glucose analysis were obtained from subjects at 0.0 (pre-dose), and 0.5 hr., 1.5 hr., 2.5 hr., 3.5 hr., 4.5 hr., 5.5 hr., 6.5 hr., 7.5 hr., 8.5 hr., 9.5 hr., 10.5 hr., 11.5 hr., 12.5 hr., 13.5 hr., 15.0 hr., 16.0 hr., 18.0 hr., 20.0 hr., 24.0 hr post dose). During the five-day ambulatory period, blood samples for metformin plasma analysis were further taken each time before breakfast dosing or meal or before the dinner meals according to the dosing and treatment regimens. At steady-state, during the seventh day confinement, venous blood samples for metformin plasma and serum glucose analysis were obtained from subjects at 0.0 (pre-dose), and 0.5 hr., 1.5 hr., 2.5 hr., 3.5 hr., 4.5 hr., 5.5 hr., 6.5 hr., 7.5 hr., 8.5 hr., 9.5 hr., 10.5 hr., 11.5 hr., 12.5 hr., 13.5 hr., 15.0 hr., 16.0 hr., 18.0 hr., 20.0 hr., 24.0 hr., and 36.0 hr post dose.

Plasma concentrations of metformin were determined using a validated LC-MS-MS method. The lower quantitation limit of this method is 4.0 ng/ml. Mean plasma concentration profiles for the single and multi-dose steady-state pharmacokinetics are shown in FIGS. 10A and 10B and the mean values of the pharmacokinetic parameters of metformin obtained from the study are presented in Tables 10 and 11.

Serum concentrations of glucose were determined using a validated glucose oxidase method with a % CV of <5%. The positive incremental area under the blood glucose-concentration versus time curve (iAUC) over the meal periods breakfast, lunch and dinner were determined for each treatment period and compared with placebo baseline. The overall daily (24-hr) $iAUC_{0-24}$ were also determined for each treatment and compared with placebo baseline. Mean iAUC as an index of glucose excursions for the single-dose and multi-dose (steady-state) treatments are presented in FIGS. 11A through 11D and Tables 6 and 7.

Plasma insulin concentrations were determined by a validated plasma insulin assay method with a % CV of <5%. The total area under the blood insulin-concentration versus time curve (AUC) over the meal periods breakfast, lunch and dinner were determined for each treatment period and compared with placebo baseline. The overall daily (24-hr) insulin $AUC_{0-24}$ were also determined for each treatment and compared with placebo baseline. Mean insulin AUC for the single-dose and multi-dose (steady-state) treatments and the corresponding serum glucose AUC are presented in Table 12

Results

The pharmacokinetics and pharmacodynamic analysis illustrated in FIGS. 10A-10B and Tables 10-11 show that GlycoBien® CR has a faster increase in blood metformin concentration, achieving a higher peak plasma concentration compared to the immediate release metformin (Glucophage®) taken b.i.d. after meals. In addition, GlycoBien® CR produced a delayed time to peak concentration and sustained therapeutically relevant concentrations of metformin over a prolonged time period.

Although the total amount of drug exposure as determined by the metformin AUC from the Glucophage b.i.d. dose is slightly higher compared to GlycoBien® CR once-daily, the difference is not statistically significant and as such they are comparative in their extents of absorption. The treatment effect on postprandial glucose excursion over a period of 24-hrs is statistically and clinically more pronounced with GlycoBien® CR in comparison to Glucophage® b.i.d. The results are summarized as follows:

Pharmacokinetics:

FIGS. 10A and 10B shows the profile of GlycoBien® CR 1000 mg taken once-daily before breakfast is different and characteristic of a sustained release formulation in that the time to peak concentration is prolonged compared to the immediate release Glucophage® b.i.d. with meals. However, the rate of absorption and the maximum concentration achieved with GlycoBien® CR is novel and uncharacteristic of prior art extended release metformin in that it is significantly higher than that obtained with the immediate release metformin (e.g. Glucophage®). At steady state, after multiple dosing, the maximum metformin plasma concentration ($C_{max}$) attained for the two treatments are significantly different at 1.48 µg/L and 1.05 µg/L (p-value <0.03) for GlycoBien® CR 1000 mg once-daily and Glucophage® 500 mg b.i.d. respectively. The $T_{max}$ is also expectedly prolonged for GlycoBien® CR at 5.3 hr. relative to 4.3 hr for Glucophage® while total drug exposure at steady state ($AUC_{ss}$) for equivalent doses are not significantly different.

Pharmacodynamics (a) Postprandial Glucose Excursions:

The postprandial glucose excursion is a measure of the incremental increase in blood glucose above the fasting baseline and is determined over a period of time by the incremental positive area under the glucose vs. time curve (iAUC). As seen in Tables 11A through 11D, the postprandial glucose excursion lowering effect under standardized meal challenge over periods of breakfast, lunch and dinner are significantly different for the treatment regimens. Over the an entire 24-hr period and glycemic load standardized meals, the postprandial blood glucose excursion lowering effect of GlycoBien® CR is substantially higher than that observed with Glucophage® b.i.d. After seven days of ® treatment, at steady-state, the once-daily GlycoBien® CR 1000 mg taken before breakfast produced approximately 42% lowering of glucose excursion (iAUC$_{0-24}$) from baseline placebo compared with a 9% lowering achieved with Glucophage® 500 mg b.i.d. taken with breakfast and dinner meals. The treatments show a statistically significant difference of approximately 36% treatment with respect to glucose excursion lowering effect at a p-value of <0.056.

(b) Total Serum Glucose & Plasma Insulin:

As seen in Table 12, the total area under the plasma glucose concentration over a period of 24 hours following consumption of glycemic-load standardized meals for breakfast, lunch, dinner and snack (glucose AUC$_{0-24}$) is not significantly different between treatments regimens. In addition, the total area under the plasma insulin concentration is also not significantly different. This is expected, and confirms that the subjects were exposed to similar glucose challenges over the 24-hr period and have retained their innate glucose response capacity and have secreted total insulin commensurate to the glucose challenges from meals. FIGS. 12A and 12B show the single dose and multi-dose comparisons between treatments for total plasma glucose (glucose AUC$_{0-24}$), total glucose excursion (positive incremental glucose iAUC$_{0-24}$), and total insulin levels (insulin AUC$_{0-24}$) under different treatment regimens. This result further underpins and reiterates the fact that the active drug, metformin, does not have any effect on insulin secretion in healthy individuals and that similar drug exposures will result in similar overall glucose disposal, and that the rapid-absorption modified release metformin composition (GlycoBien® CR) potentiates insulin action and results in a superior postprandial glucose excursion lowering compared to prior art metformin formulation (Glucophage®).

TABLE 8

Mean ± SE, N = 10 values of Serum Glucose positive iAUC0-24 hr Pharmacodynamic Parameters of Daily Glucose Excursion after Single Dose Treatment in Healthy Subjects

| Treatment | iAUC$_{0-24}$ (mmol · min/L) | % Change from Placebo | Placebo Adjusted ΔiAUC$_{0-24}$ (mmol · min/L) | **% Diff. | *p-value |
|---|---|---|---|---|---|
| Placebo (taken with meal) | 741.21 ± 60.26 | N/A | N/A | | |
| GlycoBien ® CR 1000 mg (taken q.d. before breakfast) | 497.77 ± 99.46 | −32.84 | −243.44 ± 108.36 | −13.92 | NS |
| Glucophage ® 1000 mg (taken 500 MG b.i.d. with meals) | 578.27 ± 79.46 | −21.98 | −162.95 ± 98.59 | N/A | |

*ANCOVA p-values with placebo as covariate
**Difference from Glucophage ®

TABLE 9

Mean ± SE, N = 10 values of Serum Glucose positive iAUC0-24 hr Pharmacodynamic Parameters of Daily Glucose Excursion after 7 Days Treatment in Healthy Subjects

| Treatment | iAUC$_{0-24}$ (mmol · min/L) | % Change from Placebo | Placebo Adjusted ΔiAUC$_{0-24}$ (mmol · min/L) | **% Diff. | *p-value |
|---|---|---|---|---|---|
| Placebo (taken with meal) | 749.14 ± 58.47 | N/A | N/A | | |
| GlycoBien ® CR 1000 mg (taken q.d. before breakfast) | 429.65 ± 90.02 | −42.65 | −319.45 ± 82.76 | −36.84 | <0.056 |
| Glucophage ® 1000 mg (taken 500 MG b.i.d. with meals) | 680.27 ± 76.78 | −9.19 | −68.83 ± 90.27 | N/A | |

*ANCOVA p-values with placebo as covariate
**Difference from Glucophage ®

TABLE 10

GlycoBien ® CR Vs. Immediate Release Metformin (Glucophage ™)
Single-Dose Pharmacokinetic Parameters

| Parameters (N = 10) Mean ± SD | GlycoBien ® CR 1000 mg (administered q.d. before breakfast) | Glucophage ® 500 mg (administered b.i.d. with meals) | p-value |
|---|---|---|---|
| $C_{max}$ (μg/L) | 1.51 ± 0.43 | 1.02 ± 0.39 | <0.02 |
| $T_{max}$ (hr) | 5.0 ± 0.7 | 4.1 ± 0.9 | NS |
| $AUC_{0-24}$ (μg · hr/L) | 11.75 ± 3.9 | 13.28 ± 4.32 | NS |

TABLE 11

GlycoBien ® CR Vs. Immediate Release Metformin (Glucophage ™)
Steady-State Pharmacokinetic Parameters at Day 7

| Parameters (N = 10) Mean ± SD | GlycoBien ® CR 1000 mg (administered q.d. before breakfast) | Glucophage ® 500 mg (administered b.i.d. with meals) | p-value |
|---|---|---|---|
| $C_{max}$ (μg/L) | 1.48 ± 0.45 | 1.05 ± 0.31 | <0.03 |
| $T_{max}$ (hr) | 5.3 ± 1.4 | 4.3 ± 0.8 | NS |
| $AUC_{0-24}$ (μg · hr/L) | 12.95 ± 3.6 | 14.86 ± 4.16 | NS |

TABLE 12

GlycoBien ® CR Vs. Immediate Release Metformin (Glucophage ™)
Single-Dose and Steady-State Comparative Plasma Insulin and Serum Glucose Parameters

| Mean ± SD Single Dose Treatment | GlycoBien ® CR 1000 mg (administered q.d. before breakfast) | Glucophage ™ (1000 mg) (administered 500 mg b.i.d. with meals) | Placebo | p-value |
|---|---|---|---|---|
| Insulin $AUC_{0-24}$ (pmol · min/L) | 198,394 ± 54,359 | 199,039 ± 54,114 | 207,135 ± 48,179 | NS |
| Glucose $AUC_{0-24}$ (mmol · min/ml) | 7,314 ± 494 | 7,273 ± 503 | 7,466 ± 318 | NS |
| Fasting Insulin (pmol/L) | 66.3 ± 67.8 | 58.7 ± 24.9 | 39.1 ± 16.7 | |
| Fasting Glucose (mmol./ml) | 5.02 | 4.83 | 4.93 | |
| Steady-State Treatment at Day-7 | | | | |
| Insulin $AUC_{0-24}$ (pmol · min/L) | 197,658 ± 63,098 | 165,939 ± 56,816 | 207,135 ± 48,179 | NS |
| Glucose $AUC_{0-24}$ (mmol · min/ml) | 6,871 ± 473 | 6,987 ± 352 | 7,466 ± 318 | NS |
| Fasting Insulin (pmol/L) | 44.9 ± 26.1 | 48.4 ± 34.3 | 39.1 ± 16.7 | |
| Fasting Glucose (mmol./ml) | 4.76 | 4.52 | 4.93 | |

The preferred embodiments of the present invention have been described herein, including the best mode known to the inventor for carrying out the invention. It is expected that variations on those preferred embodiments will or may become apparent to those of ordinary skill in the art upon reading the foregoing description. The inventor expects skilled artisans to use such variations as appropriate, and the inventor intend for the invention may practiced otherwise than specifically described herein. Accordingly, this invention includes all modifications and equivalents of the subject matter recited in the claims appended hereto as permitted by applicable law. In addition, any combination of the above-described elements in all possible variations thereof is encompassed by the invention unless otherwise indicated herein or otherwise clearly contradicted by context.

Furthermore, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

All patents, patent applications and publications cited in this application are hereby incorporated by reference in their entirety for all purposes to the same extent as if each individual patent, patent application and publication were so individually denoted.

What is claimed is:

1. A multi-layer, controlled-release pharmaceutical tablet, comprising:
   a) a first layer containing an effective amount of an intimately mixed and granulated dose of metformin and an ionic surfactant, wherein cetyl alcohol has been added hot and rapidly cooled during high-shear granulation, and
   b) a second layer formed by: (1) completely coating granules of agglomerated mucoadhesive polymer with an enteric polymer, then (2) forming said granules into the second layer on only one side of the first layer.

2. The tablet of claim 1, wherein the mucoadhesive polymer is a copolymer of methyl vinyl ether and maleic anhydride.

3. The tablet of claim 1, wherein the mucoadhesive polymer is a mixed sodium and calcium salt of methyl vinyl ether and maleic anhydride copolymer.

4. The tablet of claim 1, wherein the mucoadhesive polymer is coated with an enteric polymer using high shear granulation and fluidized-bed coating of said mucoadhesive polymer.

5. The tablet of claim 1, wherein the enteric polymer is selected from the group consisting, of hydroxypropyl methyl cellulose phthalate (HPMCP), cellulose acetate phthalate (CAP), methacrylic acid-methyl methacrylate copolymer (1:1), and methacrylic acid-methyl methacrylate copolymer (1:2).

6. The tablet of claim 1, wherein the mucoadhesive polymer is selected from the group consisting of polyvinyl pyrrolidone (PVP), polymethylmethacrylate (Eudragit NE30D), poly(ethylene oxide) polymers, methyl cellulose (MC), sodium carboxymethylcellulose (SCMC), hydroxypropyl cellulose (HPC), a carbopol, a polyacrylate, a mixed sodium and calcium salt of poly(methylvinyl ether/maleic anhydride), a mixed sodium and calcium salt of poly(methylvinyl ether/maleic anhydride copolymer, chitosan, a derivative of chitosan and a mixture thereof.

7. The tablet of claim 1, wherein the ionic surfactant is selected from the group consisting of sodium or potassium dodecyl sulfate, sodium octadecylsulfate, sodium bis(2-ethylhexyl)sulfosuccinate (AOT), and a combination thereof.

8. The tablet of claim 1, wherein the surfactant is selected from the group consisting of didodecyl dimethyl ammonium bromide (DDAB), cetyl-triammonium bromide (eTAB), cetylpyridinium bromide (CPS), dodecyl trimethyl ammonium chloride (DOTAC), sodium perfluorononanoate (SPFN), hexadecyl trimethyl ammonium bromide (HDTMA), and a combination thereof.

9. The tablet of claim 1, wherein the pharmaceutical is for administration within 30 minutes prior to the beginning of the morning meal.

10. The table of claim 1, which is for once daily administration of metformin.

11. The table of claim 1, wherein
0-20% of the metformin or a pharmaceutically acceptable salt thereof is released after 0.5 hour;
20-30% of the metformin or a pharmaceutically acceptable salt thereof is released after 1 hour;
30-40% of the metformin or a pharmaceutically acceptable salt thereof is released after 2 hours;
35-45% of the metformin or a pharmaceutically acceptable salt thereof is released after 3 hours;
45-55% of the metformin or a pharmaceutically acceptable salt thereof is released after 5 hours;
55-65% of the metformin or a pharmaceutically acceptable salt thereof is released after 7 hours;
65-75% of the metformin or a pharmaceutically acceptable salt thereof is released after 11 hours;
75-85% of the metformin or a pharmaceutically acceptable salt thereof is released after 16 hours;
not less than 80% of the metformin or a pharmaceutically acceptable salt thereof is released after 19 hours; and
not less than 85% of the metformin or a pharmaceutically acceptable salt thereof is released after 24 hours.

12. The tablet of claim 1, wherein the pharmaceutical composition provides a mean time to maximum plasma concentration ($T_{max}$) of metformin of from 2.5 to 6.5 hours following administration before a meal.

13. The tablet of claim 1, wherein the pharmaceutical composition provides a width at 50% of the height of a mean plasma concentration/time curve of the metformin from about 1.0 to about 10 hours or a width at 25% of the height of mean plasma concentration/time curve of the metformin from about 0.25 to about 14 hours.

14. The tablet of claim 1, wherein the pharmaceutical composition provides a mean maximum plasma concentration (Cmax) of metformin which is from about 10 times to about 20 times the plasma level of the metformin at about 24 hours after administration.

15. The tablet of claim 1, wherein the pharmaceutical composition provides to mean maximum plasma concentration (Cmax) of metformin from about 1.18 µg/ml to about 1.60 µg/ml; based on administration of a 1000 mg once-a-day dose of metformin before a morning meal or breakfast.

16. The tablet of claim 1, wherein the pharmaceutical composition provides a mean $AUC_{0-24hr}$ from about 10.0 µg·hr/ml to about 13.0 µg·hr/ml based on administration of to 1000 mg once-a-day dose of metformin before a morning meal or breakfast.

17. The tablet of claim 1, wherein the pharmaceutical composition provides a mean drug exposure and $AUC_{0-24hr}$ from about 18.00 µg·hr/ml to about 22.00 µg·hr/ml, based on administration of a 2000 mg once-a day dose of metformin.

18. The tablet of claim 1, wherein the pharmaceutical composition provides a mean $t_{1/2}$ from 4.0 to 6.0.

* * * * *